(12) United States Patent
Nebuya

(10) Patent No.: US 11,614,418 B2
(45) Date of Patent: Mar. 28, 2023

(54) YARN, DETECTION SYSTEM, FIBER SHEET, CONNECTOR, DETECTION DEVICE, AND LIQUID TYPE ESTIMATION METHOD

(71) Applicant: SCHOOL JURIDICAL PERSON KITASATO INSTITUTE, Tokyo (JP)

(72) Inventor: Satoru Nebuya, Sagamihara (JP)

(73) Assignee: School Juridical Person Kitasato Institute, Tokyo (JP)

( * ) Notice: Subject to any disclaimer, the term of this patent is extended or adjusted under 35 U.S.C. 154(b) by 1376 days.

(21) Appl. No.: 15/740,087

(22) PCT Filed: Oct. 6, 2015

(86) PCT No.: PCT/JP2015/078337
§ 371 (c)(1),
(2) Date: Dec. 27, 2017

(87) PCT Pub. No.: WO2017/002274
PCT Pub. Date: Jan. 5, 2017

(65) Prior Publication Data
US 2018/0195985 A1 Jul. 12, 2018

(30) Foreign Application Priority Data
Jun. 30, 2015 (JP) .............................. JP2015-132024

(51) Int. Cl.
*A61B 5/02* (2006.01)
*G01N 27/12* (2006.01)
(Continued)

(52) U.S. Cl.
CPC .......... *G01N 27/02* (2013.01); *A61B 5/02042* (2013.01); *A61M 1/3656* (2014.02);
(Continued)

(58) Field of Classification Search
CPC . A61B 5/02042; A61M 1/3656; G01N 27/02; G01N 27/12; H01R 4/2406; H01R 9/0509
See application file for complete search history.

(56) References Cited

U.S. PATENT DOCUMENTS 3,864,676 A 2/1975 Macias et al.
4,614,394 A * 9/1986 Chelin ................. H01R 9/0509
439/391

(Continued)

FOREIGN PATENT DOCUMENTS

EP 3 130 363 A1 2/2017
JP 02-280039 11/1990
(Continued)

OTHER PUBLICATIONS

Partial Supplementary European Search Report dated Jun. 3, 2019 in European Application No. 15897201.8, 13 pages.
(Continued)

*Primary Examiner* — Meredith Weare
(74) *Attorney, Agent, or Firm* — Nixon & Vanderhye P.C.

(57) ABSTRACT

A yarn has a first conductive yarn having conductivity, a first insulating section covering the first conductive yarn and formed of an insulating material having absorbency, and a second conductive yarn having conductivity and disposed on an outer circumferential side of the first insulating section.

3 Claims, 37 Drawing Sheets

(51) Int. Cl.
*G01N 27/02* (2006.01)
*A61M 1/36* (2006.01)
*G01N 27/06* (2006.01)
*D02G 3/04* (2006.01)
*D02G 3/38* (2006.01)
*D02G 3/44* (2006.01)
*G01N 33/487* (2006.01)
*D02G 3/36* (2006.01)

(52) U.S. Cl.
CPC ................ *D02G 3/04* (2013.01); *D02G 3/38* (2013.01); *D02G 3/441* (2013.01); *G01N 27/06* (2013.01); *G01N 33/48785* (2013.01); *A61M 2205/15* (2013.01); *A61M 2205/3317* (2013.01); *D02G 3/36* (2013.01); *D10B 2401/16* (2013.01); *D10B 2509/00* (2013.01); *D10B 2509/02* (2013.01)

(56) References Cited

U.S. PATENT DOCUMENTS

| | | | | |
|---|---|---|---|---|
| 6,532,384 | B1* | 3/2003 | Fukuda | A61B 5/0537 600/547 |
| 2002/0189833 | A1* | 12/2002 | Eves | H01B 7/0009 174/36 |
| 2003/0056969 | A1* | 3/2003 | Eves | H01B 7/0009 174/68.1 |
| 2005/0054941 | A1* | 3/2005 | Ting | A61B 5/0408 600/529 |
| 2006/0122540 | A1* | 6/2006 | Zhu | A61B 5/6843 600/587 |
| 2010/0271212 | A1* | 10/2010 | Page | A61B 5/4216 340/573.1 |
| 2011/0132040 | A1 | 6/2011 | Jahn et al. | |
| 2014/0012199 | A1 | 1/2014 | Schroers et al. | |
| 2017/0199143 | A1* | 7/2017 | Nebuya | D02G 3/441 |
| 2018/0001021 | A1* | 1/2018 | Wu | A61M 1/3656 |

FOREIGN PATENT DOCUMENTS

| | | |
|---|---|---|
| JP | 2004-533103 | 10/2004 |
| JP | 2011-13004 A | 1/2011 |
| JP | 2011-106084 | 6/2011 |
| JP | 2012-196293 | 10/2012 |
| JP | 2013-205181 A | 10/2013 |
| WO | WO 2009/075592 A2 | 6/2009 |

OTHER PUBLICATIONS

S. Nebuya et al., "An Optically Isolated Impedance Measurement System", BPES 2001Dai Kai Proceeding of the Symposium on Biological and Physiological Engineering, 2001, 4 pages.

International Search Report for PCT/JP2015/078337 dated Dec. 28, 2015, 4 pages.

Extended European Search Report dated Mar. 6, 2020 in European Application No. 19192944.7, 11 pages.

Chuang, Ho-Chiao et al: "The Development of a Blood Leakage Monitoring System for the Applications in Hemodialysis Therapy", IEEE Sensors Journal, IEEE Service Center, vol. 15, No. 3, Mar. 1, 2015, XP011568123, New York, US ISSN: 1530-437X, DOI: 10.1109/JSEN.2014.2364302 [retrieved on Dec. 17, 2014], pp. 1515-1522.

* cited by examiner

YARN, DETECTION SYSTEM, FIBER SHEET, CONNECTOR, DETECTION DEVICE, AND LIQUID TYPE ESTIMATION METHOD

TECHNICAL FIELD

The present invention relates to a yarn, a detection system, a fiber sheet, a connector, a detection device and a liquid type estimation method.

This application is the U.S. national phase of International Application No. PCT/JP2015/078337 filed Oct. 6, 2015 which designated the U.S. and claims priority to Japanese Patent Application No. 2015-132024, filed Jun. 30, 2015, the entire contents of which are incorporated herein by reference.

BACKGROUND ART

Since removal of a needle during artificial dialysis may cause a serious accident due to abrupt bleeding, urgent detection is required when removal of the needle occurs. Accordingly, as a method of detecting removal of a needle, a method of detecting removal of a needle by detecting bleeding has been proposed. In this method, in order to prevent misdetection, it is desired to detect blood distinctly from sweat. In this way, it may be required to detect attachment of a specific liquid distinctly from attachment of another liquid on a sensor.

In relation to detection of removal of a needle during artificial dialysis, in a blood detection device for artificial dialysis disclosed in Patent Literature 1, a moisture sensor includes an electrode sheet, a filter sheet and a water-permeable sheet. The electrode sheet has a base sheet having a three-layer structure, and includes a reinforcement sheet. The reinforcement sheet has a plurality of micropores and has a permeability allowing water vapor to pass therethrough and also has a waterproof property in which water droplets are prevented from passing therethrough. A connector includes a lever and a clip. The lever and the clip sandwich one end portion and the other end portion of the moisture sensor. The clip includes a normal cross type switch. The switch is turned off when the clip holds the moisture sensor, and the switch is turned on when the clip is separated from the moisture sensor.

In Patent Literature 1, accordingly, bleeding due to removal of a needle and the probability of the needle having been removed can be reliably detected without malfunction due to sweat being caused.

CITATION LIST

Patent Literature

[Patent Literature 1]
Japanese Unexamined Patent Application, First Publication No. 2012-196293

SUMMARY OF INVENTION

Technical Problem

In the blood detection device for artificial dialysis disclosed in Patent Literature 1, the moisture sensor to which blood is adhered during bleeding has a complicated structure as described above. For this reason, manufacture of the moisture sensor is costly, and the moisture sensor may not be able to be discarded. On the other hand, from a viewpoint of more reliably preventing blood infection diseases, it is preferable that a portion to which blood may be adhered be discarded.

In this way, it is desirable that a portion to which the liquid is attached, the portion being capable of detecting attachment of a specific liquid such as blood or the like distinctly from other liquids such as sweat or the like, is disposable.

The present invention provides a yarn, a detection system, a fiber sheet, a connector, a detection device and a liquid type estimation method appropriate for a detection system capable of detecting attachment of a specific liquid distinctly from other liquids and enabling a portion to which the liquid is attached to be disposable.

Solution to Problem

According to a first aspect of the present invention, a yarn has a first conductive yarn having conductivity, a first insulating section covering the first conductive yarn and formed of an insulating material having absorbency, and a second conductive yarn having conductivity and disposed on an outer circumferential side of the first insulating section.

In the yarn, the second conductive yarn may be wound on an outer circumferential surface of the first insulating section in a spiral shape.

In the yarn, the second conductive yarn may be formed of an insulating material having absorbency.

The yarn may be coated with a third insulating section formed of an insulating material having absorbency.

In the yarn, the insulating material may be cotton.

According to a second aspect of the present invention, a detection system includes a fiber sheet and a detection device. The fiber sheet includes: a fiber sheet main body formed of an insulating material; and a sensor fiber including at least two conductive bodies that are combined such that they do not come in contact with each other. The sensor fiber has a first conductive yarn having conductivity, an insulating section covering the first conductive yarn and formed of an insulating material having absorbency, and a second conductive yarn having conductivity and disposed on an outer circumferential side of the insulating section. The detection device includes: an alternating current signal output unit configured to input an alternating current signal to between the at least two conductive bodies formed on the fiber sheet; a frequency characteristics acquisition unit configured to acquire frequency characteristics between the conductive bodies when the alternating current signal output unit inputs an alternating current signal to between the conductive bodies; and a detection signal output unit configured to output a detection signal when the alternating current signal output unit inputs a plurality of alternating current signals having different frequencies to between the conductive bodies and the frequency characteristics acquired by the frequency characteristics acquisition unit show a predetermined difference according to a difference in frequency of the alternating current signal from the alternating current signal output unit, and when the alternating current signal output unit inputs the alternating current signals having the same frequency to between the conductive bodies and the frequency characteristics obtained by the frequency characteristics acquisition unit at different times show a predetermined variation according to elapse of time.

In the detection system, the alternating current signal output unit may input at least three alternating current signals having different frequencies to between a plurality of conductive bodies formed on the fiber sheet. The frequency characteristics acquisition unit may acquire a value of impedance measured between the conductive bodies with each of the alternating current signals input by the alternating current signal output unit. The detection signal output unit may obtain a Cole-Cole trajectory that approximates impedance measurement values acquired by the frequency characteristics acquisition unit at a portion of an arc. By obtaining a value of a circuit parameter in a predetermined equivalent circuit model simulating an impedance of a liquid having a membrane on the basis of the Cole-Cole trajectory and estimating a type of the liquid on the basis of the obtained value of the circuit parameter, determination of whether the frequency characteristics shows a predetermined difference according to a difference in frequency of the alternating current signal from the alternating current signal output unit may be performed, wherein the frequency characteristics is acquired by the frequency characteristics acquisition unit when the alternating current signal output unit input a plurality of alternating current signal having different frequencies to between the conductive bodies.

According to a third aspect of the present invention, a fiber sheet includes: a fiber sheet main body formed of an insulating material; and a sensor fiber including at least two conductive bodies that are combined such that they do not come in contact with each other. The sensor fiber has a first conductive yarn having conductivity, an insulating section covering the first conductive yarn and formed of an insulating material having absorbency, and a second conductive yarn having conductivity and disposed on an outer circumferential side of the insulating section.

In the fiber sheet, the fiber sheet main body may have an elastic property in at least one direction, and the sensor fiber may be disposed in an extending direction of the fiber sheet main body in a waveform.

According to a fourth aspect of the present invention, a connector is configured to connect the first conductive yarn and the second conductive yarn to the detection device. The connector includes: a groove, to which the sensor fiber is fitted, extending in one direction; a terminal for a center conductor protruding to the vicinity of a center of the groove in a widthwise direction and configured to connect the first conductive yarn to the detection device, and a terminal for an external conductor protruding to the vicinity of an end portion of the groove in the widthwise direction and configured to connect the second conductive yarn and the detection device.

According to a fifth aspect of the present invention, a detection device includes: an alternating current signal output unit configured to input an alternating current signal to between a plurality of conductive bodies formed on a fiber sheet; a frequency characteristics acquisition unit configured to acquire frequency characteristics between the conductive bodies when the alternating current signal output unit inputs an alternating current signal to between the conductive bodies, and a detection signal output unit configured to output a detection signal when the alternating current signal output unit inputs a plurality of alternating current signals having different frequencies to between the conductive bodies and the frequency characteristics acquired by the frequency characteristics acquisition unit show a predetermined difference according to a difference in frequency of the alternating current signal from the alternating current signal output unit, and when the alternating current signal output unit inputs the alternating current signals having the same frequency to between the conductive bodies and the frequency characteristics acquired by the frequency characteristics acquisition unit at different times show a predetermined variation according to elapse of time.

According to a sixth aspect of the present invention, a liquid type estimation method includes: an alternating current signal inputting step of inputting at least three alternating current signals having different frequencies to between a plurality of conductive bodies formed on a fiber sheet; an impedance measurement value acquisition step of acquiring a value of impedance measured between the conductive bodies with each of the alternating current signals input in the alternating current signal inputting step; a Cole-Cole trajectory acquisition step of obtaining a Cole-Cole trajectory that approximates impedance measurement values obtained in the impedance measurement value acquisition step at a portion of an arc; a capacitance acquisition step of obtaining a value of a circuit parameter in a predetermined equivalent circuit model of simulating an impedance of a liquid having a membrane on the basis of the Cole-Cole trajectory; and a liquid type estimation step of estimating a type of the liquid on the basis of the obtained value of the circuit parameter.

Advantageous Effects of Invention

According to the present invention, it is possible to accurately determine whether a liquid dripping on a fiber sheet is a specific liquid (for example, blood), and it is possible to reduce the likelihood of incorrectly outputting a detection signal.

DESCRIPTION OF EMBODIMENTS

Hereinafter, while an embodiment of the present invention will be described, the following embodiment does not limit the present invention according to the scope of the claims. In addition, not all combinations of features described in the embodiment are necessarily essential in the solving means of the present invention.

Figure 1:
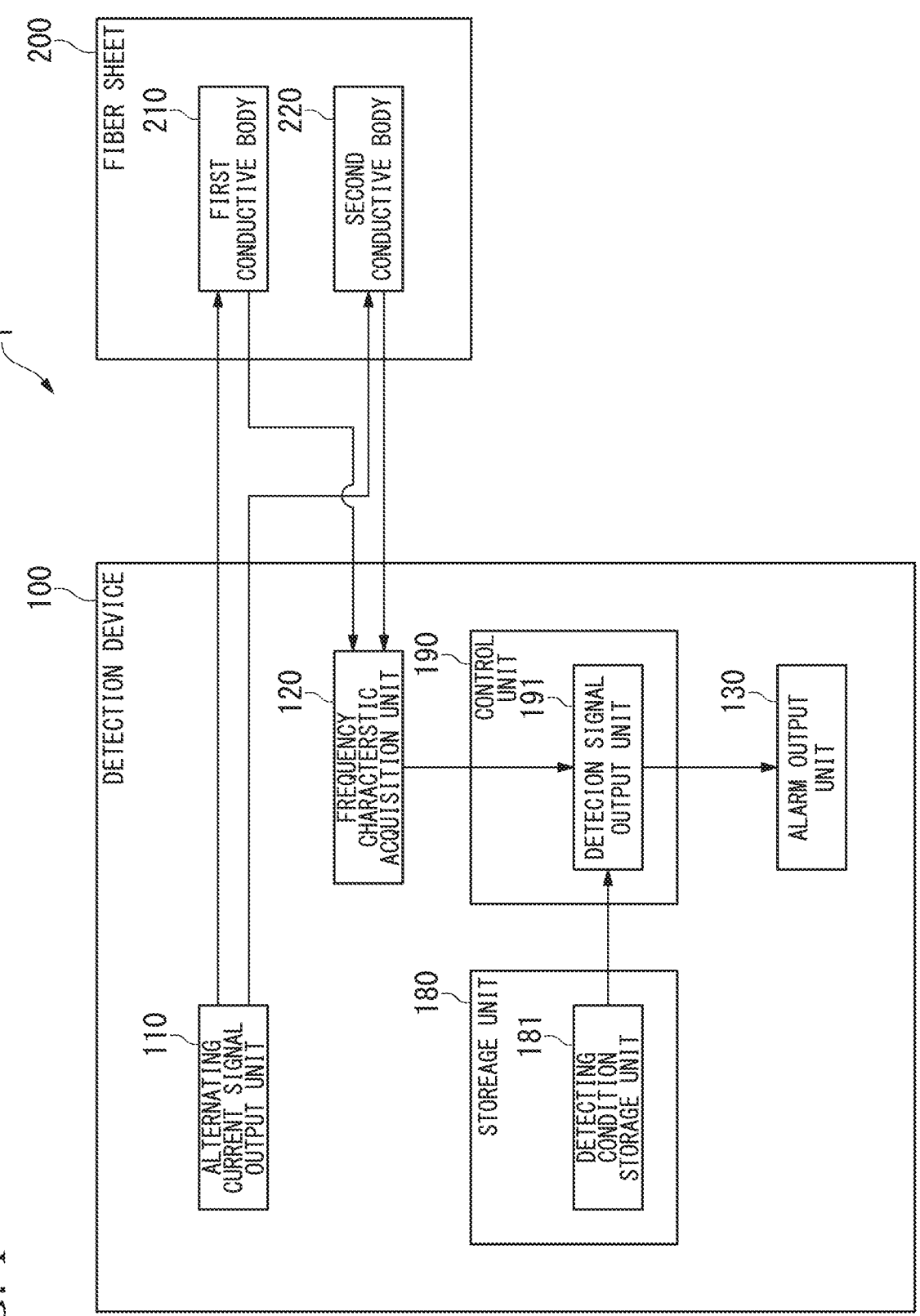
FIG. 1 is a schematic block diagram showing a functional configuration of a frequency characteristic detection system according to an embodiment of the present invention.

FIG. 1 is a schematic block diagram showing a functional configuration of a frequency characteristic detection system in the embodiment of the present invention. In FIG. 1, a detection system 1 includes a detection device 100 and a fiber sheet 200. The detection device 100 includes an alternating current signal output unit 110, a frequency characteristics acquisition unit 120, an alarm output unit 130, a storage unit 180 and a control unit 190. The storage unit 180 includes a detecting conditions storage unit 181. The control unit 190 includes a detection signal output unit 191. The fiber sheet 200 includes a first conductive body 210 and a second conductive body 220.

The detection system 1 detects removal of a needle by detecting a blood leakage during artificial dialysis.

Figure 2:
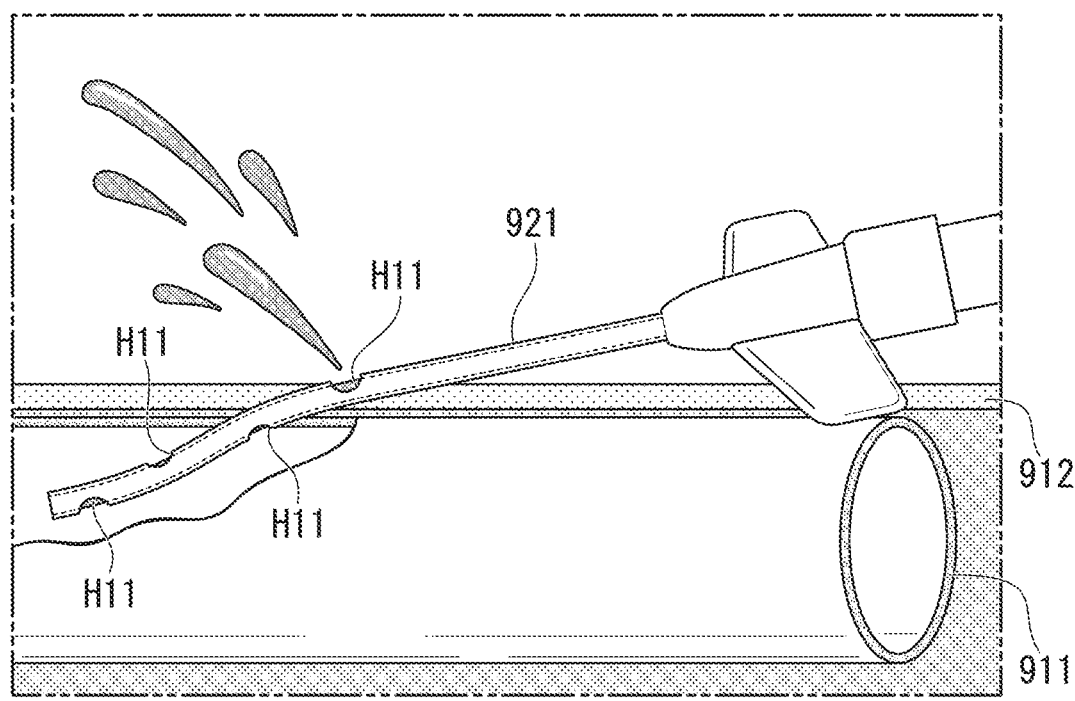
FIG. 2 is a view describing an example of removal of a needle during artificial dialysis.

FIG. 2 is a view describing an example of removal of a needle during artificial dialysis. In FIG. 2, a Teflon needle (Teflon is a trademark) 921 is inserted into a blood vessel 911, and side grooves H11 are formed in the Teflon needle 921. The Teflon needle 921 is inserted into an artery on a side of taking blood from the body to an artificial dialyzer. In addition, the Teflon needle 921 is inserted into a vein on a side of returning blood from the artificial dialyzer to the body.

In FIG. 2, a portion of the Teflon needle 921 has escaped outside of the body (outside the skin 912), and blood has leaked from the side groove H11 exposed outside of the body.

In particular, removal of a needle occurs more easily on the blood returning side than on the blood taking side due to the influence of the blood pressure being increased in the artificial dialyzer. In addition, also when the blood vessel becomes brittle due to repeated artificial dialysis, the influence of diabetes, or the like, removal of the needle occurs easily.

The fiber sheet 200 is a bandage wrapped around an arm punctured by a needle, i.e., a blood leakage observation target area during artificial dialysis. For example, a patient may lie on a bed and receive dialysis during artificial dialysis. Then, the fiber sheet 200 is wrapped around a patient's arm, and the patient's arm around which the fiber sheet 200 is wrapped is punctured by the Teflon needle 921 (FIG. 2). The fiber sheet 200 has absorbency and prevents blood, sweat, or the like, from leaking toward the bed. The fiber sheet 200 may have a waterproof property in addition to or instead of absorbency. Accordingly, leakage of blood, sweat, or the like, toward the bed can be more securely prevented.

When the patient moves greatly, for example, rolls over on the bed, in a usage where the fiber sheet 200 is laid on the bed and the patient's arm is placed thereon, the blood may leak to the outside of the fiber sheet 200 depending on a size of the fiber sheet 200.

With regard to this, as the fiber sheet 200 configured as the bandage is wrapped around the blood leakage observation target area and used, the likelihood that the fiber sheet 200 may escape from the blood leakage observation target area can be reduced, and a blood leakage can be more securely detected.

In addition, the puncture portion may be wound and fixed with the bandage, for example, when there is a possibility that the patient may remove the needle by himself/herself. In this case, in usage where the fiber sheet 200 is laid on the bed and the patient's arm is placed thereon, the detection device 100 may not detect a blood leakage in the bandage. On the other hand, when the puncture portion is wound and fixed with the fiber sheet 200 configured as the bandage, the detection device 100 can more securely detect the blood leakage in the bandage.

Further, for a short-term use where the patient does not move, the fiber sheet 200 may be laid under the patient's arm.

In addition, a fiber sheet 200 configured as gauze can be used by being wrapped with a bandage such that it abuts the blood leakage observation target area. When the fiber sheet 200 configured as gauze abuts the blood leakage observation target area by being used by being wrapped with a bandage, it is possible to reduce the likelihood that the fiber sheet 200 may escape from the blood leakage observation target area, and a blood leakage can be more securely detected.

The first conductive body 210 and the second conductive body 220 are conductive bodies formed on the fiber sheet 200, and an alternating current signal from the alternating current signal output unit 110 is input thereto.

The first conductive body 210 and the second conductive body 220 are not in contact with each other. In addition, a main body (a portion which becomes a base on which the first conductive body 210 and the second conductive body 220 are formed) of the fiber sheet 200 is fabricated of insulating fibers. For this reason, in a state in which a liquid is not attached to the fiber sheet 200, the first conductive body 210 and the second conductive body 220 are insulated from each other, or only a minute alternating current due to a capacitor effect or the like flows therebetween.

When a liquid drips between the first conductive body 210 and the second conductive body 220, the first conductive body 210 and the second conductive body 220 electrically conduct with frequency characteristics according to the dripping liquid.

Further, as the fiber sheet 200 has absorbency and diffuses the liquid, even when the liquid drips to a position other than between the first conductive body 210 and the second conductive body 220, it is possible to increase the likelihood that the first conductive body 210 and the second conductive body 220 electrically conduct. In particular, it is possible to increase the likelihood that the detection system 1 can detect a leakage of blood.

Further, there may be a configuration in which the patient's arm does not directly come into contact with the first conductive body 210 or the second conductive body 220, due to, for example, an insulating layer having absorbency being formed on surfaces of the first conductive body 210 and the second conductive body 220, and so on. Alternatively, a leakage of blood may be detected when the detection system 1 (the detection device 100) detects electrical conduction properties (frequency characteristics) that are able to be distinguished from contact of the patient's arm.

Various materials having conductivity may be used as a material of the first conductive body 210 or the second conductive body 220. For example, weaving may be performed during manufacture of the fiber sheet 200 using a conductive yarn (a yarn having conductivity) for the first conductive body 210 or the second conductive body 220. Alternatively, sewing may be performed on a main body of the fiber sheet 200 after manufacture using a conductive yarn for the first conductive body 210 or the second conductive body 220.

Tactile properties of the fiber sheet 200 can be improved using a conductive yarn for the first conductive body 210 or the second conductive body 220. Accordingly, when the patient puts his/her arm on the fiber sheet 200, no discomfort is caused.

The detection device 100 inputs an alternating current signal to the fiber sheet 200, and determines whether a blood leakage occurs by acquiring frequency characteristics on the side of the fiber sheet 200.

The detection device 100 can utilize various signals in which voltages are varied (i.e., signals having various frequencies) as an alternating current signal input to the fiber sheet 200. For example, the detection device 100 may be configured to input a sine wave, a triangular wave, or a square wave to the fiber sheet 200.

In addition, frequency characteristics acquired by the detection device 100 may be various data measured according to a frequency of the alternating current signal that was input. In the embodiment, while the case in which the detection device 100 measures a magnitude of an impedance or a phase rotation as frequency characteristics has been exemplarily described, there is no limitation thereto. Further, while measurement of the impedance has been exemplarily described using a two-electrode method, a four-electrode method or the like may be used.

The detection device 100 may be configured to include a microcomputer. Alternatively, a configuration other than a configuration including a microcomputer may be provided, for example, parts of the detection device 100 may be configured as a dedicated circuit, or a circuit may be configured using a smart phone, a personal computer, or the like.

The alternating current signal output unit 110 outputs an alternating current signal to be input to the fiber sheet 200. Specifically, the alternating current signal output unit 110 inputs the alternating current signal to between a plurality of conductive bodies (in the embodiment, between the first conductive body 210 and the second conductive body 220) formed on the fiber sheet 200. As described above, various signals in which voltages are varied may be used as alternating current signals output from the alternating current signal output unit 110.

The frequency characteristics acquisition unit 120 acquires frequency characteristics between the conductive bodies when the alternating current signal output unit 110 inputs the alternating current signal to between the plurality of conductive bodies formed on the fiber sheet 200. For example, the frequency characteristics acquisition unit 120 may measure the phase rotation of the alternating current signal in the fiber sheet 200 with respect to the magnitude of the impedance of the fiber sheet 200 at the frequency of the alternating current signal output from the alternating current signal output unit 110 or the alternating current signal output from the alternating current signal output unit 11. Further, for example, the frequency characteristics acquisition unit 120 may measure the phase rotation with respect to the impedance between the first conductive body 210 and the second conductive body 220 or the alternating current signal output from the alternating current signal output unit 110 of the current flowing between the first conductive body 210 and the second conductive body 220.

In particular, the frequency characteristics acquisition unit 120 acquires frequency characteristics when an alternating current signal having a first frequency and an alternating current signal having a second frequency are input to the first conductive body 210 and the second conductive body 220.

As described below, in blood and sweat, magnitudes of variation in impedance with respect to variation in frequency or magnitudes of variation in phase rotation are different. Here, the frequency characteristics acquisition unit 120 measures frequency characteristics when alternating current signals having different frequencies are input to the first conductive body 210 and the second conductive body 220.

When the detection device 100 (the detection signal output unit 191) detects a leakage of blood on the basis of the frequency characteristics of alternating current signals having different frequencies, blood and sweat can be distinguished between. Accordingly, there is less misdetection of removal of a needle.

The alarm output unit 130 outputs an alarm when the detection device 100 (the detection signal output unit 191) detects a leakage of blood on the basis of the frequency characteristics acquired by the frequency characteristics acquisition unit 120.

Various methods may be used as an alarm output method of the alarm output unit 130. For example, the alarm output unit 130 may include a speaker, and may output an alarm sound according to the detection signal output from the detection signal output unit 191. Alternatively, the alarm output unit 130 may include a lamp in addition to or instead of a speaker, and may output an alarm while emitting light from the lamp. Alternatively, the alarm signal may be transmitted to other devices, for example, the alarm output unit 130 may transmit an alarm signal to a personal computer (PC) installed in a nursing center.

The storage unit 180 may be configured to include a storage device included in the detection device 100, and store various data.

The detecting conditions storage unit 181 stores a determining threshold regarding whether the detection signal output unit 191 outputs a detection signal. That is, the threshold is used as a detecting condition when the detection signal output unit 191 determines whether a leakage of blood is detected.

The control unit 190 controls the parts of the detection device 100 such that they perform various functions. For example, the control unit 190 may be realized as a central processing unit (CPU) included in the detection device 100 may read a program from the storage unit 180 and execute the program.

The detection signal output unit 191 outputs the detection signal when the frequency characteristics acquisition unit 120 acquires predetermined frequency characteristics. More specifically, the detection signal output unit 191 determines whether the frequency characteristics acquired by the frequency characteristics acquisition unit 120 satisfy the detecting condition stored in the detecting conditions storage unit 181. Then, the detection signal output unit 191 outputs a detection signal to the alarm output unit 130 when it is determined that the detecting condition is satisfied.

In particular, the detection signal output unit 191 outputs the detection signal when the alternating current signal output unit 110 inputs a plurality of alternating current signals having different frequencies to between the conductive bodies (between the first conductive body 210 and the second conductive body 220) and the frequency characteristics acquired by the frequency characteristics acquisition unit 120 show a predetermined difference according to a difference in frequency of the alternating current signal from the alternating current signal output unit 110, and the alternating current signal output unit 110 inputs the alternating current signals having the same frequency to between the conductive bodies and frequency characteristics at different times acquired by the frequency characteristics acquisition unit 120 show a predetermined variation according to an elapsed time.

For example, the alternating current signal output unit 110 may input alternating current signals to between the first conductive body 210 and the second conductive body 220 a plurality of times while varying the frequency. Then, the frequency characteristics acquisition unit 120 measures frequency characteristics (for example, impedance or a phase) between the first conductive body 210 and the second conductive body 220 whenever the alternating current signal output unit 110 inputs an alternating current signal. Then, the detection signal output unit 191 determines whether the frequency characteristics between the first conductive body 210 and the second conductive body 220 have varied by a predetermined magnitude or more according to variation in frequency of the alternating current signal from the alternating current signal output unit 110.

In addition, the alternating current signal output unit 110 inputs the alternating current signal to between the first conductive body 210 and the second conductive body 220, and inputs an alternating current having the same frequency again after a predetermined time elapses. The number of times the alternating current signal is input by the alternating current signal output unit 110 may be two or may be three or more. Alternatively, the alternating current signal output unit 110 may continue to input the alternating current signals having the same frequency to between the first conductive body 210 and the second conductive body 220 over a predetermined time.

Then, the frequency characteristics acquisition unit 120 measures frequency characteristics between the first conductive body 210 and the second conductive body 220 a plurality of times when the alternating current signal output unit 110 inputs the alternating current signals having the same frequency. Then, the detection signal output unit 191 determines whether the frequency characteristics between the first conductive body 210 and the second conductive body 220 have varied by a predetermined magnitude or more according to elapse of time until the frequency characteristics acquisition unit 120 measures the frequency characteristics and then acquire the frequency characteristics.

Then, the detection signal output unit 191 outputs the detection signal to the alarm output unit 130 when the frequency characteristics between the first conductive body 210 and the second conductive body 220 are varied by a predetermined magnitude or more according to a variation in frequency of the alternating current signal from the alternating current signal output unit 110 and the frequency characteristics acquisition unit 120 determines that the frequency characteristics between the first conductive body 210 and the second conductive body 220 are varied by a predetermined magnitude or more according to elapse of time until the frequency characteristics are measured and then the frequency characteristics are acquired.

In this way, as the detection signal output unit 191 determines both of a difference in frequency characteristics on the basis of a difference in input frequency and a variation in frequency characteristics on the basis of elapse of time, it becomes possible to accurately determine whether blood drips onto the fiber sheet 200.

Next, a determining condition with which the detection signal output unit 191 detects a leakage of blood will be described with reference to FIGS. 3 to 8. In an experiment, different frequency characteristics were obtained for pig blood that simulates human blood and a saline solution that simulates sweat, and on the basis of the experimental results, a determining condition with which the detection signal output unit 191 can detect leakage of blood can be set.

Figure 3:
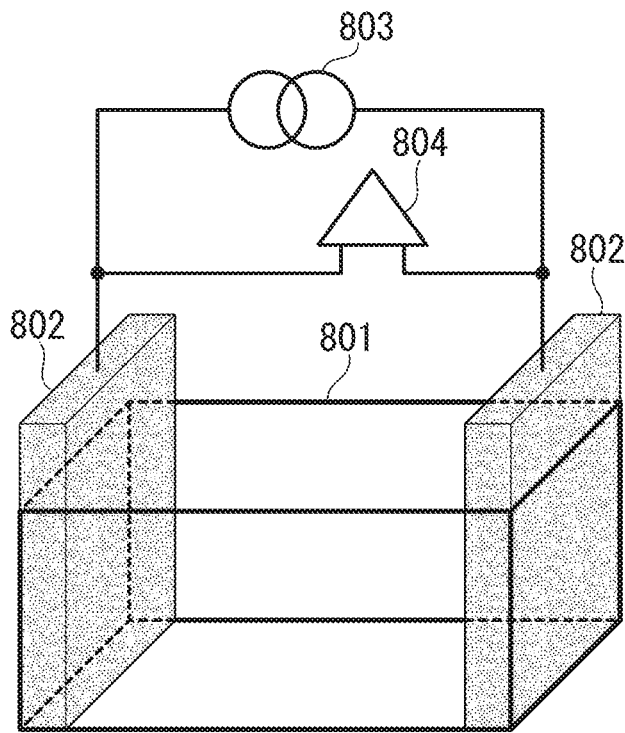
FIG. 3 is an external view showing a schematic exterior of a container and a measurement electrode used in an experiment in relation to the embodiment.

FIG. 3 is an external view showing a schematic exterior of a container and a measurement electrode used in the experiment. In the experiment, electrodes 802 were inserted into both ends of an acrylic container 801, and blood or a saline solution was put in the container. The acrylic container 801 was placed in a thermostatic oven, and the experiment was performed at a temperature close to body temperature (37 degrees (° C.)).

The electrodes 802 were connected to a constant current source 803 and an alternating current signal flowed. The electrodes 802 were connected to a voltmeter 804, and a voltage between the electrodes 802 was measured by the voltmeter 804.

The electrodes 802 simulate the first conductive body 210 and the second conductive body 220. The constant current source 803 simulates the alternating current signal output unit 110. The voltmeter 804 simulates the frequency characteristics acquisition unit 120.

Figure 4:
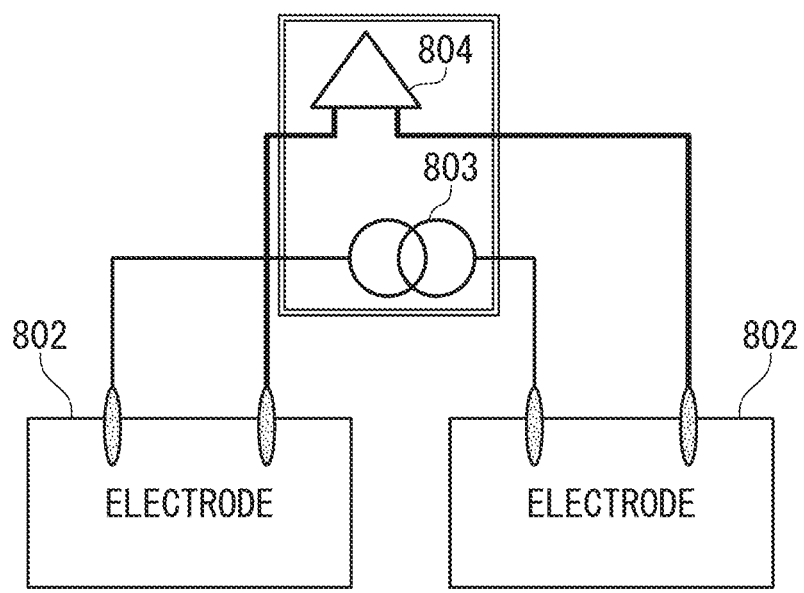
FIG. 4 is a view describing a schematic configuration of a circuit in the experiment in relation to the embodiment.

FIG. 4 is a schematic view describing a circuit in the experiment. In FIG. 4, the constant current source 803 is connected between the two electrodes 802, and an alternating current signal is input to the two electrodes 802. The voltmeter 804 is connected between the two electrodes 802, and measures a voltage between the two electrodes 802.

In addition, in the experiment, an average value was calculated using blood of 10 pigs. A hematocrit value (Hct) of the blood used in the experiment was about 40 percent (%).

In addition, in non-coagulated blood, sodium citrate was used as anticoagulant.

Figure 5:
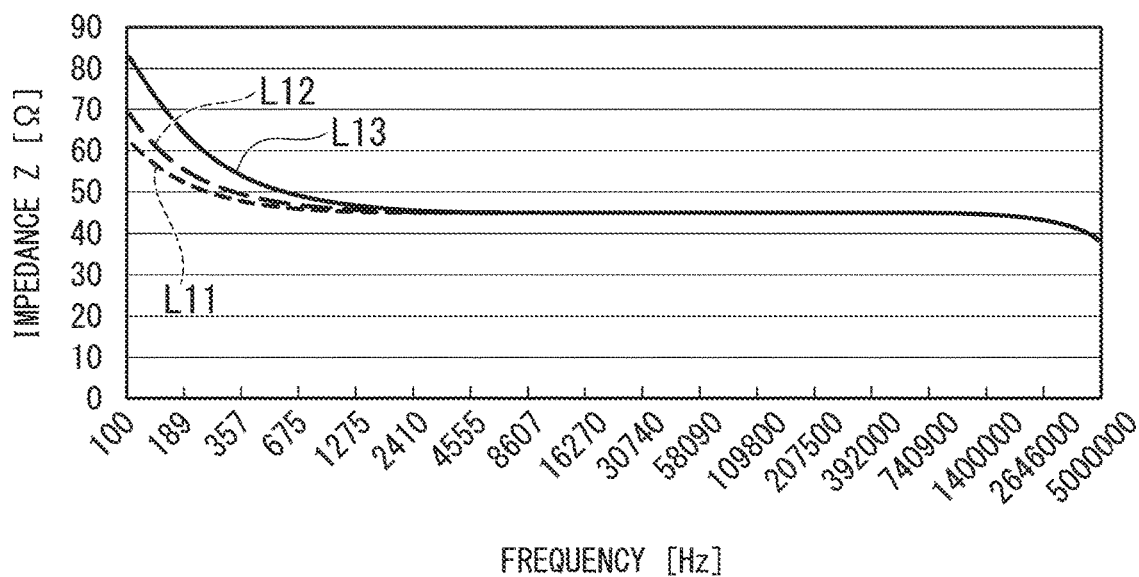
FIG. 5 is a graph showing measurement results of a magnitude Z of impedance in a state in which a saline solution is contained in an acrylic container in the experiment in relation to the embodiment.

FIG. 5 is a graph showing measurement results of a magnitude Z of impedance in a state in which a saline solution was put in the acrylic container 801. Further, a magnitude of impedance is also simply expressed as an impedance. A horizontal axis of the graph shown in FIG. 5 represents a frequency, and a vertical axis represents an impedance.

In the experiment, a saline solution was put into three acrylic containers 801 (hereinafter, referred to as a container A, a container B and a container C) having different sizes to measure impedance. The frequency characteristics in a state in which a saline solution is put in the acrylic container 801 represent frequency characteristics of the acrylic container 801. In addition, the frequency characteristics in a state in which a saline solution is put in the acrylic container 801 simulate frequency characteristics of sweat.

Lines L11, L12 and L13 represent measurement values of impedance in the container A, the container B and the container C, respectively. All of the lines L11, L12 and L13 represent approximately constant impedance within a range of about 3 kilohertz (kHz) to about 2 megahertz (MHz). It is considered that contact impedance of the electrode and an influence of the measurement cable occur outside this frequency range.

Figure 6:
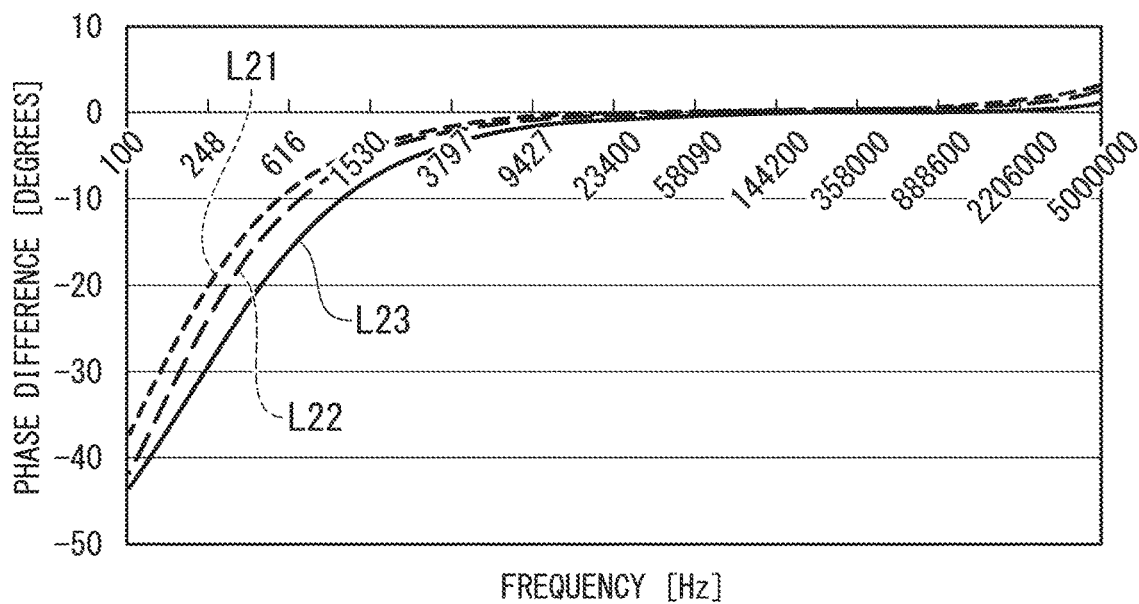
FIG. 6 is a graph showing measurement results of a phase difference (phase rotation) in a state in which the saline solution is contained in the acrylic container in the experiment in relation to the embodiment.

FIG. 6 is a graph showing measurement results of a phase difference (phase rotation) in a state in which a saline solution is put in the acrylic container 801. The phase difference is a difference between a phase of the alternating current signal output from the constant current source 803 and a phase of the alternating current signal between the electrodes 802 in which the voltmeter 804 measures a voltage.

A horizontal axis of a graph shown in FIG. 6 represents a frequency, and a vertical axis represents a phase difference. In addition, lines L21, L22 and L23 represent phase differences in the container A, the container B and the container C, respectively. All of the lines L11, L12 and L13 represent an approximately constant phase difference (a phase difference is approximately 0) within a range of about 40 kilohertz to about 2 megahertz.

In the measurement results in FIGS. 5 and 6, in the saline solution, the amplitude and the phase are approximately constant within a range of about 40 kilohertz to about 2 megahertz. It is considered that contact impedance of the electrode and an influence on the measurement cable occurs in the other frequency range.

Figure 7:
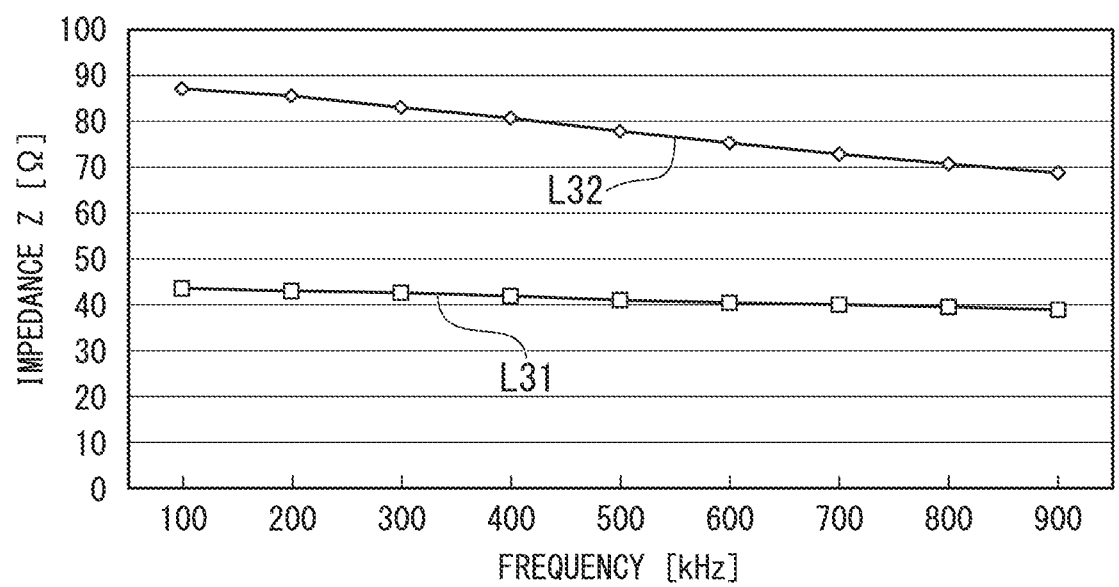
FIG. 7 is a graph showing measurement results of a magnitude Z of impedance in a state in which pig blood is contained in the acrylic container in the experiment in relation to the embodiment.

FIG. 7 is a graph showing measurement results of the magnitude Z of the impedance in a state in which pig blood is put in the acrylic container 801. A horizontal axis of the graph shown in FIG. 7 represents a frequency, and a vertical axis represents impedance. The frequency characteristics in the state in which pig blood is put in the acrylic container 801 simulate the frequency characteristics of human blood.

A line L31 represents impedance of non-coagulated blood, and a line L32 represents impedance of coagulated blood.

In the non-coagulated blood shown by the line L31, the impedance decreases as the frequency increases from 100 kilohertz to 900 kilohertz. In addition, the impedance increases more in the coagulated blood shown by the line L32 than in the non-coagulated blood, and a rate of reduction in impedance with respect to an increase in frequency is higher.

Figure 8:
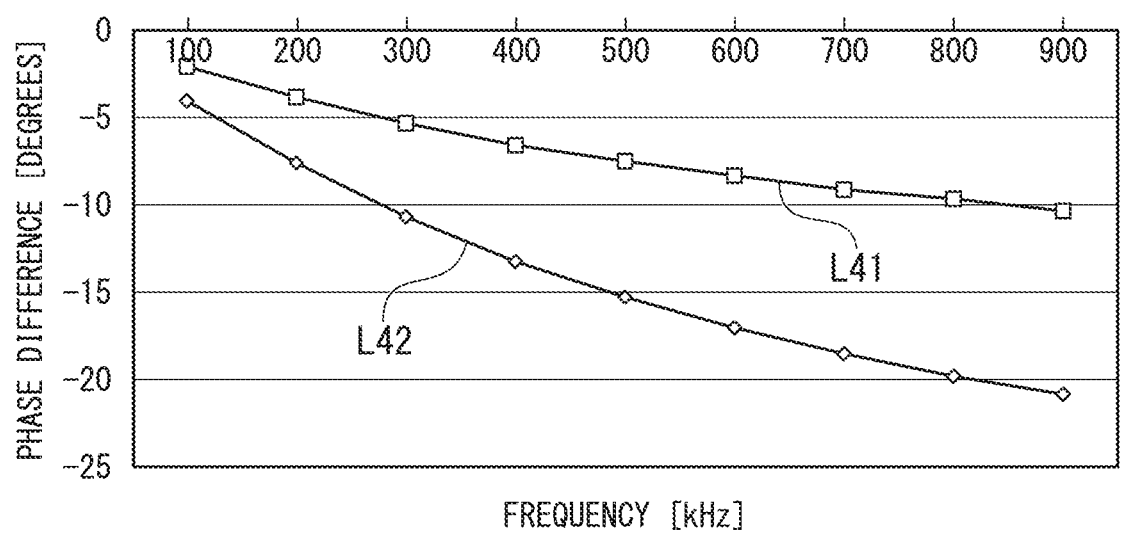
FIG. 8 is a graph showing measurement results of a phase difference (phase rotation) in a state in which pig blood is contained in the acrylic container in the experiment in relation to the embodiment.

FIG. 8 is a graph showing measurement results of a phase difference (phase rotation) in a state in which pig blood is put in the acrylic container 801. Similar to the case of FIG. 6, a phase difference in FIG. 8 is a difference between a phase of the alternating current signal output from the constant current source 803 and a phase of the alternating current signal between the electrodes 802 in which the voltmeter 804 measures a voltage. A horizontal axis of the graph shown in FIG. 8 represents a frequency, and a vertical axis represents a phase difference.

A line L41 represents a phase difference in the non-coagulated blood. A line L42 represents a phase difference in the coagulated blood.

In the non-coagulated blood shown by the line L41, a phase difference (a phase delay) is increased as the frequency is increased from 100 kilohertz to 900 kilohertz. In addition, the phase difference is increased more in the coagulated blood shown by the line L42 than in the non-coagulated blood, and a ratio of an increase in phase delay with respect to an increase in frequency is also increased.

In the measurement results shown in FIGS. 5 to 8, it can be assumed that the saline solution (sweat) and the blood could be distinguished by comparing an amplitude or a phase, or both in the case of a relatively low frequency and the case of a relatively high frequency. Specifically, the liquid is determined as the saline solution or the sweat when a variation corresponding to a variation in frequency is relatively small, and the liquid is determined as the blood when the variation is relatively large.

For example, the alternating current signal of 100 kilohertz or less is used in the case of the relatively low frequency. In addition, for example, the alternating current signal of 900 kilohertz or more is used in the case of the relatively high frequency.

The alternating current signal output unit 110 inputs the alternating current signal of 100 kilohertz that is the alternating current signal of the first frequency to the first conductive body 210 and the second conductive body 220. In addition, the alternating current signal output unit 110 inputs the alternating current signal of 900 kilohertz that is the alternating current signal of the second frequency to the first conductive body 210 and the second conductive body 220.

In addition, the frequency characteristics acquisition unit 120 measures a phase delay with respect to the current output from the alternating current signal output unit 110, of the impedance between the first conductive body 210 and the second conductive body 220 and the current between the first conductive body 210 and the second conductive body 220 in the case of the first frequency and the case of the second frequency.

Then, for example, the detection signal output unit 191 outputs the detection signal when the measurement value from the frequency characteristics acquisition unit 120 satisfies both of the following conditions (1) and (2).

(1) A magnitude of the impedance in the case of the second frequency is 95% or less of a magnitude of the impedance in the case of the first frequency (i.e., reduced by 5 percent or more).

(2) A magnitude of the phase delay in the case of the second frequency with respect to a magnitude of the phase delay in the case of the first frequency is two times or more.

In the example shown in FIG. 7 or 8, both of conditions (1) and (2) are satisfied. Like the example shown in FIG. 5 or 6, it is considered that, in the case of the saline solution or sweat, a variation in impedance or phase delay is scarcely observed, and the condition (1) or (2) is not satisfied.

Accordingly, a flow of the blood can be detected and misdetection due to sweat can be reduced using the condition (1) or (2), or both of them.

In addition, as shown in FIG. 7 or 8, since the variation in phase is different between the non-coagulated blood and the coagulated blood, the detection signal output unit 191 can set the detecting condition such that the coagulated blood and the non-coagulated blood are distinctly detected.

For example, the detection signal output unit 191 may be configured to detect a variation in a state in which the leaked blood is coagulated according to elapse of time using the fiber sheet 200 on the gauze or the bandage abutting a wound after a surgery or the like. More specifically, the detection signal output unit 191 includes a timer, and determines whether blood coagulation occurs when it is detected that a predetermined time has elapsed from termination of a surgery or the like. When it is determined that blood coagulation has not occurred, the detection device 100 outputs an alarm that prompts confirmation of hemostasis.

In addition, after the bleeding from the wound stops, when the detection signal output unit 191 detects non-coagulated blood, the detection device 100 may be configured to output an alarm showing the possibility that the wound is open.

Next, a measurement experiment of a variation with time in frequency characteristics using a sensor fiber (yarn) will be described with reference to FIGS. 9 to 12.

Figure 9:
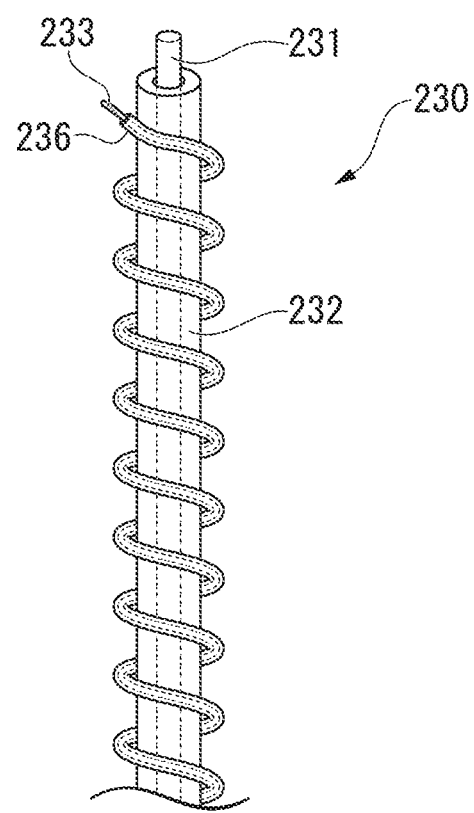
FIG. 9 is a structural view showing a schematic structure of a sensor fiber used in the experiment in relation to the embodiment.
Figure 10:
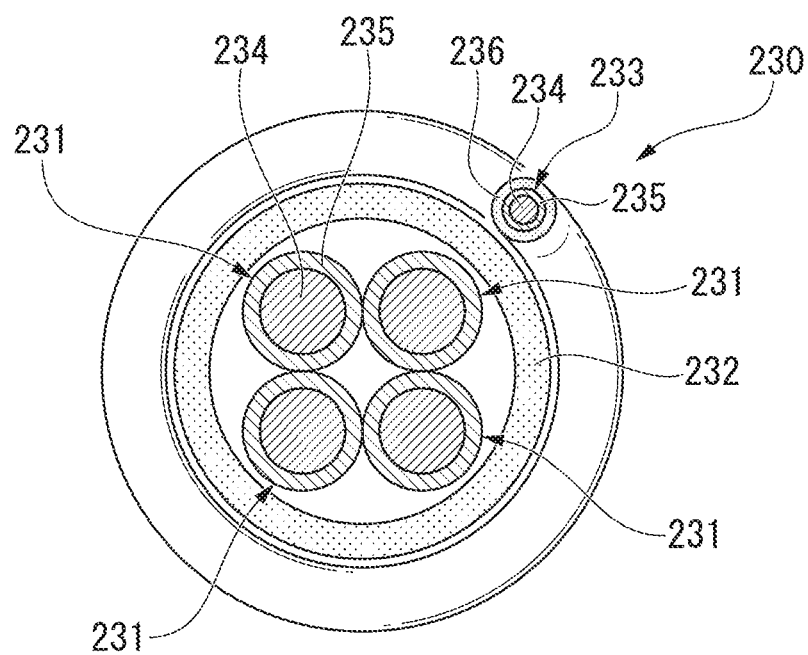
FIG. 10 is a view describing a layer structure of the sensor fiber in the experiment in relation to the embodiment.

FIGS. 9 and 10 are structural views showing a schematic structure of the sensor fiber. A sensor fiber 230 shown in FIGS. 9 and 10 has conductive yarns 231 and 233 each having a core 234 formed of an organic fiber and a copper foil 235 configured to coat the core 234. Each of the conductive yarn 231 and the conductive yarn 233 is coated with an insulating cotton 232 (a first insulating section) that is an insulating material having absorbency, and a second insulating cotton 236 (a second insulating section). Specifically, the sensor fiber 230 is configured by coating a conductive yarn group configured of a plurality of first conductive yarns 231 (functioning as the first conductive body 210) with the insulating cotton 232 and winding the second conductive yarn 233 (functioning as the second conductive body 220) coated with an insulating cotton 236 on an outer circumference of the insulating cotton 232 in a spiral shape. That is, the second conductive yarn 233 is disposed on an outer circumferential side of the second insulating section 236.

As the first conductive yarn 231 is coated with the insulating cotton 232 and the second conductive yarn 233 is coated with the insulating cotton 236, the conductive yarns 231 and 233 do not directly come into contact with a body surface of the like.

Further, the insulating material that coats the conductive yarns 231 and 233 is not limited to cotton and any material may be employed as long as an insulating material has absorbency. For example, rayon, silk, or the like, may be employed.

FIG. 10 is a view describing a layer structure of the sensor fiber 230. FIG. 10 shows a layer structure in a cross section of the sensor fiber 230. As shown in FIG. 10, the insulating cotton 232 and the insulating cotton 236 are interposed between the conductive yarn 231 and the conductive yarn 233. When the insulating cotton 232 and the insulating cotton 236 absorb the liquid, frequency characteristics between the conductive yarn 231 and the conductive yarn 233 vary.

A main reason for such a coaxial structure is reduction of noise due to a body motion or lap winding on an arm portion. Since the coaxial structure is provided, a current density between the conductive yarn 231 and the conductive yarn 233 is maximized, and an influence of noise from the outside of the sensor fiber can be reduced. Further, even when the sensor fibers 230 come in contact with the skin having high permittivity, or the sensor fibers 230 come in contact with each other as the sensor fibers 230 are wound on the arm portion as a multi-layer, hardly any variation in measurement value occurs.

Next, a manufacturing apparatus of the sensor fiber 230 will be described. The sensor fiber 230 shown in FIGS. 9 and 10 can be manufactured using so-called covering of winding a coating wire on an extended core wire.

Figure 11:
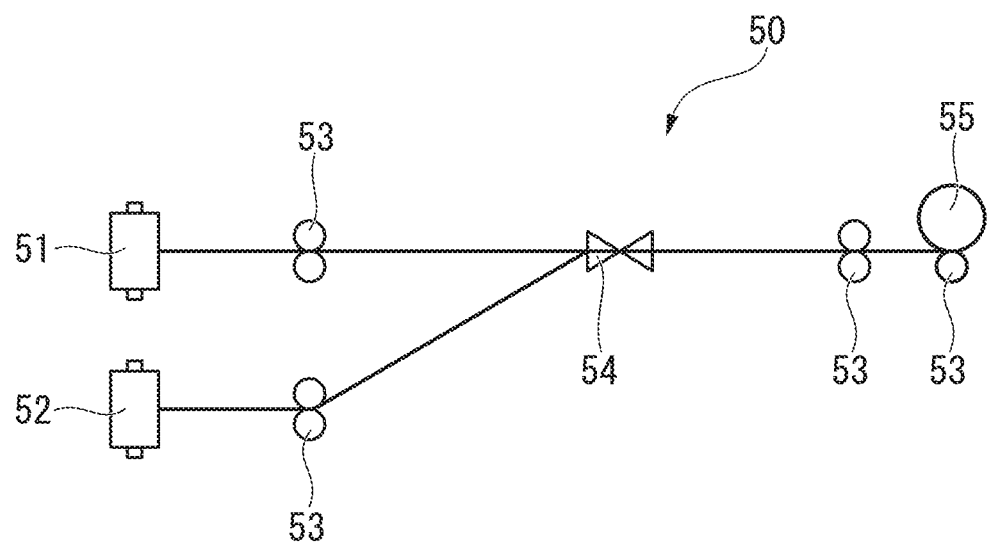
FIG. 11 is a schematic view showing an apparatus for manufacturing a sensor fiber.

FIG. 11 is a schematic view of a manufacturing apparatus 50 of the sensor fiber. As shown in FIG. 11, the manufacturing apparatus 50 of the sensor fiber has a first supply reel 51 configured to supply a core wire, a second supply reel 52 configured to supply a coated yarn, a plurality of feed rollers 53, a false twister 54, and a winding roller 55. The manufacturing apparatus 50 can arbitrarily change a pitch of a coating wire (a pitch of a yarn in a longitudinal direction) by adjusting the false twister 54.

Next, a method of manufacturing the sensor fiber 230 will be described.

First, the conductive yarn 231 (hereinafter, referred to as a first processed yarn) coated (covered) with the insulating cotton 232 is manufactured by setting the conductive yarn 231 (a conductive yarn group) as a core wire to the first supply reel 51 and setting the insulating cotton 232 as a coated yarn. The first processed yarn is wound by the winding roller 55.

The conductive yarn 233 coated with the insulating cotton 236 is manufactured using the same method.

Next, the first processed yarn on which the conductive yarn 233 is wound (hereinafter, referred to as a second processed yarn) is manufactured by setting the first processed yarn to the first supply reel 51 and setting the conductive yarn 233 to the second supply reel 52.

As such a manufacturing method is used, the sensor fiber 230 can be more easily manufactured. That is, as the covering is used, the sensor fiber 230 can be manufactured using a conventional manufacturing apparatus.

The method of manufacturing the sensor fiber 230 is not limited thereto, and for example, like braiding, the sensor fiber can be manufactured by weaving or the like the conductive yarn that is a core wire and the insulating cotton that is a coating wire.

Figure 12:
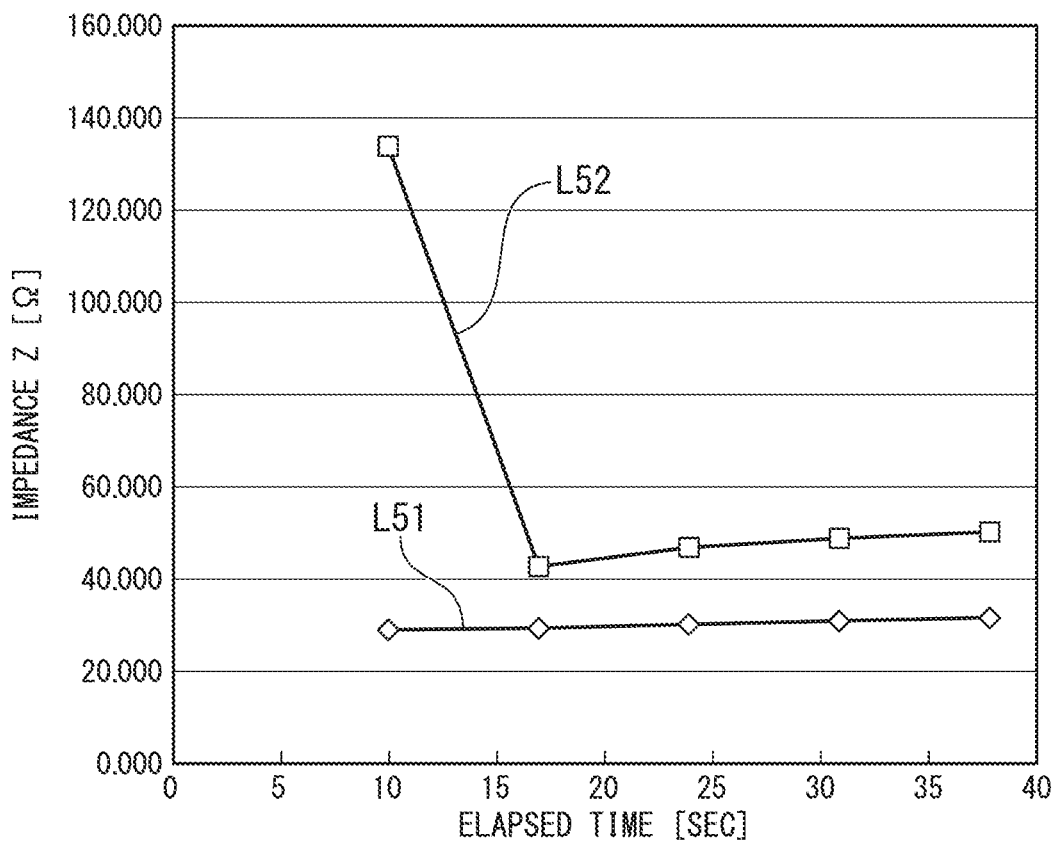
FIG. 12 is a graph showing variation with time in a measurement value of a magnitude Z of impedance in a state in which a saline solution or blood (pig blood) drops onto the sensor fiber in an experiment in relation to the embodiment.

FIG. 12 is a graph showing a variation with time in a measurement value of a magnitude Z of impedance in a state in which a saline solution or blood (pig blood) drips on the sensor fiber. A horizontal axis of the graph shown in FIG. 12 represents elapse of time from dripping, and a vertical axis represents impedance. A line L51 represents impedance in a state in which saline solution drops, and a line L52 represents impedance in a state in which blood drops.

In the example of FIG. 12, an alternating current signal of 75 kilohertz is input to the sensor fiber 230 (the conductive yarns 231 and 233).

While the impedance hardly changes during dripping of the saline solution, shown by the line L51, the impedance decreases immediately and then increases during dripping of blood, shown by the line L52.

Further, it is needless to say that the impedance is shown as an extremely high value before the saline solution or the blood drops onto the sensor fiber.

Figure 13:
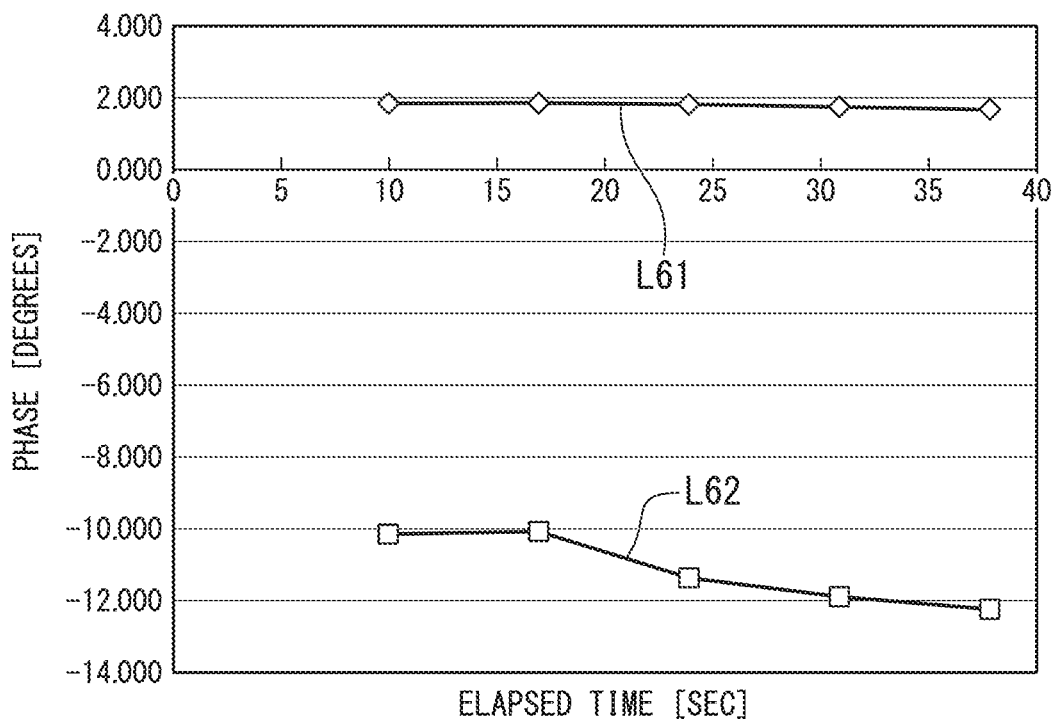
FIG. 13 is a graph showing a variation with time in a measurement value of a phase difference in a state in which a saline solution or blood (pig blood) drops onto the sensor fiber in the experiment in relation to the embodiment.

FIG. 13 is a graph showing a variation with time in a measurement value of a phase difference in a state in which a saline solution or blood (pig blood) drops onto the sensor fiber. The phase difference is a phase difference (a phase delay) of the alternating current signal flowing between the conductive yarns 231 and 233 with respect to the phase of the alternating current signal input to the conductive yarns 231 and 233.

A horizontal axis of the graph shown in FIG. 13 represents elapse of time after dropping, and a vertical axis represents a phase difference. A line L61 represents a phase difference in a state in which the saline solution drops, and a line L62 represents a phase difference in a state in which the blood drops. In the example of FIG. 12, an alternating current signal of 1 megahertz is input to the sensor fiber 230 (the conductive yarns 231 and 233).

A phase difference is larger in the state in which the blood shown by the line L62 drops than in the state in which the saline solution shown by the line L61 drops. In addition, while the phase difference hardly varies during dripping of the saline solution, the phase is delayed according to elapse of time during dripping of blood.

As shown in FIG. 12 or 13, a difference also occurs in a variation with time in the frequency characteristics in the saline solution and the blood. Here, a condition according to a variation of frequency characteristics according to elapse of time may be used in addition to or instead of a difference in frequency characteristics according to a difference in frequency as a detecting condition of the detection signal output unit 191.

It is thought that a difference in frequency characteristics between the saline solution and the blood described with reference to FIGS. 3 to 13 is caused due to a structure of red blood cells in the blood. More specifically, it is considered that the impedance or the phase difference is varied according to the frequency by a dielectric substance caused by a red blood cell membrane. For this reason, the detection device 100 can detect the blood distinctly from various liquids that do not include a structure such as a red blood cell membrane, for example, water, cola, or the like, without being limited to sweat. Accordingly, in the detection device 100, even when the patient has spilled a beverage such as water, cola, or the like, the possibility that removal of a needle is misdetected can be reduced.

Further, when the liquid drips onto the fiber sheet 200, an impedance ratio is decreased. The impedance ratio is a value obtained by dividing the impedance when the alternating current signal of a certain frequency is input to between the first conductive body 210 and the second conductive body 220 by the impedance when the alternating current signal of another frequency is input. Further, the impedance when the alternating current signal having a low frequency is input is divided by the impedance when the alternating current signal having a high frequency is input.

Figure 14:
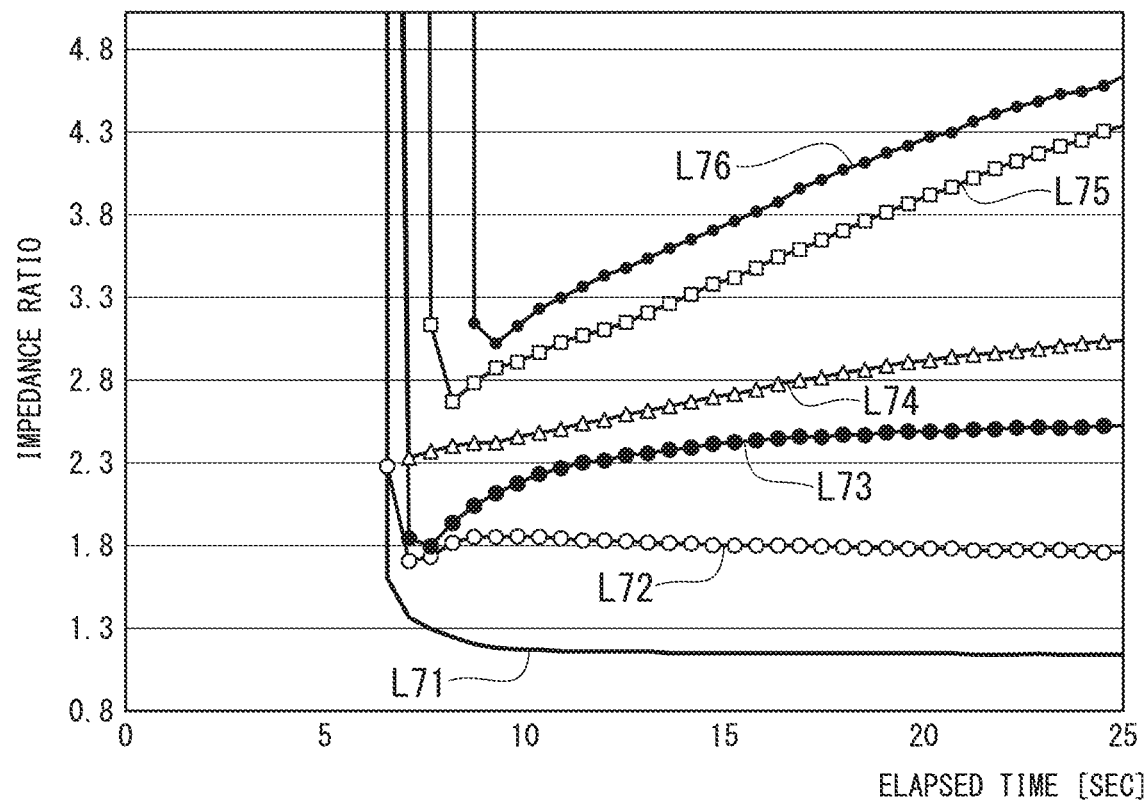
FIG. 14 is a view describing an example of a variation with time inane impedance ratio of blood and a physiological saline solution.

FIG. 14 is a view describing an example of a variation with time in an impedance ratio between the blood and the physiological saline solution. A horizontal axis of the graph shown in FIG. 14 represents elapse of time from dripping of a liquid, and a vertical axis represents an impedance ratio.

In the example of FIG. 14, during each sampling time, the alternating current signal of 5 megahertz and the alternating current signal of 10 kilohertz are input to between the first conductive body 210 and the second conductive body 220 and impedance thereof is measured. Then, the impedance ratio is obtained by dividing the impedance when the alternating current signal of 5 megahertz is input by the impedance when the alternating current signal of 10 kilohertz is input.

A line L71 represents an example of a variation with time in an impedance ratio when a physiological saline solution is dropped on the fiber sheet 200. Lines L72 to L76 represent examples of time changes of impedance ratios when blood having hematocrit (Ht) values of 20%, 30%, 43%, 41% and 44% is dropped onto the fiber sheet 200.

As shown in FIG. 14, while the impedance ratio is decreased even when the physiological saline solution (the line L71) drops or even when the blood (the lines L72 to L76) having each hematocrit values drops, since the impedance ratio of the blood (the lines L72 to L76) after dripping represents a value higher than that of the physiological saline solution (the line L71), it will be appreciated that the blood and the physiological saline solution (sweat) can be distinguished by simply determining a threshold of the impedance ratio when the time elapse more than five seconds after dripping. Further, after the impedance ratio is decreased, in the case of the physiological saline solution (the line L71), a low impedance ratio is maintained. In the case of the blood (the lines L72 to L76), the impedance ratio is temporarily decreased and then increased.

It is possible to detect that any liquid drips onto the fiber sheet 200, without being limited to blood, by detecting a decrease in impedance ratio. The detection device 100 can detect a leakage of liquid other than blood, for example, a transfusion liquid or the like, in addition to leakage of blood by detecting that the liquid drips onto the fiber sheet 200 and further determining whether the liquid is blood.

Further, a leakage of liquid can be detected by detecting a decrease in impedance, in addition to or instead of a decrease in impedance ratio.

Determining whether the liquid dripping onto the fiber sheet 200 is blood can be performed by, for example, determining whether a time derivative of the impedance ratio is a predetermined threshold or more. Specifically, when the liquid dripping onto the fiber sheet 200 is blood, the impedance ratio between the first conductive body 210 and the second conductive body 220 is decreased and then increased. An increase in impedance ratio can be detected by a value of the time derivative of the impedance ratio.

The detection signal output unit 191 calculates a time derivative of the impedance ratio, and determines whether the obtained time derivative of the impedance ratio is a predetermined threshold or more. When the time derivative of the impedance ratio is the predetermined threshold or more, the detection signal output unit 191 determines that the blood drips onto the fiber sheet 200. When the time derivative of the impedance ratio is less than the predetermined threshold, the detection signal output unit 191 determines that the liquid other than the blood drips onto the fiber sheet 200.

Next, an operation of the detection device 100 to detect that the blood drips onto the fiber sheet 200 and liquid other than the blood drips will be described with reference to FIGS. 15 and 16.

Figure 15:
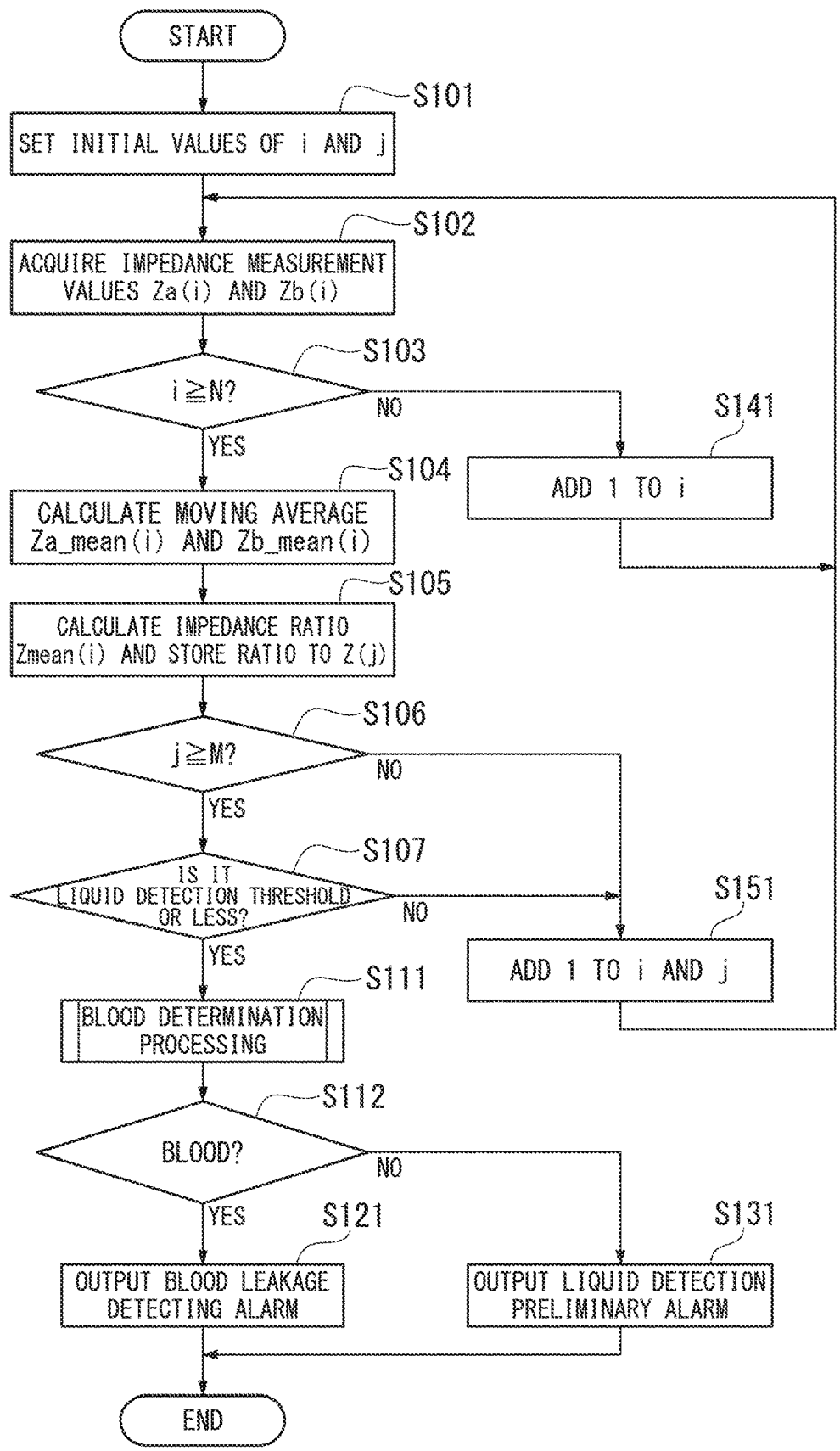
FIG. 15 is a flowchart showing an example of a processing sequence in which a detection device in the embodiment detects that blood has dripped onto the fiber sheet or a liquid other than blood has dripped thereon.

FIG. 15 is a flowchart showing an example of a processing sequence of causing the detection device 100 to detect that the blood drips onto the fiber sheet 200 or liquid other than the blood drips.

In the processing of FIG. 15, the detection signal output unit 191 sets an initial value of a variable i (i is a positive integer of i≥1) and an initial value of a variable j (step S101). Specifically, the detection signal output unit 191 has values of i=1 and j=1. Here, the variable i is a variable showing the number of times of sampling of measuring the impedance between the first conductive body 210 and the second conductive body 220 using the frequency characteristics acquisition unit 120. In addition, the variable j is a variable showing the number of times of calculating the impedance ratio on the basis of the impedance measurement value using the detection signal output unit 191.

Next, the frequency characteristics acquisition unit 120 acquires a value of impedance measured between the first conductive body 210 and the second conductive body 220 (step S102). Specifically, the alternating current signal output unit 110 inputs the alternating current signal having a predetermined first frequency and the alternating current signal having a second frequency (a predetermined frequency different from the first frequency) to between the first conductive body 210 and the second conductive body 220. Then, the frequency characteristics acquisition unit 120 measures the impedance between the first conductive body 210 and the second conductive body 220 when the alternating current signal having the first frequency is input and when the alternating current signal having the second frequency is input. Further, the first frequency is lower than the second frequency.

Further, hereinafter, the impedance is measured a plurality of times when the detection device 100 inputs the first frequency and when the second frequency is input in step S102. Although the detection device 100 can detect the blood and the liquid other than the blood even by measurement of one time, misdetection due to noise can be reduced by measuring the blood and the liquid a plurality of times. Hereinafter, the impedance measurement value when the alternating current signal output unit 110 inputs the alternating current signal having the first frequency at $i^{th}$ sampling is expressed as Za(i), and the impedance measurement value when the alternating current signal having the second frequency is input is expressed as Zb(i). The frequency characteristics acquisition unit 120 stores the acquired impedance measurement values Za(i) and Zb(i) to the storage unit 180.

Next, the detection signal output unit 191 determines whether i≥N (step S103). Here, a constant N (N is a positive integer of N≥1) is a constant that is preset as a data number used to calculate a moving average of the impedance measurement value using the detection signal output unit 191.

When it is determined that i<N (step S103: NO), the detection signal output unit 191 adds 1 to a value of i (i:=i+1) (step S141).

After step S141, the process returns to step S102.

When it is determined that i≥N (step S103: YES), the detection signal output unit 191 calculates a moving average of the impedance measurement value obtained in step S102 (step S104). Specifically, the detection signal output unit 191 calculates a moving average Za_mean(i) of the latest N values (Za(i−N+1) to Za(i)) of the impedance measurement values in inputting the alternating current signal having the first frequency acquired by the frequency characteristics acquisition unit 120. In addition, the detection signal output unit 191 calculates a moving average Zb_mean(i) of the latest N values (Zb(i−N+1) to Zb(i)) of the impedance measurement values in inputting the alternating current signal having the second frequency acquired by the frequency characteristics acquisition unit 120. The detection signal output unit 191 stores the calculated moving averages Za_mean(i) and Zb_mean(i) to the storage unit 180.

Further, the storage unit 180 may not store all the impedance measurement values acquired by the frequency characteristics acquisition unit 120 in step S102. The storage unit 180 may store the latest N values (Za(i−N+1) to Za(i)) of the impedance measurement values in inputting the alternating current signal having the first frequency and the latest N values (Zb(i−N+1) to Zb(i)) of the impedance measurement values in inputting the alternating current signal having the second frequency.

In addition, the storage unit 180 may not store all the moving averages calculated by the detection signal output unit 191 in step S104. The storage unit 180 may store the latest one Za_mean(i) of the moving averages of the impedance measurement values in inputting the alternating current signal having the first frequency and the latest one Zb_mean(i) of the moving averages of the impedance measurement values in inputting the alternating current signal having the second frequency.

Next, the detection signal output unit 191 calculates an impedance ratio Zmean(i) on the basis of the moving averages Za_mean(i) and Zb_mean(i) of the impedance measurement values obtained in step S104 to store the ratio to Z(j) (step S105). Specifically, the detection signal output unit 191 divides the moving average Za_mean(i) of the impedance measurement values by the moving average Zb_mean(i) of the impedance measurement value to calculate an impedance ratio Zmean(i). Then, the detection signal output unit 191 stores the calculated impedance ratio Zmean(i) to the storage unit 180 as the impedance ratio Z(j).

Next, the detection signal output unit 191 determines whether j≥M (step S106). Here, a constant M (M is a positive integer of M≥2) is a constant that is previously set as a data number used to determine whether liquid drops on the fiber sheet 200 using the detection signal output unit 191.

Further, the storage unit 180 stores at least the latest M values (Z(j−M+1) to Z(j)) of the impedance ratios calculated by the detection signal output unit 191 in step S105. The storage unit 180 may store all the impedance ratios calculated by the detection signal output unit 191 to (Z(1) to Z(j)) in step S105.

When it is determined that j<M (step S106: NO), the detection signal output unit 191 adds 1 to values of i and j (i: =i+1, j: =j+1) (step S151).

After step S151, the process returns to step S102.

When it is determined that j≥M (step S106: YES), the detection signal output unit 191 determines whether all the latest M impedance ratios obtained in step S106 are equal to or fewer than a liquid-detecting threshold (step S107). That is, the detection signal output unit 191 determines that Z(j−M+1) liquid detection-determining threshold . . . , and, Z(j) liquid detection-determining threshold (step S107).

When it is determined that any one of the latest M impedance ratios is larger than the liquid-detecting threshold (step S107: NO), the process moves to step S151.

When it is determined that all the latest M impedance ratios are the liquid-detecting threshold or less (step S107: YES), the detection signal output unit 191 performs blood-determining processing (step S111). The blood-determining processing is processing of performing determining whether the liquid dripping onto the fiber sheet 200 is blood.

Figure 16:
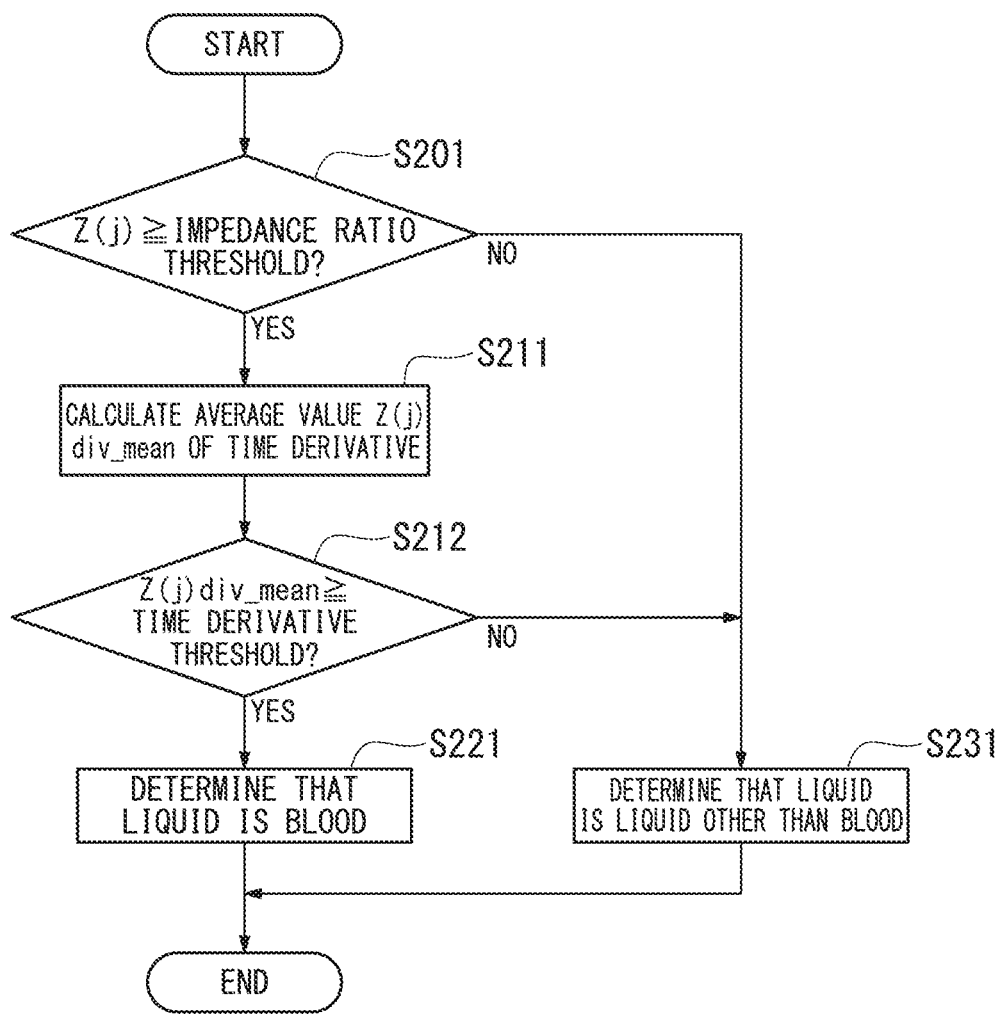
FIG. 16 is a flowchart showing a sequence in which a detection signal output unit in the embodiment performs blood-determining processing.

FIG. 16 is a flowchart showing a sequence of performing the blood-determining processing using the detection signal output unit 191. The detection signal output unit 191 performs processing of FIG. 16 in step S111 of FIG. 15.

In processing of FIG. 16, the detection signal output unit 191 determines whether the latest impedance ratio Z(j) obtained in step S105 of FIG. 15 is a predetermined impedance ratio threshold or more (step S201).

When it is determined that the latest impedance ratio Z(j) is the impedance ratio threshold or more (step S201: YES), the detection signal output unit 191 calculates an average value Z(j)div_mean of a time derivative from the latest M impedance ratios Z(j−M+1) to Z(j) obtained in step S105 of FIG. 15 (step S211).

Specifically, the detection signal output unit 191 calculates a time derivative of the impedance ratio Z(j−M+1) by dividing a difference obtained by subtracting the impedance ratio Z(j−M+1) from the impedance ratio Z(j−M+2) by a time interval (a sampling period) of impedance measurement in step S102 of FIG. 15. In this way, the detection signal output unit 191 performs processing of calculating a time derivative of the impedance ratio Z(j−M+k) by dividing a difference obtained by subtracting the impedance ratio Z(j−M+k) from the impedance ratio Z(j−M+k+1) by a time interval of impedance measurement in step S102 of FIG. 15 for all positive integers k of 1≤k≤M−1.

Then, the detection signal output unit 191 calculates an average value of all the obtained time derivatives (a time derivative of (impedance ratio Z(j−M+1) to a time derivative of an impedance ratio Z(j−1)) to obtain an average value Z(j)div_mean of the time derivatives.

Then, the detection signal output unit 191 determines whether the time derivative Z(j)div_mean of the impedance ratio obtained in step S211 is a predetermined time derivative threshold or more (step S212).

When it is determined that the time derivative Z(j)div_mean of the impedance ratio is the time derivative threshold or more (step S212: YES), the detection signal output unit 191 determines that the liquid dripping onto the fiber sheet 200 is blood (step S221).

After step S221, processing of FIG. 16 is terminated, and the process returns to the processing of FIG. 15.

When it is determined that, in step S221, the time derivative Z(j)div_mean of the impedance ratio is less than the time derivative threshold (step S212: NO), the detection signal output unit 191 determines that the liquid dripping onto the fiber sheet 200 is a liquid other than the blood (step S231).

After step S231, the processing of FIG. 16 is terminated, and the process returns to the processing of FIG. 15.

In step S201, when it is determined that the impedance ratio Z(j) is less than the impedance ratio threshold (step S201: NO), the process moves to step S231.

Returning to the processing of FIG. 15, when the blood-determining processing in step S111 is terminated, the detection signal output unit 191 performs conditional branching on the basis of the determination result in step S111 (step S112). Specifically, the detection signal output unit 191 performs conditional branching based on whether or not it is determined that the liquid dripping onto the fiber sheet 200 is blood.

When it is determined that the liquid dripping onto the fiber sheet 200 is blood (step S112: YES), the alarm output unit 130 outputs a blood leakage-detecting alarm (step S121). The blood leakage-detecting alarm is an alarm showing that the blood drips onto the fiber sheet 200.

In step S121, the detection signal output unit 191 outputs a detection signal showing that blood drips onto the fiber sheet 200 to the alarm output unit 130. Then, the alarm output unit 130 outputs a blood leakage-detecting alarm according to the detection signal from the detection signal output unit 191.

After step S121, the processing of FIG. 15 is terminated.

When it is determined that the liquid dripping onto the fiber sheet 200 is the liquid other than the blood (step S122: NO), the alarm output unit 130 outputs a liquid detection preliminary alarm (step S131). The liquid detection preliminary alarm is an alarm showing that the liquid other than the blood drips onto the fiber sheet 200.

In step S122, the detection signal output unit 191 outputs the detection signal indicating that the liquid other than the blood drips onto the fiber sheet 200 to the alarm output unit 130. Then, the alarm output unit 130 outputs a liquid detection preliminary alarm according to the detection signal from the detection signal output unit 191.

After step S131, the processing of FIG. 15 is terminated.

Further, the detection device 100 may repeatedly perform the processing of FIG. 15. Accordingly, the detection device 100 can detect that the blood drips when it is detected that the liquid other than the blood drips onto the fiber sheet 200 and then the blood drips onto the fiber sheet 200.

Further, the detection device 100 or a person may distinguish between blood and the liquid other than the blood using a Cole-Cole trajectory. For example, the detection signal output unit 191 may perform the determination of whether the liquid dripping onto the fiber sheet 200 is blood in step S201 of FIG. 16 using the Cole-Cole trajectory instead of the processing of determining through comparison of the average value of the impedance ratio and the threshold. Processing of distinguishing between blood and the liquid other than the blood using the Cole-Cole trajectory will be described with reference to FIGS. 17 and 18.

Figure 17:
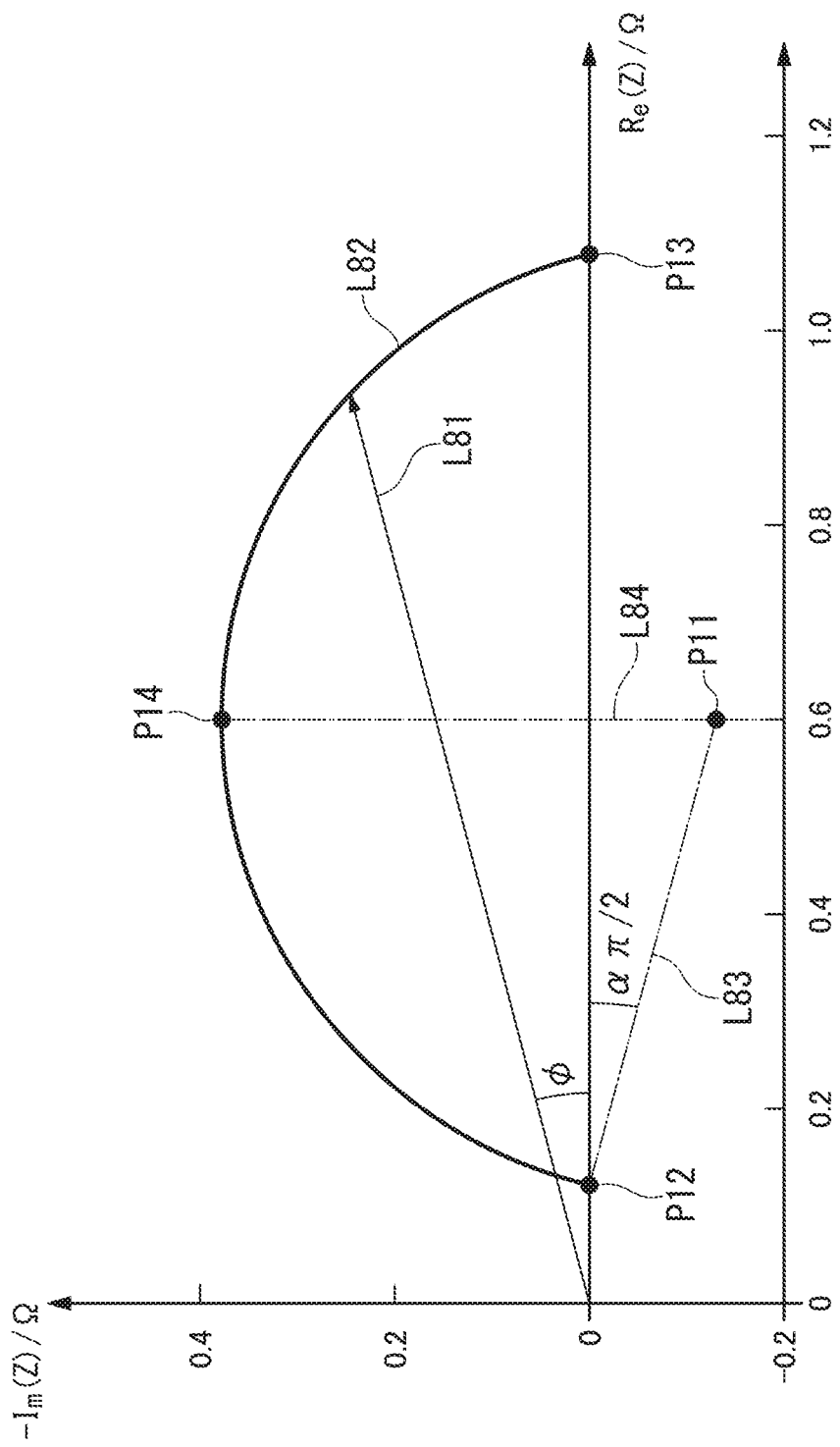
FIG. 17 is a view describing an example of a Cole-Cole trajectory obtained by measurement of impedance.
Figure 18:
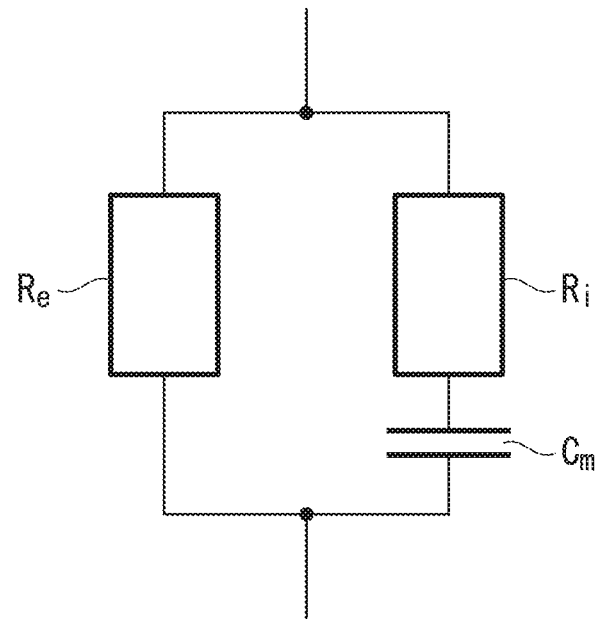
FIG. 18 is a view describing an equivalent circuit model of simulating an impedance of liquid having a membrane.

Further, in the description of FIG. 17 and the description of FIG. 18, the impedance is represented by a complex number in which a resistance is included in a real part and a reactance is included in an imaginary part.

FIG. 17 is a view describing an example of the Cole-Cole trajectory obtained by measuring the impedance. A horizontal axis of a graph shown in FIG. 17 represents a real part of the impedance, and a vertical axis represents an imaginary part of the impedance. Further, in FIG. 17, a standardized impedance value (a value obtained by dividing the impedance value by a predetermined magnitude (a real number)) is used. However, the Cole-Cole trajectory may be obtained on the basis of the impedance value without standardizing the impedance value.

A line L81 in FIG. 17 represents a measurement value of the impedance as a vector. An angle φ represents a phase difference between the input signal and the impedance measurement value. In this way, the impedance measurement values can be plotted as the graph on the basis of the magnitude of the impedance (or a magnitude of a real part of the impedance=a resistance) and the phase difference.

In addition, a line L82 represents a Cole-Cole trajectory. Here, the Cole-Cole trajectory has a shape of a portion of an arc.

The Cole-Cole trajectory is obtained from the impedance measurement value. Specifically, the Cole-Cole trajectory is obtained by measuring a magnitude of the impedance (or a resistance) and the phase difference (the angle φ) a plurality of times by varying a frequency of the input signal to the fiber sheet 200 and approximating the obtained measurement values to the portion of the arc (performing curve fitting). As a method of obtaining the Cole-Cole trajectory from the impedance measurement value (a method of performing curve fitting), for example, a known approximate technique such as a least squares method or the like may be used. In order to obtain the Cole-Cole trajectory, the alternating current signal output unit 110 inputs at least three alternating current signals having different frequencies to between the first conductive body 210 and the second conductive body 220, and the frequency characteristics acquisition unit 120 acquires frequency characteristics between the first conductive body 210 and the second conductive body 220 with each of the alternating current signals that were input.

A point P11 shows a center of an arc showing the Cole-Cole trajectory (a center of a circle that includes the arc as a portion of a circumference). Points P12 and P13 are intersections of the Cole-Cole trajectory and the horizontal axis. In the two intersections, an intersection having a small real part of the impedance is the point P12, and an intersection having a large real part of the impedance is the point P13. In addition, a point P14 is a center of an arc showing the Cole-Cole trajectory. Accordingly, a line segment (a line L84) connecting the point P11 and the point P14 bisects an angle formed between a line segment connecting the point P11 and the point P12 (a line L83) and a line segment connecting the point P11 and the point P13.

An angle απ/2 is an angle formed between the line segment connecting the point P12 and the point P11 (the line L83) and a horizontal axis.

The Cole-Cole trajectory is shown as Equation (1).

[Math. 1]

$$Z(f) = R_\infty + \frac{R_0 - R_\infty}{1 + \left(\frac{jf}{f_c}\right)^{(1-\alpha)}} \quad (1)$$

Here, Z(f) represents impedance when a signal having a frequency f is input. $R_\infty$ represents a resistance (a real part of the impedance) when a signal having an infinite frequency is input. Since $R_\infty$ cannot be measured in actuality, $R_\infty$ is read from the intersection of the Cole-Cole trajectory and the horizontal axis (an intersection having a small resistance in two intersections). In the example of FIG. 17, a resistance represented by the point P12 is used as $R_\infty$.

$R_0$ represents a resistance when a signal having a frequency of 0, i.e., a direct current signal is input. $R_0$ may be measured in actuality or may be read from the intersection of the Cole-Cole trajectory and the horizontal axis (the intersection having a large resistance in the two intersections). In the example of FIG. 17, the resistance represented by the point P13 may be used as $R_\infty$.

In addition, $f_c$ represents a center frequency corresponding to the point P14 (an input frequency at which the impedance value represented by the point P14 is obtained).

In addition, j represents an imaginary unit. α represents a coefficient of a value obtained by dividing the angle απ/2 by π/2.

FIG. 18 is a view describing an equivalent circuit model simulating an impedance of a liquid having a membrane.

$R_i$ represents a resistance by a substance having a membrane included in a liquid. For example, when the liquid is blood, a red blood cell corresponds to a substance having a membrane. $C_m$ represents a capacitance by a substance having a membrane included in a liquid. Further, the capacitance can be regarded as the reactance in FIG. 17. $R_e$ represents a resistance by a substance other than the substance having the membrane included in the liquid. For example, when the liquid is blood, blood plasma corresponds to the substance other than the substance having the membrane.

The equivalent circuit model is an electric circuit showing impedance equal to or substantially equal to impedance of a modeling object (here, a liquid having a membrane). As an element that constitutes the equivalent circuit, one or more of an electric resistance (a register), a capacitor (a capacitor) and a coil (a reactor) is used. For example, the equivalent circuit model shown in FIG. 18 is configured using an electric resistance of a resistance $R_i$, a capacitor of a capacitance $C_m$ and an electric resistance of a resistance $R_e$.

In addition, the resistance, the capacitance or the impedance of the element that configures the equivalent circuit model are referred to as circuit parameters. For example, in the equivalent circuit model shown in FIG. 18, each of the resistance $R_i$, the capacitance $C_m$ and the resistance $R_e$ corresponds to the circuit parameter.

When a value of the circuit parameter is varied, the impedance of the equivalent circuit model is varied. As described below, the detection signal output unit 191 or a person calculates a circuit parameter value (a value of the circuit parameter) at which the impedance of the equivalent circuit model is equal to or substantially equal to the impedance measurement value of the modeling object.

Further, FIG. 18 is an example of the equivalent circuit model, and the same method can also be applied to the equivalent circuit model having a more complicated structure. For example, instead of the single dispersion model shown in FIG. 18, the detection signal output unit 191 or a person may use a two-dispersion model or a three-dispersion model.

The single dispersion model is a model configured by an electric circuit in which one series connection of the electric resistance and the capacitor (or the coil) is parallelly connected to the electric resistance. The two-dispersion model is a model configured by an electric circuit in which two series connection of the electric resistance and the capacitor (or the coil) is parallelly connected to the electric resistance. The three-dispersion model is a model configured by an electric circuit in which three series connection of the electric resistance and the capacitor (or the coil) is parallelly connected to the electric resistance.

When the modeling object is blood, since the red blood cell has a single membrane structure, the impedance of the modeling object can be simulated using the single dispersion model.

When the modeling object is an animal cell, the animal cell is a double membrane structure since a cell membrane has a nucleus therein. In this way, when a target of the modeling has a double membrane structure, the impedance of the modeling object can be simulated using the two-dispersion model. In addition, when the target of the modeling has a triple membrane structure, the impedance can be simulated using the three-dispersion model.

The detection signal output unit 191 or a person obtains a value of the model parameter (values of a resistance $R_i$, a capacitance $C_m$ and a resistance $R_e$) on the basis of the Cole-Cole trajectory obtained from the impedance measurement values.

Specifically, the values of the resistance $R_i$, the capacitance $C_m$ and the resistance $R_e$ can be obtained using a resistance $R_0$, a resistance $R_\infty$ and a center frequency $f_c$ obtained from the Cole-Cole trajectory.

First, the resistance $R_e$ is obtained as shown by Equation (2).

[Math. 2]

$$R_e = R_0 \quad (2)$$

In addition, a resistance $R_\infty$ is expressed as shown by Equation (3).

[Math. 3]

$$R_\infty = \frac{R_e R_i}{R_e + R_i} \quad (3)$$

Equation (2) is substituted for Equation (3) to obtain Equation (4).

[Math. 4]

$$R_i = \frac{R_\infty R_0}{R_0 - R_\infty} \quad (4)$$

In addition, a center frequency $f_c$ is expressed as shown by Equation (5).

[Math. 5]

$$f_c = \frac{1}{2\pi C_m (R_e + R_i)} \quad (5)$$

Equation (5) is transformed to obtain Equation (6).

[Math. 6]

$$C_m = \frac{1}{2\pi f_c (R_e + R_i)} \quad (6)$$

The detection signal output unit 191 or a person calculates the impedance $R_e$, the impedance $R_i$ and the capacitance $C_m$ using Equations (1), (3) and (6).

Here, the values of the resistance the capacitance $C_m$ and the resistance $R_e$ are different according to the membrane included in the liquid or a tissue structure. Here, a kind of liquid can be estimated from these values.

For example, the detection signal output unit 191 or a person determines whether the liquid dripping onto the fiber sheet 200 (the liquid that is a measurement target) is blood by comparing the capacitance $C_m$ and a predetermined threshold (a blood-detecting threshold). When the capacitance $C_m$ is larger than the blood-detecting threshold, the detection signal output unit 191 or a person determines that the liquid dripping onto the fiber sheet 200 is blood. When the capacitance $C_m$ is a blood-detecting threshold or less, the detection signal output unit 191 or a person determines that the liquid dripping onto the fiber sheet 200 is liquid other than the blood.

Further, the detection signal output unit 191 or a person may obtain values of all the model parameters included in the equivalent circuit model or may obtain only values of some of the model parameters.

For example, in the example of FIG. 18, the detection signal output unit 191 or a person may determine whether the liquid dripping onto the fiber sheet 200 is blood by calculating the impedance $R_e$, the impedance $R_i$ and the capacitance $C_m$, and comparing the values with the threshold. Alternatively, the detection signal output unit 191 or a person may determine whether the liquid dripping onto the fiber sheet 200 is blood by calculating only the capacitance $C_m$ among the impedance $R_e$, the impedance $R_i$ and the capacitance $C_m$, and comparing the capacitance $C_m$ and the threshold.

Further, as a method of inputting at least three alternating current signals having different frequencies to obtain the Cole-Cole trajectory, a pulse signal or a step signal may be input between the conductive bodies. In this case, as the impedance measurement value is transformed through Fourier transform, the impedance measurement value of each of the different input frequencies is obtained.

Accordingly, a time required for inputting the signal to between the conductive bodies is reduced more than the case in which the alternating current signal is input to between the conductive bodies while varying the frequency.

Alternatively, as a method of inputting at least three alternating current signals having different frequencies to obtain the Cole-Cole trajectory, a signal in which three or more sine waves having different frequencies overlap may be input to between the conductive bodies. Even in this case, as the impedance measurement value is transformed through Fourier transform, the impedance measurement value of each of the different input frequencies is obtained.

Accordingly, a time required for inputting the signal to between the conductive bodies is reduced more than the case in which the alternating current signal is input to between the conductive bodies while varying the frequency.

As described above, the alternating current signal output unit 110 performs an alternating current signal inputting step of inputting at least three alternating current signals having different frequencies to between the plurality of conductive bodies formed on the fiber sheet. Alternatively, a person may perform the alternating current signal inputting step by connecting the alternating current signal output apparatus (the alternating current power supply) having a variable frequency to between the plurality of conductive bodies.

Then, the frequency characteristics acquisition unit 120 performs an impedance measurement value acquisition step of acquiring a value of impedance measured between the conductive bodies with each of the alternating current signals input in the alternating current signal inputting step. Alternatively, a person may perform the impedance measurement value acquisition step using an impedance measurement apparatus (for example, an oscilloscope).

Then, the detection signal output unit 191 performs a Cole-Cole trajectory acquisition step of obtaining a Cole-Cole trajectory that approximates the impedance measurement value obtained in the impedance measurement value acquisition step at a portion of an arc. Alternatively, a person may perform the Cole-Cole trajectory acquisition step.

Then, the detection signal output unit 191 performs a capacitance acquisition step of obtaining a capacitance in a predetermined equivalent circuit model simulating an impedance of a liquid having a membrane on the basis of the Cole-Cole trajectory. Alternatively, a person may perform the capacitance acquisition step.

Then, the detection signal output unit 191 performs a liquid type estimation step of estimating a kind of liquid on the basis of the obtained capacitance. Alternatively, a person may perform the liquid type estimation step.

Accordingly, the detection signal output unit 191 or a person can accurately perform determination whether blood drips onto the fiber sheet 200.

Further, when the detection signal output unit 191 determines that the blood drips onto the fiber sheet 200 in the liquid type estimation step, the alarm output unit 130 may output a blood leakage-detecting alarm.

Further, the detection signal output unit 191 or a person may determine whether the liquid dripping on the fiber sheet 200 is a predetermined liquid other than the blood. For example, when milk drips onto the fiber sheet 200, a capacitance $C_m$ may be smaller than the case of the blood. Here, the detection signal output unit 191 or a person compares a threshold of a value smaller than the blood-detecting threshold that is a previously determined as a milk-detecting threshold and a capacitance $C_m$, in addition to comparison of the blood-detecting threshold and the capacitance $C_m$. When the capacitance $C_m$ is larger than the milk-detecting threshold and smaller than the blood-detecting threshold, the detection signal output unit 191 or a person determines that the liquid dripping onto the fiber sheet 200 is milk.

As described above, when the alternating current signal output unit 110 inputs a plurality of alternating current signals having different frequencies to between the conductive bodies (between the first conductive body 210 and the second conductive body 220) and the frequency characteristics acquired by the frequency characteristics acquisition unit 120 show a predetermined difference according to a difference of the frequency of the alternating current signal from the alternating current signal output unit 110, and the alternating current signal output unit 110 inputs the alternating current signal to between the conductive bodies a plurality of times and the frequency characteristics acquired by the frequency characteristics acquisition unit 120 show a predetermined variation according to elapse of time of an input of the alternating current signal from the alternating current signal output unit 110, the detection signal output unit 191 outputs a detection signal (a blood leakage-detecting alarm).

In this way, as the detection signal output unit 191 determines whether the detection signal is output on the basis of both the difference of the frequency characteristics between the conductive bodies due to the difference in frequency of the alternating current signal input to between the conductive bodies and a variation in the specific frequency between the conductive bodies due to elapse of time, it can be accurately determined whether the liquid dripping onto the fiber sheet is a predetermined liquid (for example, blood), and the possibility that a detection signal is incorrectly output can be reduced.

In addition, the detection signal output unit 191 or a person obtains the Cole-Cole trajectory that approximates the impedance measurement value between the conductive bodies (between the first conductive body 210 and the second conductive body 220) at a portion of an arc. Then, the detection signal output unit 191 or a person obtains a capacitance of a predetermined equivalent circuit model simulating an impedance of a liquid having a membrane on the basis of the Cole-Cole trajectory, and estimates a kind of the liquid from the obtained capacitance.

In this way, as the impedance of the liquid dripping onto the fiber sheet 200 is simulated through modeling to obtain a capacitance, the detection signal output unit 191 or a person can accurately perform determination of whether the liquid dripping onto the fiber sheet 200 is a predetermined liquid (for example, blood).

Further, the detection device 100 or a person may discriminate the blood and the liquid other than the blood on the basis of an inclination of a straight line that approximates a relationship between the frequency of the input signal and the impedance measurement value. For example, the detection signal output unit 191 may discriminate the blood and the liquid other than the blood on the basis of the inclination of the straight line, instead of processing of determining whether the liquid dripping onto the fiber sheet 200 is blood in step S201 of FIG. 16 through comparison of the average value of the impedance ratio and the threshold. Processing of discriminating the blood and the liquid other than the blood on the basis of the inclination of the straight line will be described with reference to FIG. 19.

Figure 19:
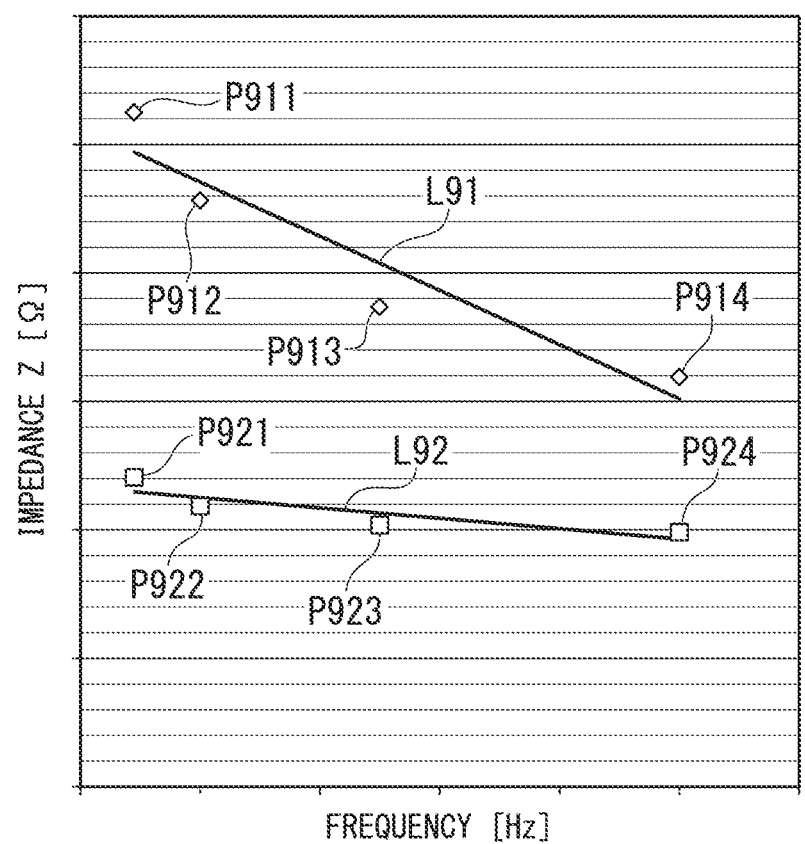
FIG. 19 is a view describing an example of a straight line approximating a relationship between a frequency and an impedance measurement value of an input signal.

FIG. 19 is a view describing an example of straight lines that approximate a relationship between the frequency of the input signal and the impedance measurement value in a certain frequency band. A horizontal axis of a graph in FIG. 19 represents the frequency of the input signal (an input frequency), and a vertical axis represents the impedance (a magnitude of the impedance).

A line L91 shows an example of a straight line that approximates a relationship between a frequency of an input signal with respect to blood and an impedance measurement value. Specifically, points P911, P912, P913 and P914 show relationships between the input frequencies and the impedance at the frequencies thereof when the alternating current signals are input to the blood. The line L91 is a line obtained by linearly approximating the points P911, P912, P913 and P914.

In addition, a line L92 shows an example of a straight line that approximates a relationship between a frequency of an input signal with respect to a saline solution and an impedance measurement value. Specifically, points P921, P922, P923 and P924 show relationships between the input frequencies and the impedance at the frequencies thereof when the alternating current signals are input to the saline solution. The line L92 is a line obtained by linearly approximating the points P921, P922, P923 and P924.

As exemplarily shown by the line L91, in the case of the blood, an inclination of an approximate straight line has a negative value. That is, the blood shows the impedance that is reduced as the input frequency is increased, and accordingly, the approximate straight line in the case of the blood is inclined rightward and downward. On the other hand, as exemplarily shown by the line L92, a magnitude of the inclination of the approximate straight line is smaller in the case of the saline solution than in the case of the blood. That is, the magnitude of the variation in impedance with respect to the variation in input frequency is reduced in the case of the saline solution, and accordingly, the approximate straight line in the case of the saline solution is closer to a horizontal line (more parallel to the horizontal axis) than in the case of the blood.

Here, the detection device 100 or a person discriminates the blood and the liquid other than the blood on the basis of the inclination of the straight line that approximates the relation between the frequency of the input signal and the impedance measurement value.

For example, the storage unit 180 of the detection device 100 previously stores a threshold of the inclination of the approximate straight line as a constant of a negative real number. Then, the detection signal output unit 191 of the detection device 100 obtains an inclination of a line that approximates a relationship between the frequency of the input signal to a measurement target and the impedance measurement value to a straight line. As a straight line approximation method, for example, while the least squares method may be used, there is no limitation thereto. In addition, the approximate equation is not limited to a primary function, and curve approximation by a multi-dimensional function, an exponential function, a logarithmic function, a logistic curve, and so on, may be used. Then, the detection signal output unit 191 compares the obtained inclination and the threshold and determines that the blood is detected when the inclination is smaller than the threshold (i.e., a magnitude of the inclination is larger than a magnitude of the threshold). The detection signal output unit 191 determines that the blood is not detected when the inclination is larger than the threshold (i.e., the magnitude of the inclination is equal to the magnitude of the threshold or less).

Further, for example, the storage unit 180 stores a value of the threshold as $-0.000001$ ($-1 \times 10^{-6}$). Then, when the obtained inclination is $-0.000004$ ($-4 \times 10^{-6}$), the detection signal output unit 191 outputs a detection signal showing that the blood is detected. That is, the detection signal output unit 191 determines that the blood is detected.

When the obtained inclination is $-0.0000008$ ($-8 \times 10^{-7}$), the detection signal output unit 191 controls output of the detection signal. That is, the detection signal output unit 191 determines that the blood is not detected.

In this way, the detection signal output unit 191 can obtain an inclination of a straight line that approximates a relationship between a frequency of an input signal and an impedance measurement value, and determine whether a predetermined liquid such as blood or the like is detected through relatively simple processing of comparing the obtained inclination and the threshold. In this regard, a load of the detection signal output unit 191 can be reduced.

Further, detection and determination of blood or the like may be performed using a time change such as an inclination or the like of an approximate straight line or an approximate curve in steps S211 to S212 of FIG. 16.

Next, a detailed structure of the bandage-shaped fiber sheet 200 having the first conductive yarn 231 functioning as the first conductive body 210 and the second conductive yarn 233 functioning as the second conductive body 220 will be described with reference to FIG. 20.

For example, the bandage-shaped fiber sheet 200 is used while being wrapped on a blood leakage observation target area such as an arm or the like to which is punctured with a needle during artificial dialysis. Here, the fiber sheet 200 can be cut by an arbitrary length, and the configuration in FIG. 1 may be provided as the two conductive yarns 231 and 233 are connected to the alternating current signal output unit 110 in one of end portions of the conductive yarns 231 and 233. Accordingly, the detection device 100 can detect a blood leakage as described above.

Figure 20:
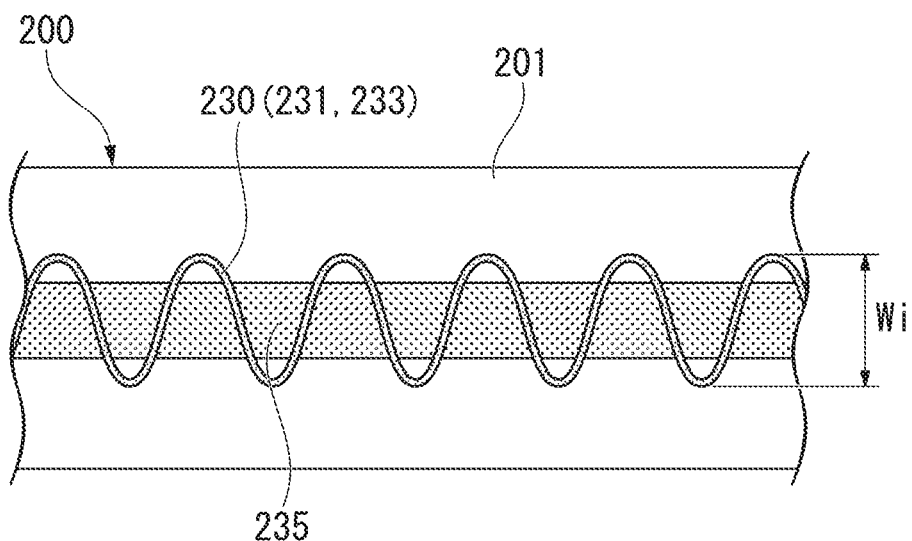
FIG. 20 is a structural view showing a schematic structure of a fiber sheet in the embodiment.

As shown in FIG. 20, the fiber sheet 200 is configured as the sensor fiber 230 meanders in a waveform to be woven (sewed) to an insulating fiber sheet main body 201 having absorbency.

As the two conductive yarns 231 and 233 are connected to the alternating current signal output unit 110 at one of the end portions of the sensor fiber 230, the configuration in FIG. 1 may be provided. Accordingly, the detection device 100 can detect the blood leakage as described above. In particular, as the sensor fiber 230 is disposed to be meandered, the detection device 100 can detect permeation of a liquid such as a blood leakage or the like at various portions of the fiber sheet 200.

As the two conductive yarns 231 and 233 use the sensor fibers 230 disposed not to contact with each other by the insulating cotton 232, the single sensor fiber 230 can be woven or sewed to the fiber sheet main body 201 to configure the fiber sheet 200.

Accordingly, the two conductive bodies can be disposed at a relatively small interval, and when the liquid permeates into the fiber sheet 200, detection accuracy of the detection signal output unit 191 can be increased.

Moreover, the fiber sheet 200 can be more simply fabricated than in the case in which the two conductive bodies (the conductive yarns 231 and 233) can be woven or sewed to the bandage, the fiber sheet, or the like, not to contact with each other, i.e., at a relatively small interval. Accordingly, manufacturing cost of the fiber sheet 200 can be reduced.

Next, a method of manufacturing the bandage-shaped fiber sheet 200 including the sensor fiber 230 will be described.

The fiber sheet 200 in which the sensor fiber 230 is woven can be manufactured with the following three patterns.

(Pattern A)

The fiber sheet 200 (the bandage) of a pattern A has (1) a warp yarn, (2) an elastic yarn, (3) a weft yarn, and (4) a sensor fiber as components.

Next, a method of manufacturing the fiber sheet 200 of the pattern A will be described. First, a yarn having an elastic property (for example, a covering yarn in which polyurethane is used as a core material) is used as a warp yarn to form a stitch, and a weft yarn is woven while inserting an elastic yarn (for example, a covering yarn in which polyurethane is used as a core material) to form the fiber sheet main body 201 (an elastic bandage) that becomes a base cloth. The sensor fiber is inserted and woven to the fiber sheet main body 201 to form the fiber sheet 200 of the pattern A.

(Pattern B)

The fiber sheet 200 of a pattern B has (1) a warp yarn, (2) an elastic yarn, (3) a weft yarn, and (4) a sensor fiber as components. The fiber sheet 200 of the pattern B has the same configuration as the fiber sheet 200 of the pattern A except that a yarn having a non-elastic property is used as a warp yarn.

(Pattern C)

The fiber sheet 200 of a pattern C has (1) a warp yarn, (2) a weft yarn, and (3) a sensor fiber as components. That is, the fiber sheet 200 of the pattern C is the fiber sheet 200 in which an elastic yarn is not used.

Next, a method of manufacturing the fiber sheet 200 of the pattern C will be described. First, a yarn having an elastic property (for example, a covering yarn in which polyurethane is used as a core material) is used as a warp yarn to create a stitch, and the fiber sheet main body 201 in which a weft yarn is woven to form a base cloth is provided. A sensor fiber is inserted and woven to the fiber sheet main body 201 to form the fiber sheet 200 of the pattern C.

Figure 21:
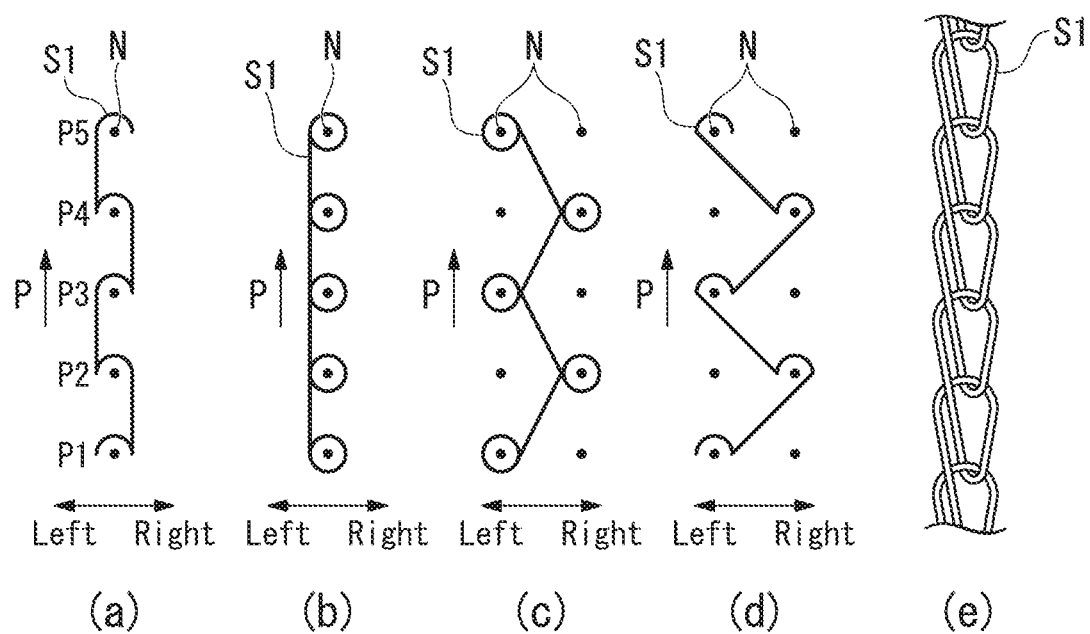
FIG. 21 is a view describing a method of manufacturing a fiber sheet including a sensor fiber, showing a braided tissue of a warp yarn.

Next, a method of manufacturing the bandage-shaped fiber sheet 200 will be described in detail using the fiber sheet 200 of the pattern A as an example. FIG. 21 is a view showing a braided tissue of a warp yarn of the bandage-shaped fiber sheet 200.

First, as shown in FIG. 21, a method of knitting a warp yarn can employ any of an open cloche shown in a part (a) of FIG. 21, a closing cloche shown in a part (b) of FIG. 21, a closing tricot shown in a part (c) of FIG. 21, and an open tricot shown in apart (d) of FIG. 21. In addition, these may be combined. As shown in FIG. 21, the tricot knitting may be made not only by knitting with adjacent knitting needles but also by one-needle skipping or two-needle skipping.

In FIG. 21, N represents a knitting needle. The part (a) of FIG. 21 to the part (d) of FIG. 21 show that a knitting process advances from below to above in a longitudinal direction P in a chronological order. A line S1 represents conveyance of a warp yarn hooked to a knitting needle N.

The open cloche shown in the part (a) of FIG. 21 and the closing cloche shown in the part (b) of FIG. 21 are knitted by the one knitting needle N in a leftward and rightward direction. As shown in the part (a) of FIG. 21, in the open cloche, a warp yarn S1 is hooked from the left to the right at the first rotation P1 of a main shaft 1 shown at the lowermost side, and the warp yarn S1 is hooked from the right to the left at the second rotation P2 of the next main shaft 2. The warp yarn S1 is hooked from the left to the right at the third rotation P3 of the next main shaft 3, and hereinafter, conveyance of the warp yarn S1 is repeated.

The closing tricot shown the part (c) of FIG. 21 and the open tricot shown in the part (d) of FIG. 21 are knitted by the two knitting needles N neighboring in the leftward and rightward direction. That is, the one warp yarn S1 is repeatedly knitted to be hooked to the knitting needle N of a left side or hooked to the knitting needle N of a right side. Specifically, as shown in the part (d) of FIG. 21, the warp yarn S1 is hooked to the needle N of the left side from the left to the right in the first rotation of the main shaft 1, and the warp yarn S1 is hooked to the needle N adjacent to the right side from the right to the left in the second rotation of the main shaft 2. From the third rotation of the main shaft 3, conveyance of the warp yarn S1 is repeated.

A knitted cord as shown in a part (e) of FIG. 21 can be provided by knitting the yarn using the closing cloche shown in the part (b) of FIG. 21. For example, a bag shape having a width of 80 mm can be provided by joining the knitted cords with a weft yarn.

Figure 22:
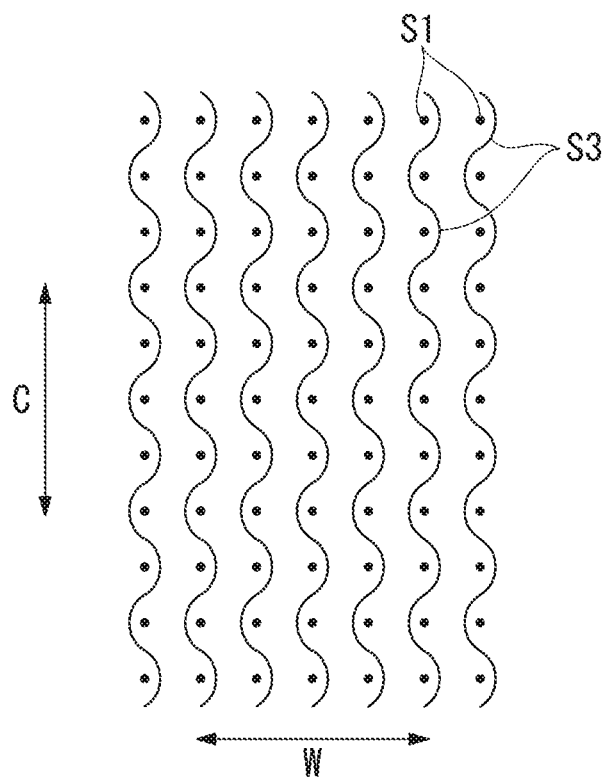
FIG. 22 is a view describing the method of manufacturing the fiber sheet including the sensor fiber, showing weaving of elastic yarns.

Next, an elastic yarn S3 is woven. As shown in FIG. 22, the elastic yarn S3 is woven by being alternately inserted at each stitch with respect to one needle in a course direction (an expansion and contraction direction in a direction of an arrow C, a longitudinal direction of the fiber sheet 200).

An insertion method of a weft yarn S2 may employ, for example, the following four methods.

Figure 23:
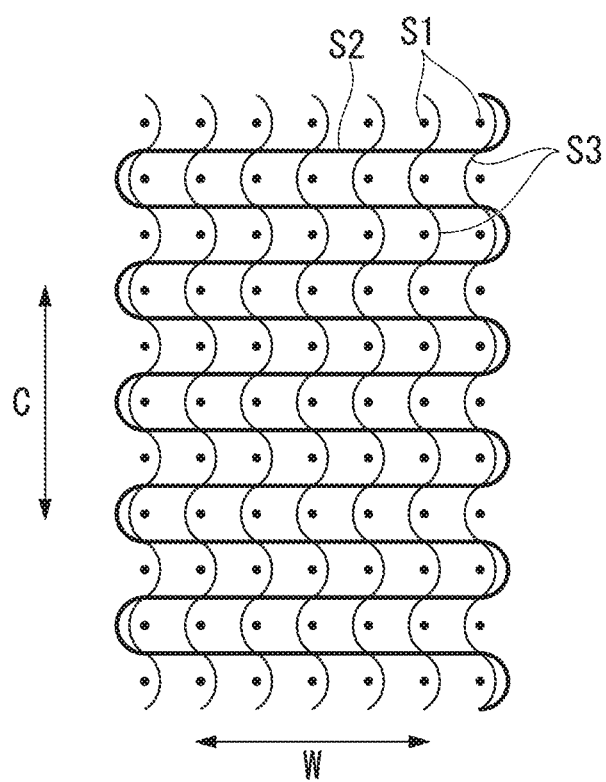
FIG. 23 is a view describing the method of manufacturing the fiber sheet including the sensor fiber, showing a first insertion method of weft yarns.

A first insertion method of the weft yarn S2 will be described. As shown in FIG. 23, the first insertion method of the weft yarn S2 is a method of knitting the fiber sheet main body 201 by inserting the weft yarn S2 that forms the fiber sheet main body 201 (a base cloth, see FIG. 20) of the fiber sheet 200 to reciprocate both ends of the fiber sheet 200 at each stitch.

As such a method is employed, the fiber sheet main body 201 configuring a base cloth of a bandage can be more easily knitted.

Figure 24:
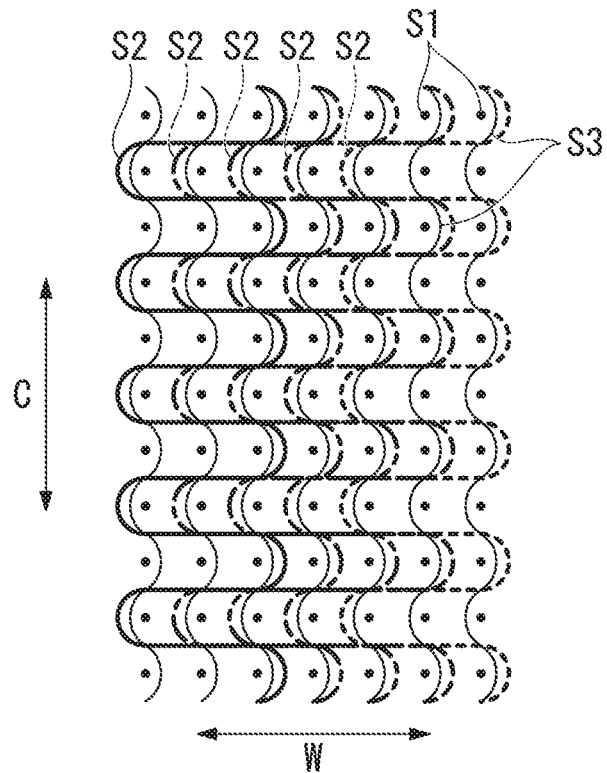
FIG. 24 is a view describing the method of manufacturing the fiber sheet including the sensor fiber, showing a second insertion method of weft yarns.

A second insertion method of the weft yarn S2 will be described. As shown in FIG. 24, the second insertion method of the weft yarn S2 is a method of knitting the fiber sheet main body 201 by disposing the weft yarn S2 that forms the fiber sheet main body 201 in a wale direction of the fiber sheet 200 (a non-expansion and non-contraction direction shown as a direction of an arrow W, a width direction of the fiber sheet 200) side by side.

Figure 25:
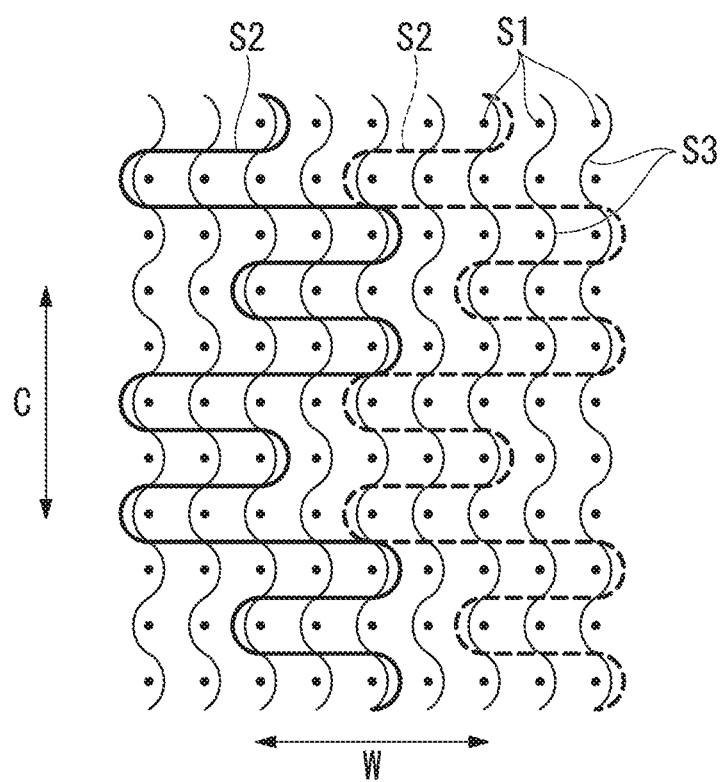
FIG. 25 is a view describing the method of manufacturing the fiber sheet including the sensor fiber, showing a third insertion method of weft yarns.

A third insertion method of the weft yarn S2 will be described. As shown in FIG. 25, the third insertion method of the weft yarn S2 is a method of knitting a specific base cloth such as a mesh M or the like on an arbitrary portion of the fiber sheet main body 201 that becomes a base by inserting the weft yarn S2 that forms the fiber sheet main body 201 to vary a swing side at each arbitrary stitch.

Figure 26:
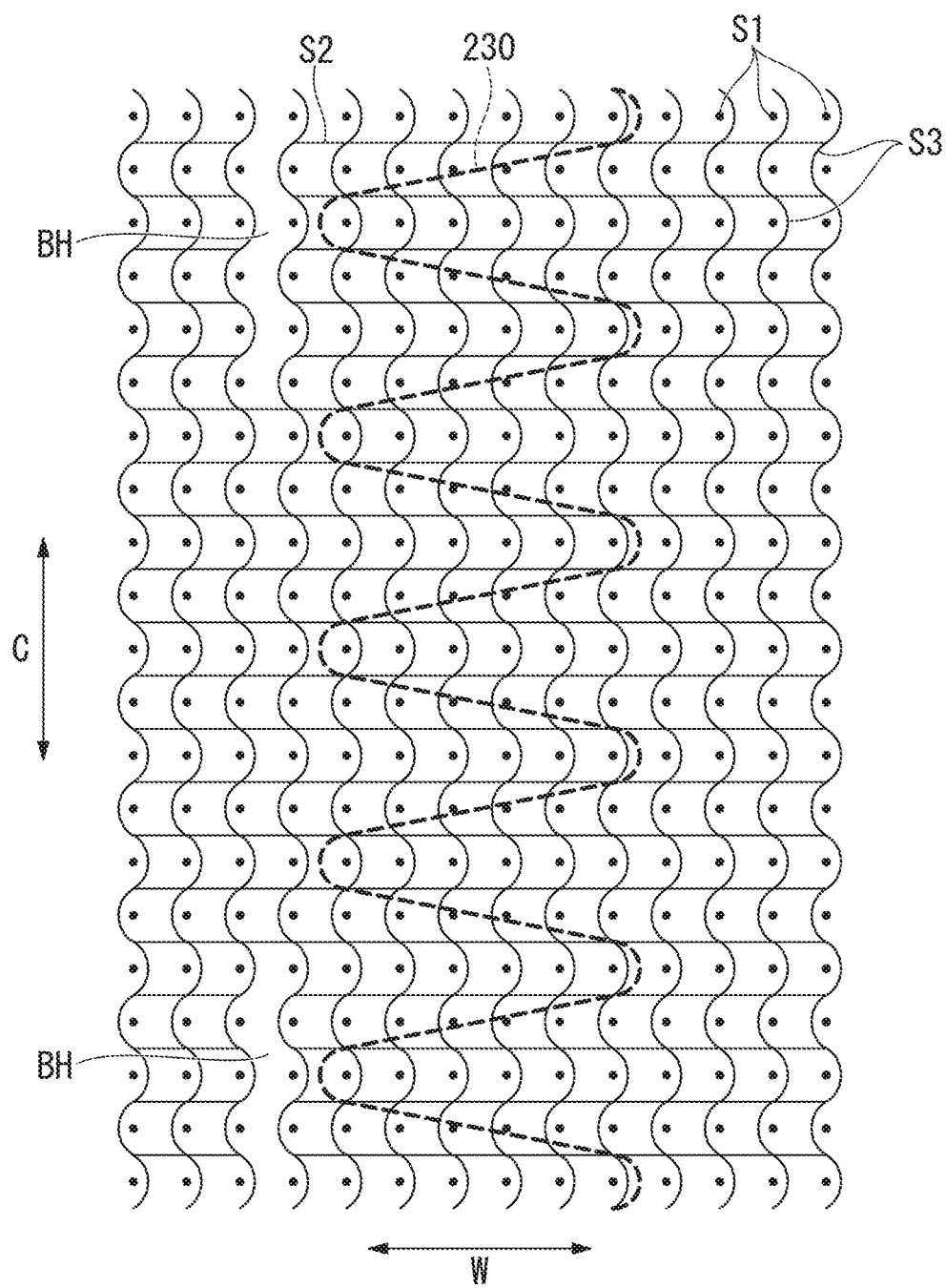
FIG. 26 is a view describing the method of manufacturing the fiber sheet including the sensor fiber, showing a fourth insertion method of weft yarns.

A fourth insertion method of the weft yarn S2 will be described. As shown in FIG. 26, the fourth insertion method of the weft yarn S2 is a method of knitting a specific base cloth such as a button hole BH or the like on an arbitrary portion of the fiber sheet main body 201 by inserting the weft yarn S2 that forms the fiber sheet main body 201 to vary a swing side at each arbitrary stitch.

Next, the sensor fiber 230 is woven. For example, a weaving method of the sensor fiber 230 can employ the following two methods.

Figure 27:
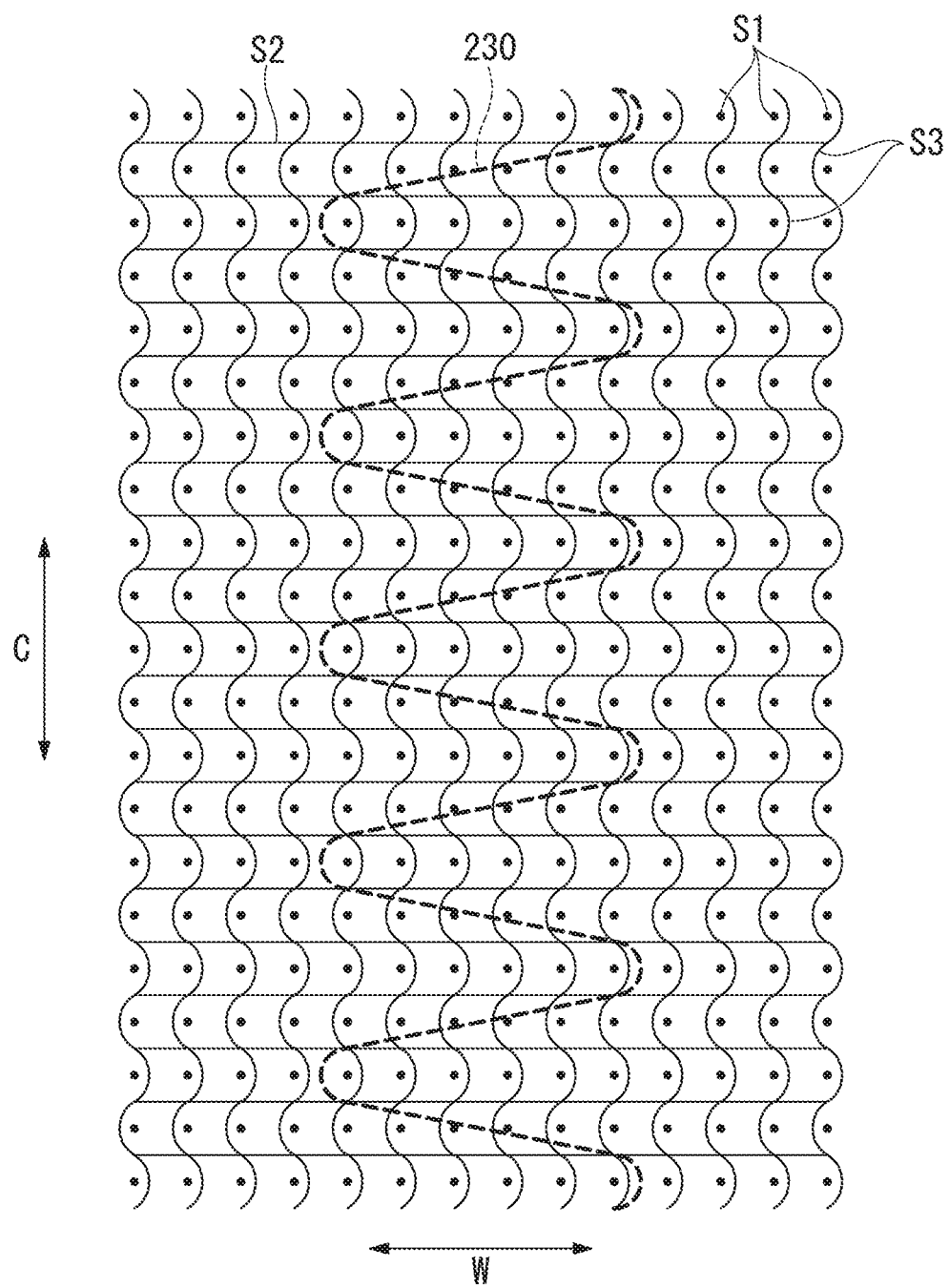
FIG. 27 is a view describing a method of manufacturing a fiber sheet including a sensor fiber, showing a first weaving method of a sensor fiber.

The first weaving method of the sensor fiber 230 will be described. As shown in FIG. 27, the first weaving method of the sensor fiber 230 is a method of knitting a base cloth by inserting the sensor fiber 230 into a central portion of the fiber sheet 200 to form a waveform (a sine curve shape) with an arbitrary length and at an arbitrary period.

As such a method is employed, the sensor fiber 230 can be disposed in a well-balanced manner. Further, a disposition type of the sensor fiber 230 is not limited to the waveform and may be a square waveform.

Figure 28:
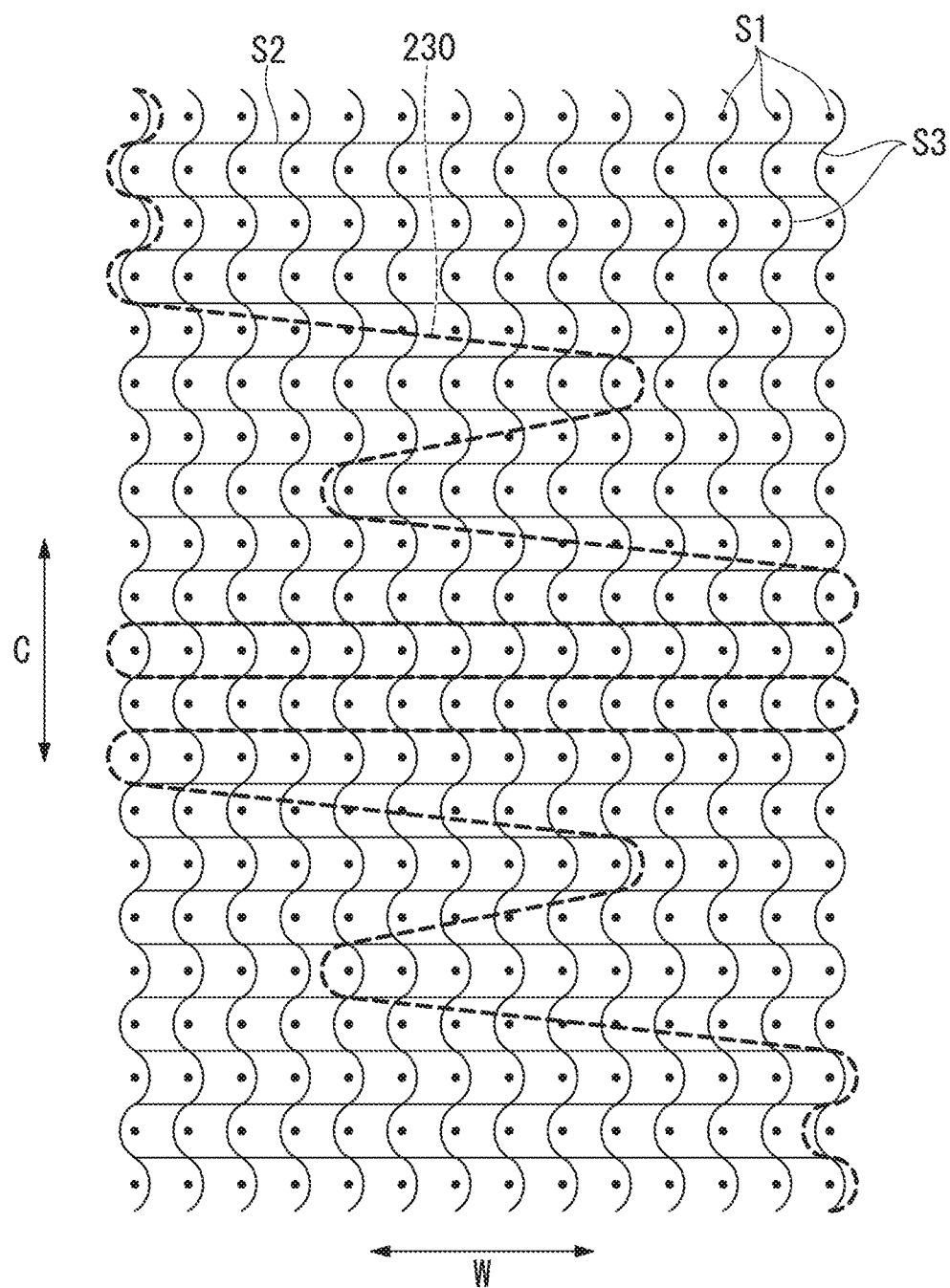
FIG. 28 is a view describing the method of manufacturing the fiber sheet including the sensor fiber, showing a second weaving method of a sensor fiber.

A second weaving method of the sensor fiber 230 will be described. As shown in FIG. 28, the second weaving method of the sensor fiber 230 is a method of increasing a width in a wale direction W at a specific portion by inserting the sensor fiber 230 into, for example, one end of the fiber sheet 200, or decreasing a period in a course direction C (an interval of the sensor fibers 230 neighboring in an extending direction of the fiber sheet 200). That is, amplitude and a period of the waveform of the sensor fiber 230 may be arbitrarily varied.

As such a method is employed, sensing according to a purpose becomes possible.

Next, a connecting method of the fiber sheet 200 in which the sensor fiber 230 is disposed and the detection device 100 will be described.

A connector is used to connect the first conductive yarn 231 (the first conductive body 210) and the second conductive yarn 233 (the second conductive body 220) of the sensor fiber 230 to the detection device 100. Hereinafter, four types of connecting structures using a first connector 60, a second connector 75, a third connector 90, and a fourth connector 95 will be described.

First, the first connector 60 will be described.

Figure 29:
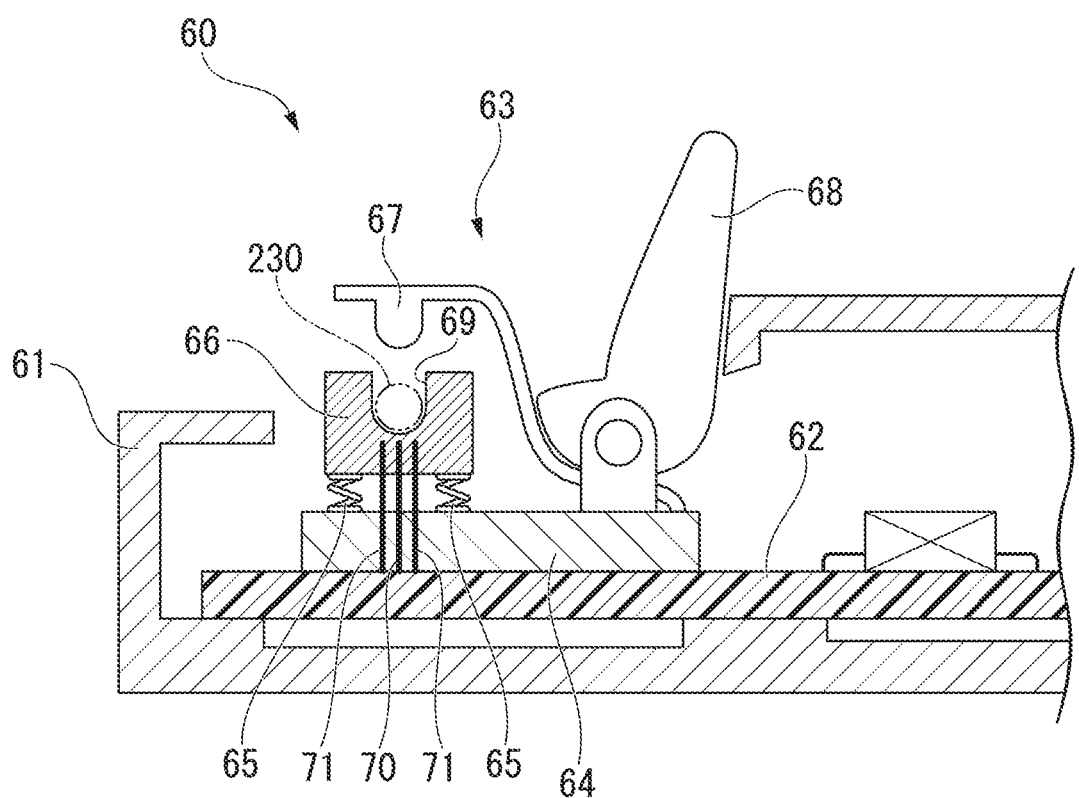
FIG. 29 is a cross-sectional view showing a schematic structure of a first connector.

As shown in FIG. 29, the first connector 60 includes a casing 61, a board 62 disposed in the casing 61, and a connecting unit 63 configured to connect the sensor fiber 230 and the board 62. The board 62 is connected to the detection device 100 (see FIG. 1) via a cable or the like.

The connecting unit 63 includes a base section 64, a sensor guide 66 placed on the base section 64 via a compression coil spring 65, a pressing member 67 configured to push the sensor fiber 230 into the sensor guide 66, and a lock lever 68 configured to push the pressing member 67 into the sensor guide 66.

The first connector 60 pushes the sensor fiber 230 into a recessed groove 69 formed in the sensor guide 66, and connects the sensor fiber 230 and the board 62 via terminals 70 and 71 disposed in the recessed groove 69 of the sensor guide 66.

Figure 30:
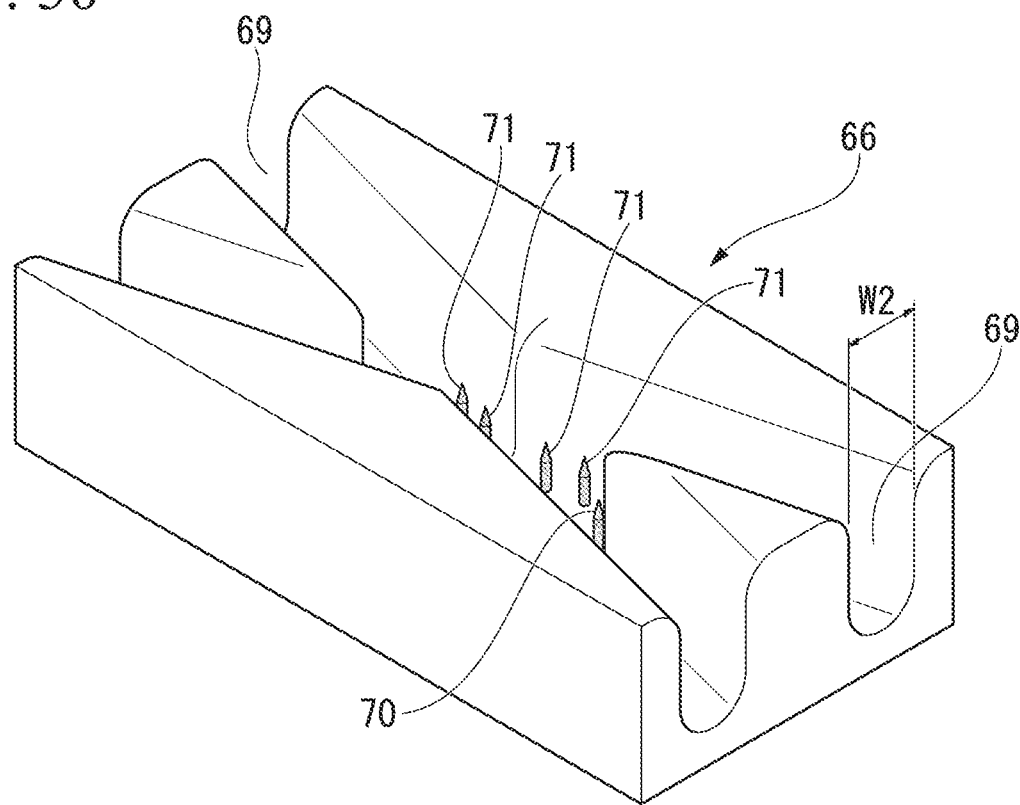
FIG. 30 is a perspective view of a sensor guide that configures the first connector.
Figure 31:
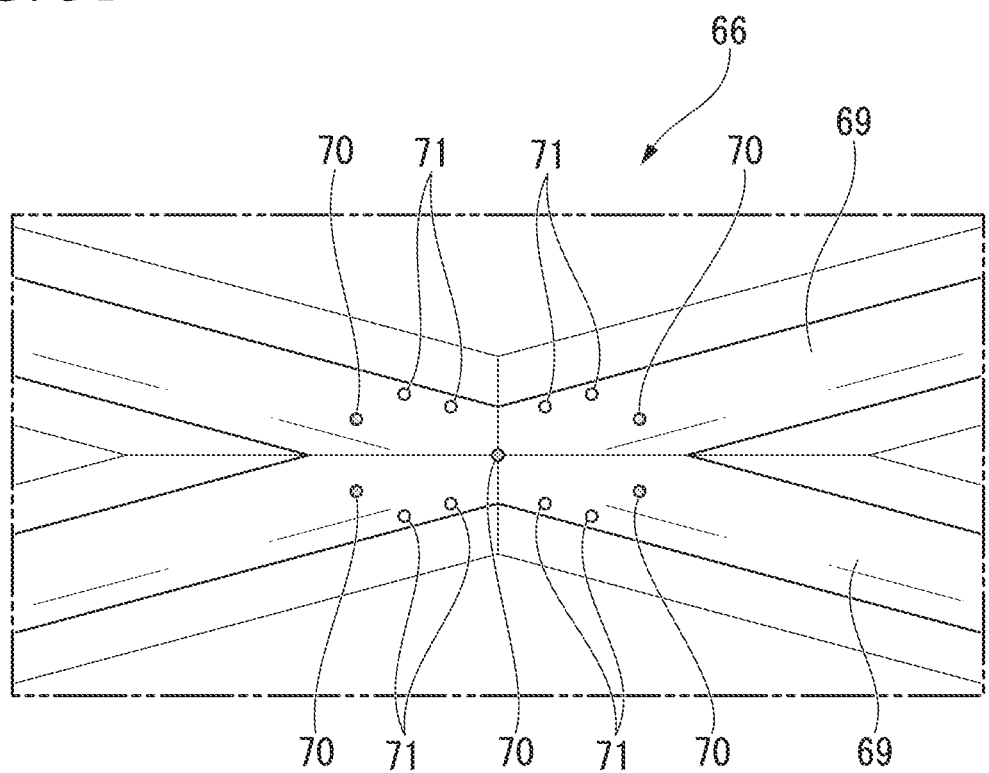
FIG. 31 is a plan view of the sensor guide that configures the first connector.

As shown in FIG. 30, the sensor guide 66 is a block-shaped member formed of plastic such as a polyacetal resin or the like. At least one recessed groove 69 is formed in an upper surface of the sensor guide 66. The recessed groove 69 is a groove having a U-shaped end surface extending in one direction and formed in a linear shape. As shown in FIG. 31, in the embodiment, two recessed grooves 69 are formed in the upper surface of the sensor guide 66 to cross each other.

The reason for this is that, when the sensor fiber 230 is interwoven on the bandage in a wave shape in FIG. 20 and the connector is sandwiched from a lateral direction that is a cross section of the bandage, the sensor fiber 230 is oriented in two directions of "a diagonally rightward upward direction" and "a diagonally rightward downward direction" according to a cutting place thereof. The sensor guide 66 is configured to be capable of corresponding by one connector even in any direction.

The recessed groove 69 has a size corresponding to a thickness of the sensor fiber 230. A width W2 of the recessed groove 69 in a direction perpendicular to the longitudinal direction thereof is slightly smaller than the diameter of the sensor fiber 230. That is, the recessed groove 69 is formed such that the sensor fiber 230 is fixed into the recessed groove 69 as the sensor fiber 230 is pushed from above. A lower surface of the sensor guide 66 is disposed parallel to the board 62.

Figure 32:
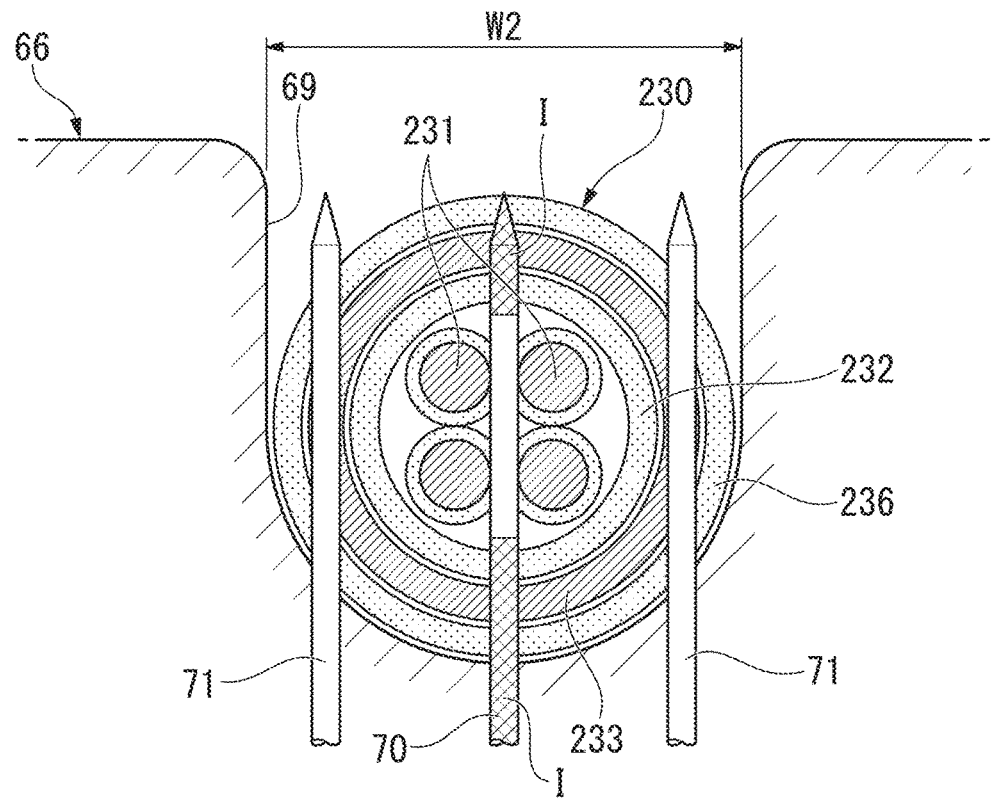
FIG. 32 is a cross-sectional view showing a plurality of terminals that configure a connecting unit of the first connector.

As shown in FIG. 32, the plurality of terminals 70 and 71 protrudes upward from the board 62 in a vertical direction. The plurality of terminals 70 and 71 are configured by at least one terminal 70 for a center conductor and at least one terminal 71 for an external connector. The terminals 70 and 71 are disposed to protrude from a lower side of the sensor guide 66 in an internal space of the recessed groove 69 via a through-hole formed in the sensor guide 66. The sensor guide 66 is supported by the compression coil spring 65 and the terminals 70 and 71 protrude from an inner circumferential surface of the recessed groove 69 by pressing the sensor guide 66 from above.

The terminal 70 for a center conductor is disposed at a center of the recessed groove 69 in a widthwise direction. In other words, the terminal 70 for a center conductor is disposed such that the terminal 70 for a center conductor pierces the vicinity of the center of the sensor fiber 230 by pressing the sensor guide 66 from above while inserting the sensor fiber 230 into the recessed groove 69. Accordingly, the first conductive yarn 231 (see FIGS. 9 and 10) of the sensor fiber 230 and the detection device 100 are connected to each other. Further, a portion of the terminal 70 for a center conductor is coated with an insulating coating I, and the terminal 70 for a center conductor and the second conductive yarn 233 of the sensor fiber 230 are configured not to be electrically connected.

The terminal 71 for an external conductor is disposed outside in the widthwise direction rather the center of the recessed groove 69 in the widthwise direction. In other words, the terminal 71 for an external conductor is disposed such that the terminal 71 for an external conductor pierces an outer circumferential side rather than the center of the sensor fiber 230 by pressing the sensor guide 66 from above while inserting the sensor fiber 230 into the recessed groove 69. Accordingly, the second conductive yarn 233 of the sensor fiber 230 and the detection device 100 are connected to each other.

As the first connector 60 is used, the conductive yarn and the detection device 100 can be easily connected to each other by only fitting the sensor fiber 230 into the recessed groove 69 of the sensor guide 66 without peeling the coating of the sensor fiber 230.

Figure 33:
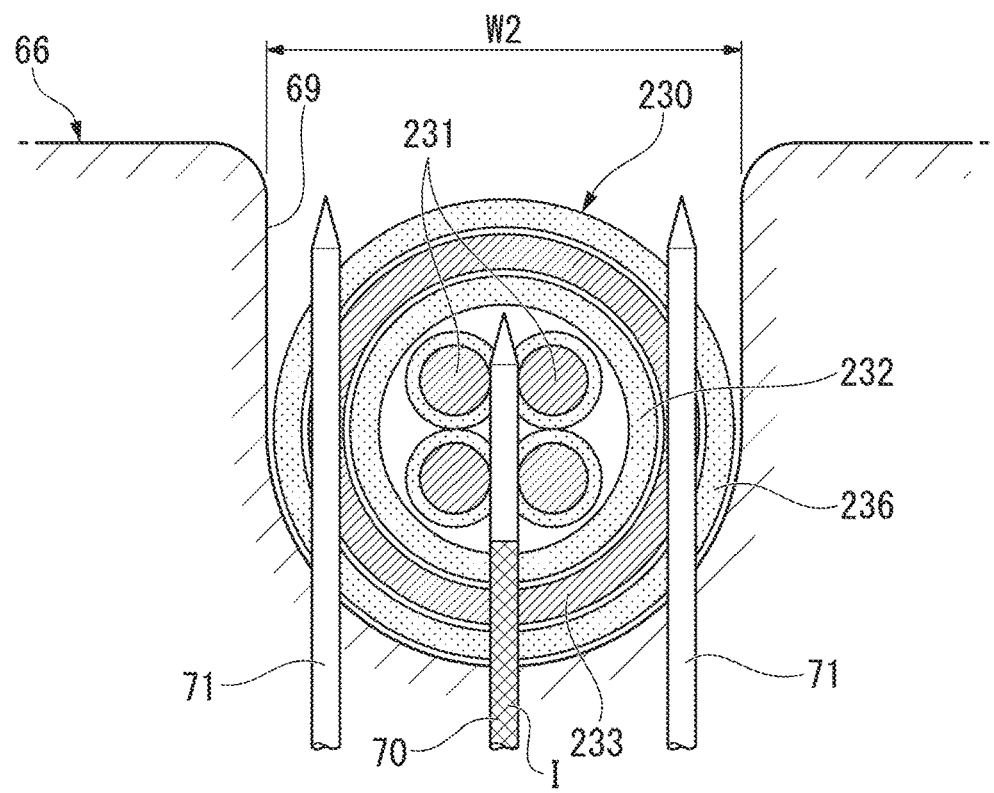
FIG. 33 is a cross-sectional view showing another example of the plurality of terminals that configure the connecting unit of the first connector.

Further, configurations of the terminals 70 and 71 are not limited to the configurations shown in FIG. 32. For example, as shown in FIG. 33, a length of the terminal 70 for a center conductor may be decreased.

While the first conductive yarn 231 and the second conductive yarn 233 are configured not to be electrically connected to each other, an inherent impedance value can be provided to between both of the electrodes during manufacture. For this reason, when the terminal 70 for a center conductor and the terminal 71 for an external conductor do not appropriately contact with the conductive yarns thereof, respectively, a value other than the inherent impedance value is shown, an accident due to a contact error can be prevented in advance. Similarly, when the terminal 70 for a center conductor and the terminal 71 for an external conductor come in contact with each other due to a manufacturing error or the like, since an extremely low impedance value is shown, a detection error can be prevented in advance.

In addition, the first connector is not limited to the above-mentioned structure, and simplification thereof is also possible.

Figure 34:
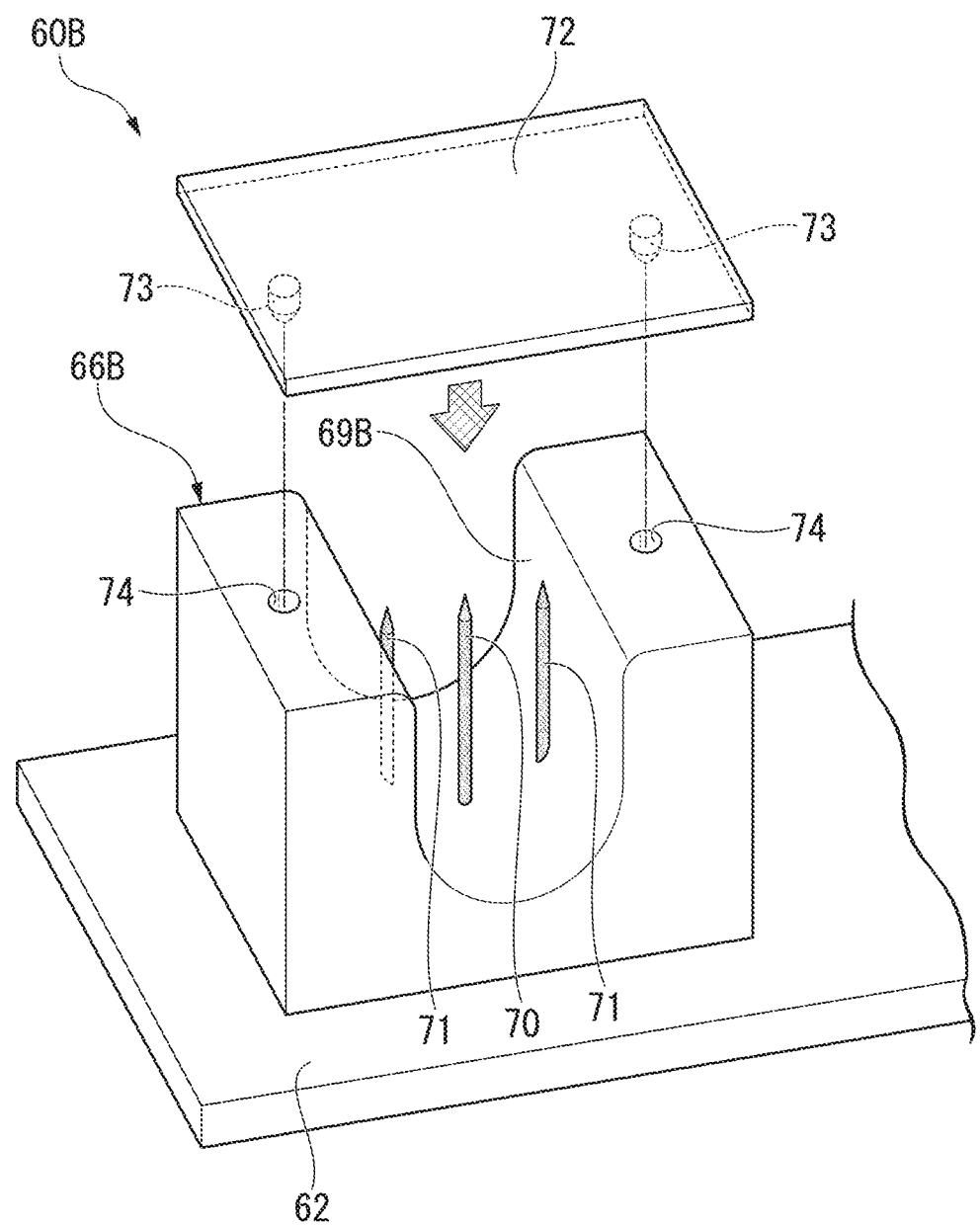
FIG. 34 is a perspective view describing a structure of another type of the first connector.

For example, like the first connector 60B shown in FIG. 34, a configuration in which only a block-shaped sensor guide 66B in which a recessed groove 69B having a U-shaped cross section is formed and a lid member 72 are included may be provided.

The recessed groove 69B has a shape corresponding to the thickness of the sensor fiber 230, and the terminals 70 and 71 that connect the sensor fiber 230 and the board 62 are disposed therein. The lid member 72 is a member configured to push and fix the sensor fiber 230 into the recessed groove 69B. A protrusion 73 put into a guide hole 74 formed in the upper surface of the sensor guide 66B is formed on a lower surface of the lid member 72.

Next, the second connector 75 will be described.

Figure 35:
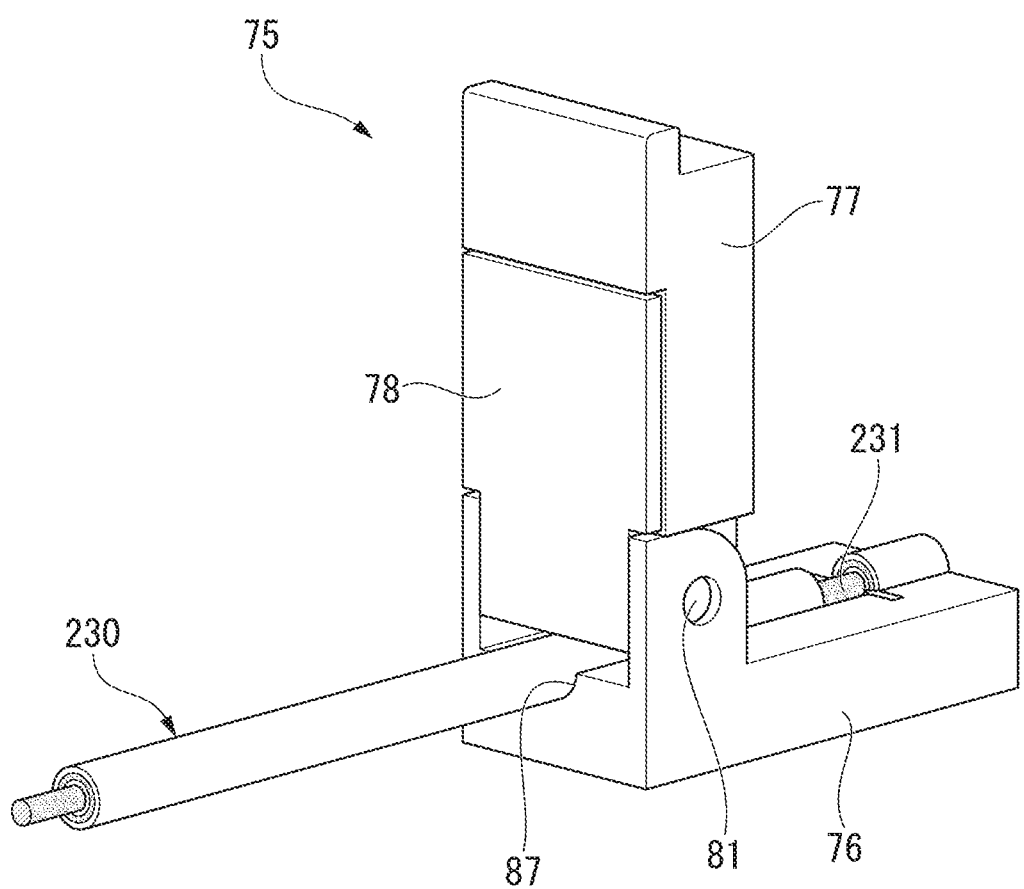
FIG. 35 is a perspective view of a second connector.

As shown in FIG. 35, the second connector 75 has a base section 76, a wire stripper unit 77 pivotably attached to the base section 76, and a terminal section 78 pivotably attached to the base section 76.

Figure 36:
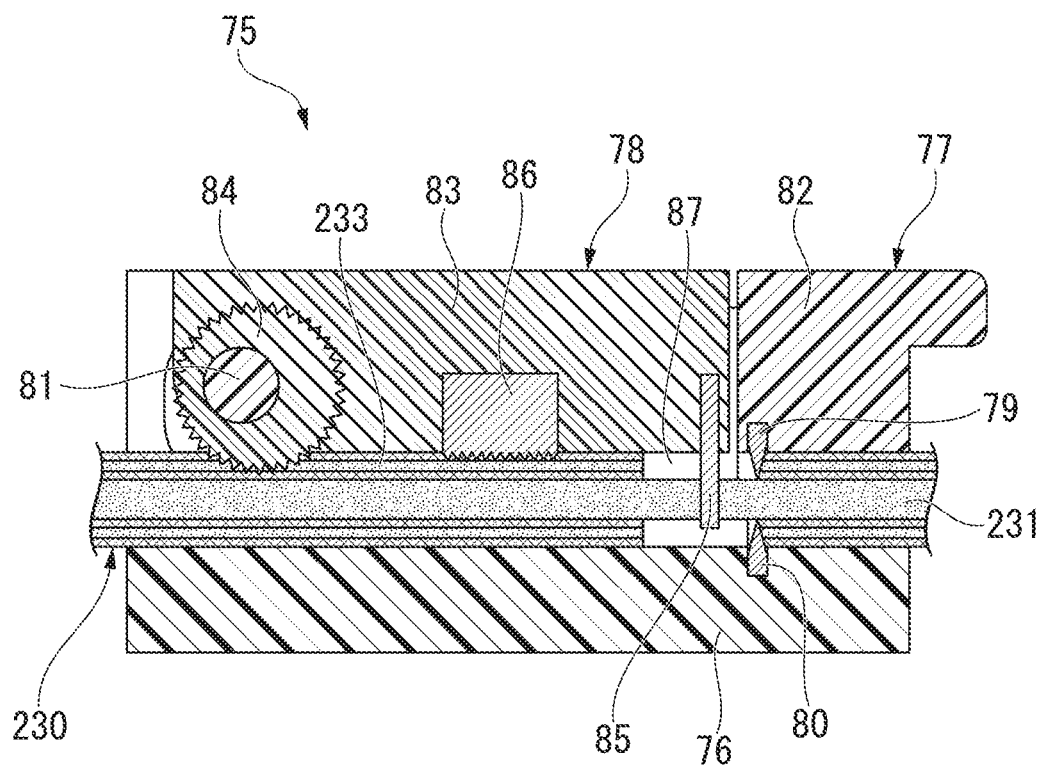
FIG. 36 is a cross-sectional view showing a schematic structure of the second connector.

The wire stripper unit 77 is a portion having a function of a so-called wire stripper. As shown in FIG. 36, the wire stripper unit 77 has a wire stripper unit main body 82 that is pivotable about a pivot shaft 81, and a first circular hole blade 79. The first circular hole blade 79 is a semi-circular groove-shaped blade configured to cooperate with a second circular hole blade 80 fixed to the base section 76 to form a notch in a portion except for the conductive yarn 231 of the sensor fiber 230.

The terminal section 78 has a terminal section main body 83 that is pivotable about the pivot shaft 81, a terminal 85 for a center conductor configured to be connected to the first conductive yarn 231, a terminal 86 for an external conductor configured to be connected to the second conductive yarn 233, and a roller 84 integrally attached to the pivot shaft 81. The terminal 85 for a center conductor and the terminal 86 for an external conductor are connected to the detection device 100 (see FIG. 1) via a cable or the like.

The terminal 86 for an external conductor is configured of a plurality of needle shapes. As the terminal 86 for an external conductor is pushed from the outer circumferential surface of the sensor fiber 230, the terminal 86 for an external conductor is connected to the second conductive yarn 233.

The roller 84 has a plurality of fine concavo-convex portion formed on an outer circumferential surface having a cylindrical shape (knurling). The roller 84 is eccentrically attached to the pivot shaft 81. As the terminal section 78 is in a fallen-down state shown in FIG. 36 from a standing-up state shown in FIG. 35, the outer circumferential surface of the roller 84 bites into the outer circumferential surface of the sensor fiber 230 fixed into a fixing groove 87 of the base section 76.

Figure 37:
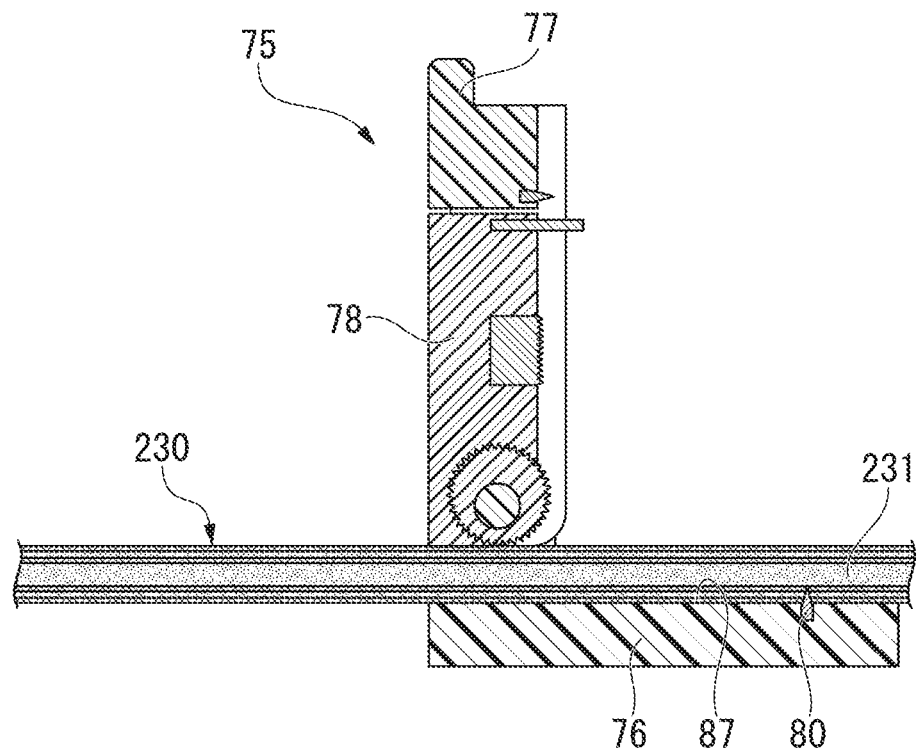
FIG. 37 is a cross-sectional view describing an operation of the second connector, showing an aspect in which a sensor fiber is disposed on the second connector.

When connection of the sensor fiber 230 and the detection device 100 is performed using the second connector 75, first, as shown in FIG. 37, the sensor fiber 230 is disposed in the fixing groove 87 of the base section 76. Accordingly, the second circular hole blade 80 is cut into a portion except for the first conductive yarn 231 of the sensor fiber 230.

Figure 38:
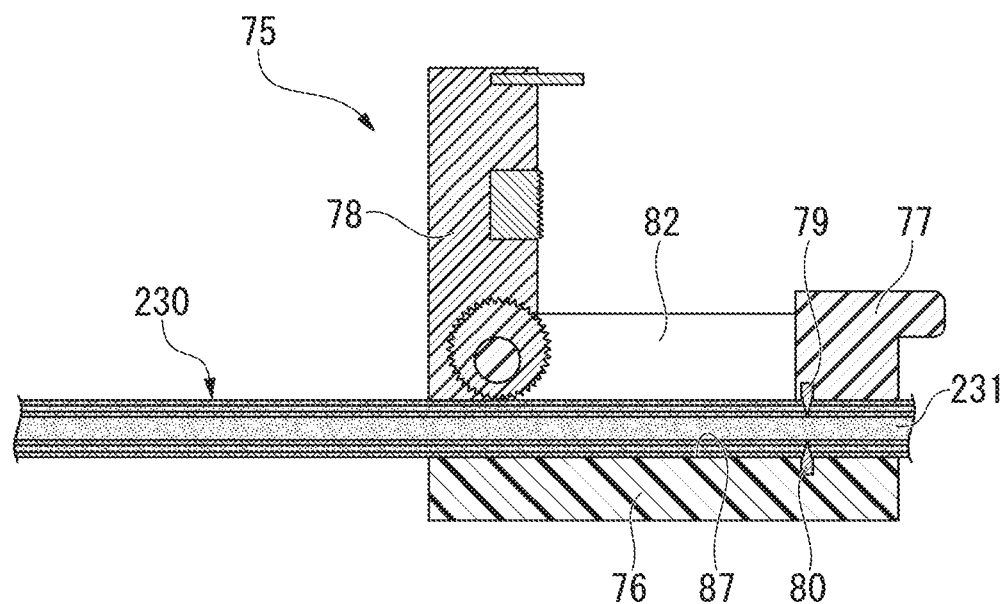
FIG. 38 is a cross-sectional view describing an operation of the second connector, showing an aspect in which a notch is formed in the sensor fiber using a wire stripper unit.

Next, as shown in FIG. 38, as the wire stripper unit 77 is pushed down, a notch is formed in a portion other than the first conductive yarn 231 of the sensor fiber 230 so that the first conductive yarn 231 remains. As the wire stripper unit 77 is pushed down, the sensor fiber 230 is fixed by the wire stripper unit main body 82.

Figure 39:
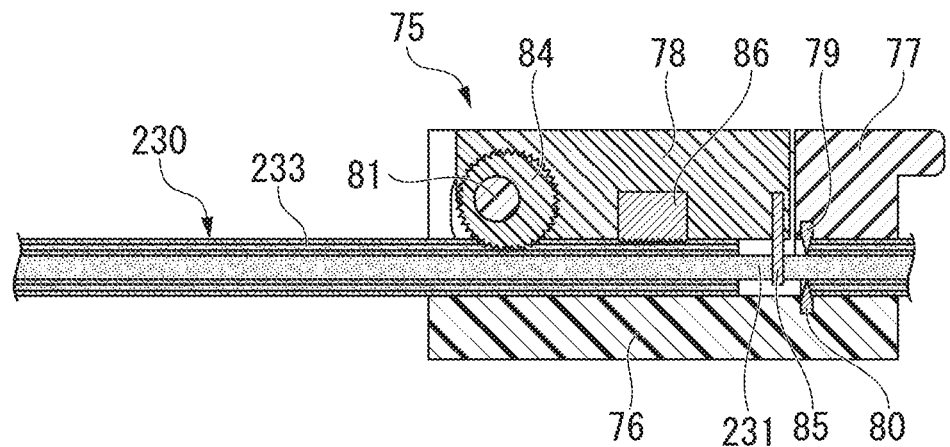
FIG. 39 is a cross-sectional view describing an operation of the second connector, showing an aspect in which a terminal section and a conductive yarn are connected.

Next, as shown in FIG. 39, as the terminal section 78 is pushed down, the terminal 85 for a center conductor is pressed against the first conductive yarn 231 while the roller 84 exposes the first conductive yarn 231, and thus, the first conductive yarn 231 and the terminal 85 for a center conductor are connected to each other. Similarly, the terminal 86 for an external conductor passes through the sensor fiber 230 to be connected to the second conductive yarn 233.

As the second connector 75 is used, the coating of the sensor fiber 230 can be peeled by an operation of the wire stripper unit 77, and the conductive yarn and the detection device 100 can be easily connected to each other. Further, in order to more easily peel the coating, the same mechanism as the roller 84 may be incorporated in the base section 76.

Next, the third connector 90 will be described.

Figure 40:
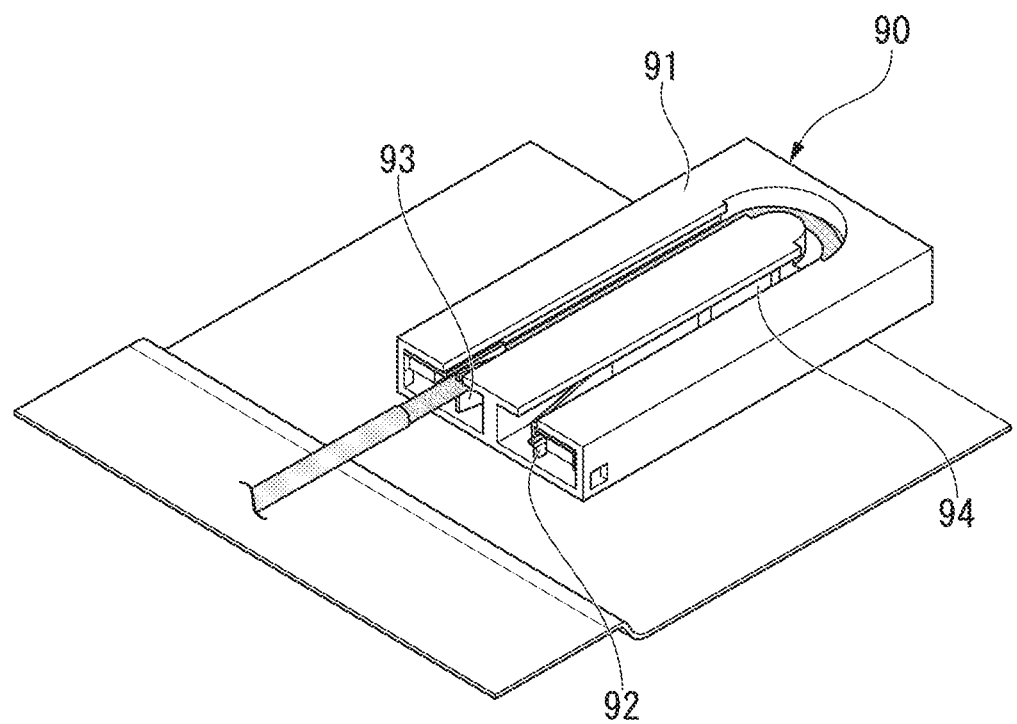
FIG. 40 is a perspective view of a third connector.

As shown in FIG. 40, the third connector 90 has a casing 91, a terminal 92 for a center conductor fixed to the casing 91 and a terminal 93 for an external conductor. The terminal 92 for a center conductor and the terminal 93 for an external conductor are fixed to the detection device 100 (see FIG. 1).

The casing 91 has a box shape, and a wire-accommodating groove 94 extending in a U shape when seen from above is formed therein.

Figure 41:
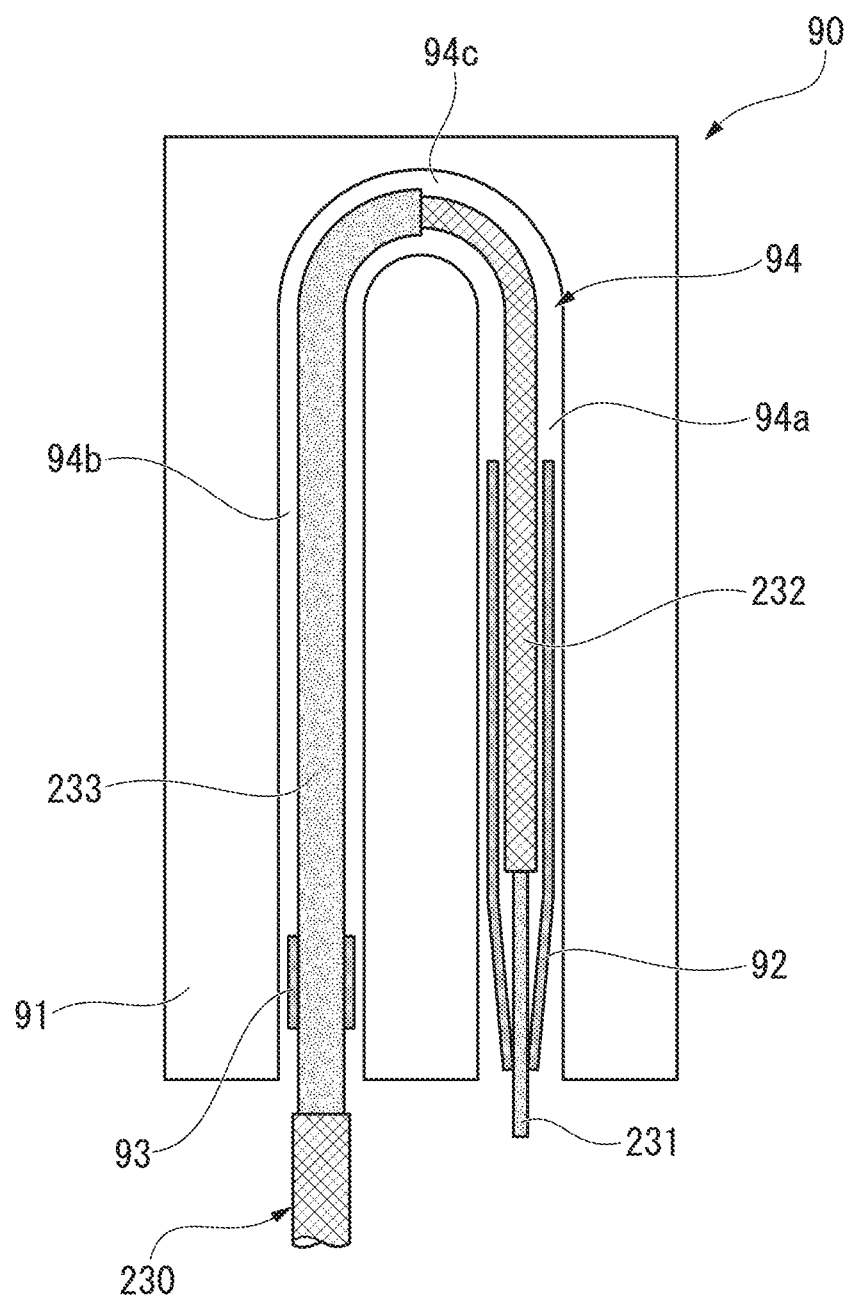
FIG. 41 is a plan view showing a schematic structure of the third connector.

As shown in FIG. 41, the wire-accommodating groove 94 has a first straight section 94a in which the terminal 92 for a center conductor is accommodated, a second straight section 94b in which the terminal 93 for an external conductor is accommodated, and a curved section 94c that smoothly connects the first straight section 94a and the second straight section 94b. Further, while the wire-accommodating groove 94 may not be formed in a U shape when seen from above, the U shape is preferable in consideration of a user's convenience.

The terminal 92 for a center conductor is configured of a pair of terminals disposed to gradually approach in one direction of an extension direction of the first straight section 94a. While tip portions of the pair of terminals come in contact with each other, the first conductive yarn 231 can be sandwiched between the pair of terminals.

The terminal 93 for an external conductor is also configured of a pair of terminals disposed to gradually approach in one direction of an extension direction of the second straight section 94b. The pair of terminals are disposed such that a distance between tip portions of the pair of terminals is slightly smaller than a diameter of the sensor fiber 230.

When a user brings the sensor fiber 230 to be connected to the third connector 90, the first conductive yarn 231 and the second conductive yarn 233 are exposed to match with the wire-accommodating groove 94 by a wire stripper, a nipper, or the like. Next, as the sensor fiber 230 is accommodated in the wire-accommodating groove 94, the first conductive yarn 231 is connected to the terminal 92 for a center conductor and the second conductive yarn 233 is connected to the terminal 93 for an external conductor.

As the third connector 90 is used, the conductive yarn and the detection device 100 can be connected by simply peeling the coating of the sensor fiber 230.

Next, the fourth connector 95 will be described.

Figure 42:
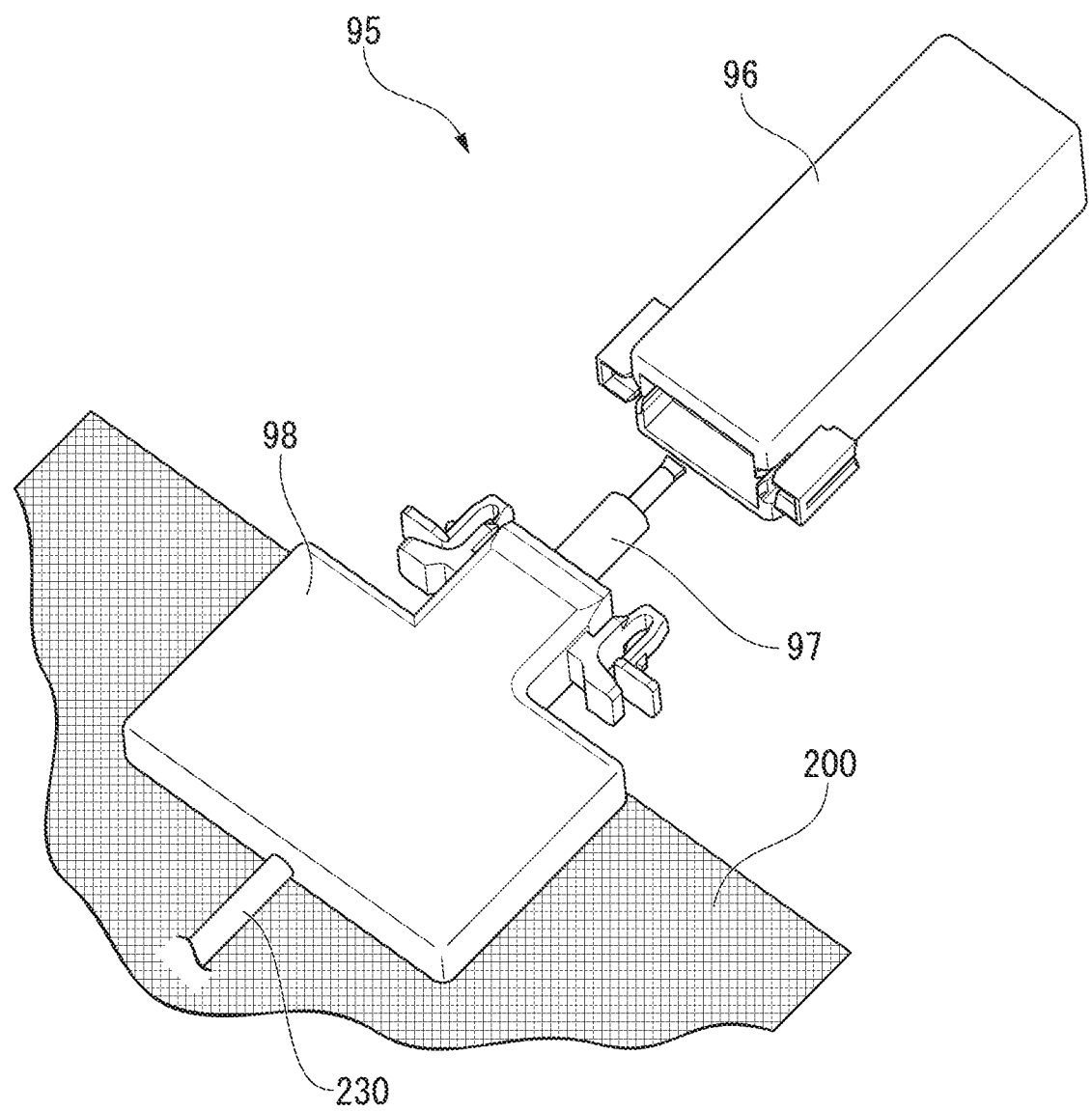
FIG. 42 is a perspective view of a fourth connector.

As shown in FIG. 42, the fourth connector 95 is a connector using a conventional coaxial connector. The fourth connector 95 has a female connector 96, a male connector 97 connected to the female connector 96, and a fixing holder 98 configured to fix the male connector 97 to the fiber sheet 200. The female connector 96 has a plurality of terminals (not shown), and these terminals are connected to the detection device 100.

The male connector 97 and the female connector 96 form a connector for a coaxial cable formed of a resin. A user can perform terminal processing of the sensor fiber 230, connect the sensor fiber 230 to the male connector 97, and fix the male connector 97 to the fiber sheet 200 using the fixing holder 98. Then, as the female connector 96 is connected to the male connector 97, the conductive yarns 231 and 233 can be connected to the detection device 100.

Hereinabove, while four types of connectors have been described, for example, it is possible to reduce the cost of the fiber sheet 200 that is a consumable item using the first connector 60, the second connector 75 and the third connector 90 although the price of the connector is expensive.

Next, another disposition example of the first conductive body 210 and the second conductive body 220 in the fiber sheet will be described with reference to FIGS. 43 to 53. The first conductive body 210 and the second conductive body 220 in the fiber sheet can be variously disposed.

Figure 43:
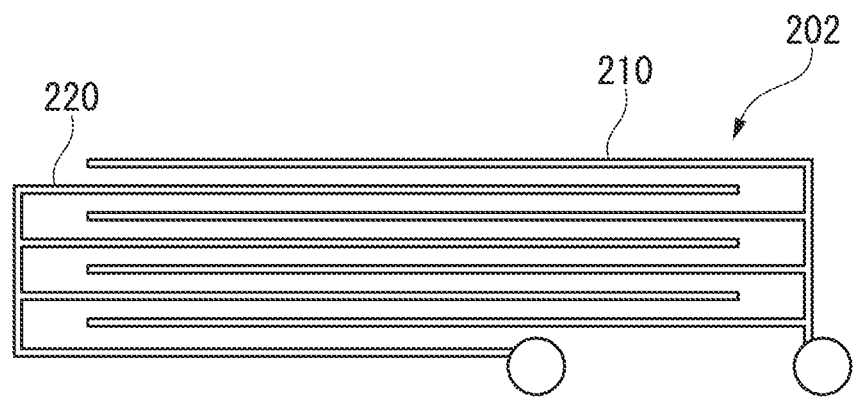
FIG. 43 is a view describing a first example of another disposition of a first conductive body and a second conductive body in the embodiment.

FIG. 43 is a view describing a first example of another disposition of the first conductive body 210 and the second conductive body 220 in a fiber sheet 202. In the disposition example shown in FIG. 43, the first conductive body 210 and the second conductive body 220 are alternately disposed. When blood drops down between the first conductive body 210 and the second conductive body 220, frequency characteristics between the first conductive body 210 and the second conductive body 220 are varied. Accordingly, the detection signal output unit 191 can detect a leakage of blood.

Further, the first conductive body 210 or the second conductive body 220 may be disposed to have a certain level of width.

Figure 44:
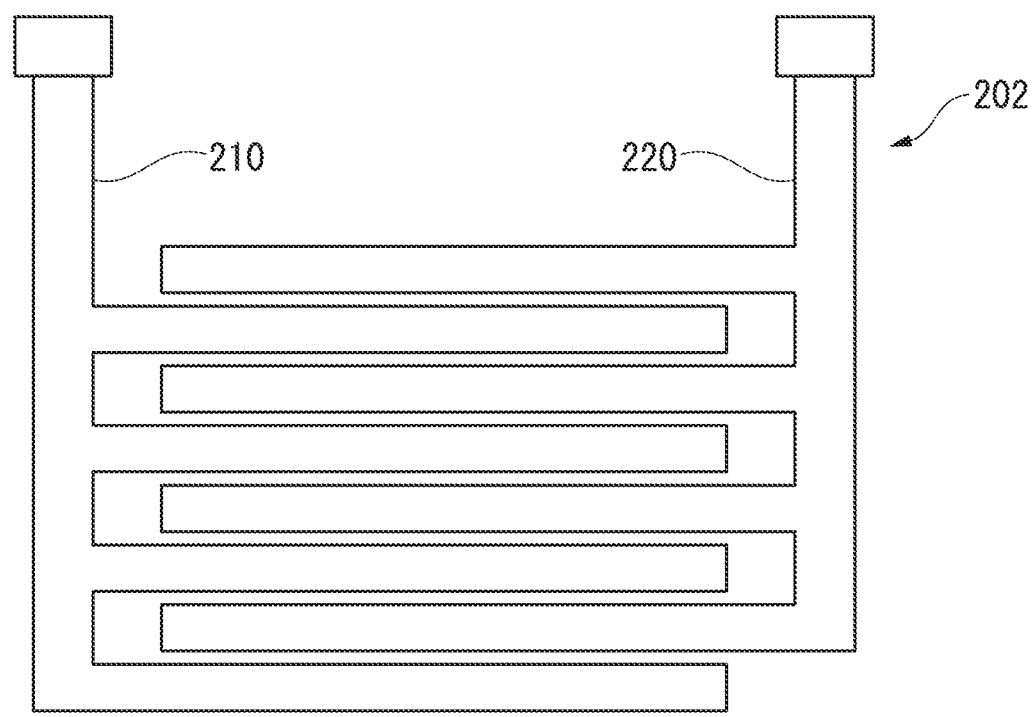
FIG. 44 is a view describing a second example of another disposition of the first conductive body and the second conductive body in the embodiment.

FIG. 44 is a view describing a second example of another disposition of the first conductive body 210 and the second conductive body 220. Like the example in FIG. 43, even in the example in FIG. 44, the first conductive body 210 and the second conductive body 220 are alternately disposed. However, a width of the first conductive body 210 or the second conductive body 220 is larger in the example in FIG. 44 than in the case of FIG. 43. Accordingly, an interval between the first conductive body 210 and the second conductive body 220 is narrowed to be smaller than in the case of FIG. 43. As the interval between the first conductive body 210 and the second conductive body 220 is narrowed, a variation in impedance characteristics when blood drops down between the first conductive body 210 and the second conductive body 220 is further increased, and it is expected that the detection device 100 can easily detect dripping of blood.

Figure 45:
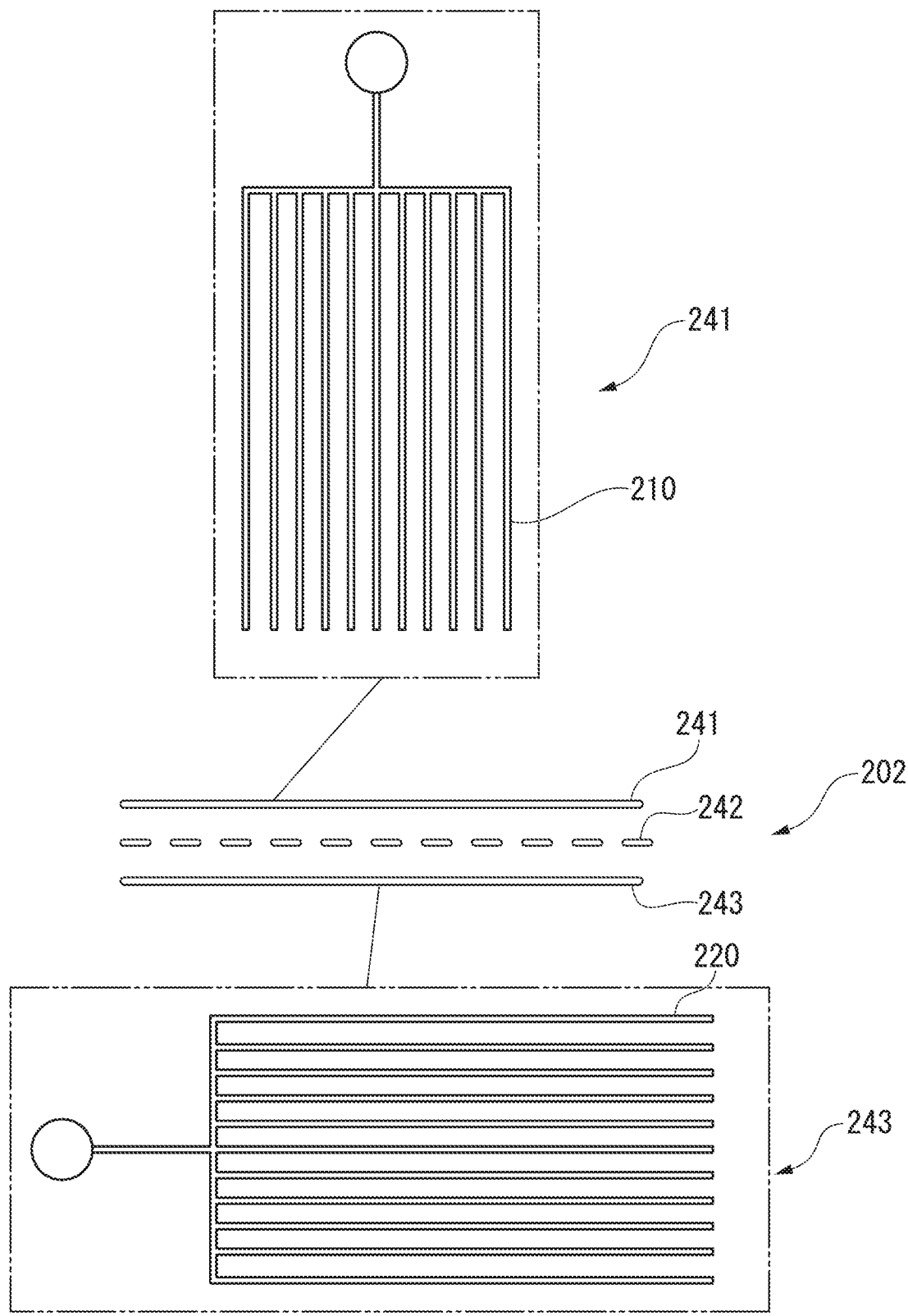
FIG. 45 is a view describing a third example of another disposition of the first conductive body and the second conductive body in the embodiment.

FIG. 45 is a view describing a third example of another disposition of the first conductive body 210 and the second conductive body 220. In the disposition example in FIG. 45, the fiber sheet 202 is configured as a 3-layer structure in which a sheet 242 is sandwiched between a sheet 241 including the first conductive body 210 and a sheet 243 including the second conductive body 220. Further, the first conductive body 210 and the second conductive body 220 may be disposed in different directions or may be disposed in the same direction.

All of a main body of the sheet 241, a main body of the sheet 243, and the sheet 242 are insulating sheets having absorbency. As the sheet 242 is sandwiched, the first conductive body 210 and the second conductive body 220 do not come in contact with each other. In addition, when the sheet 242 absorbs moisture such as blood or the like, impedance characteristics between the first conductive body 210 and the second conductive body 220 are varied. Accordingly, the detection signal output unit 191 can detect a leakage of blood to the fiber sheet 202.

Further, in the first conductive body 210 and the second conductive body 220, channels having wires that are independent from each other may be configured.

Figure 46:
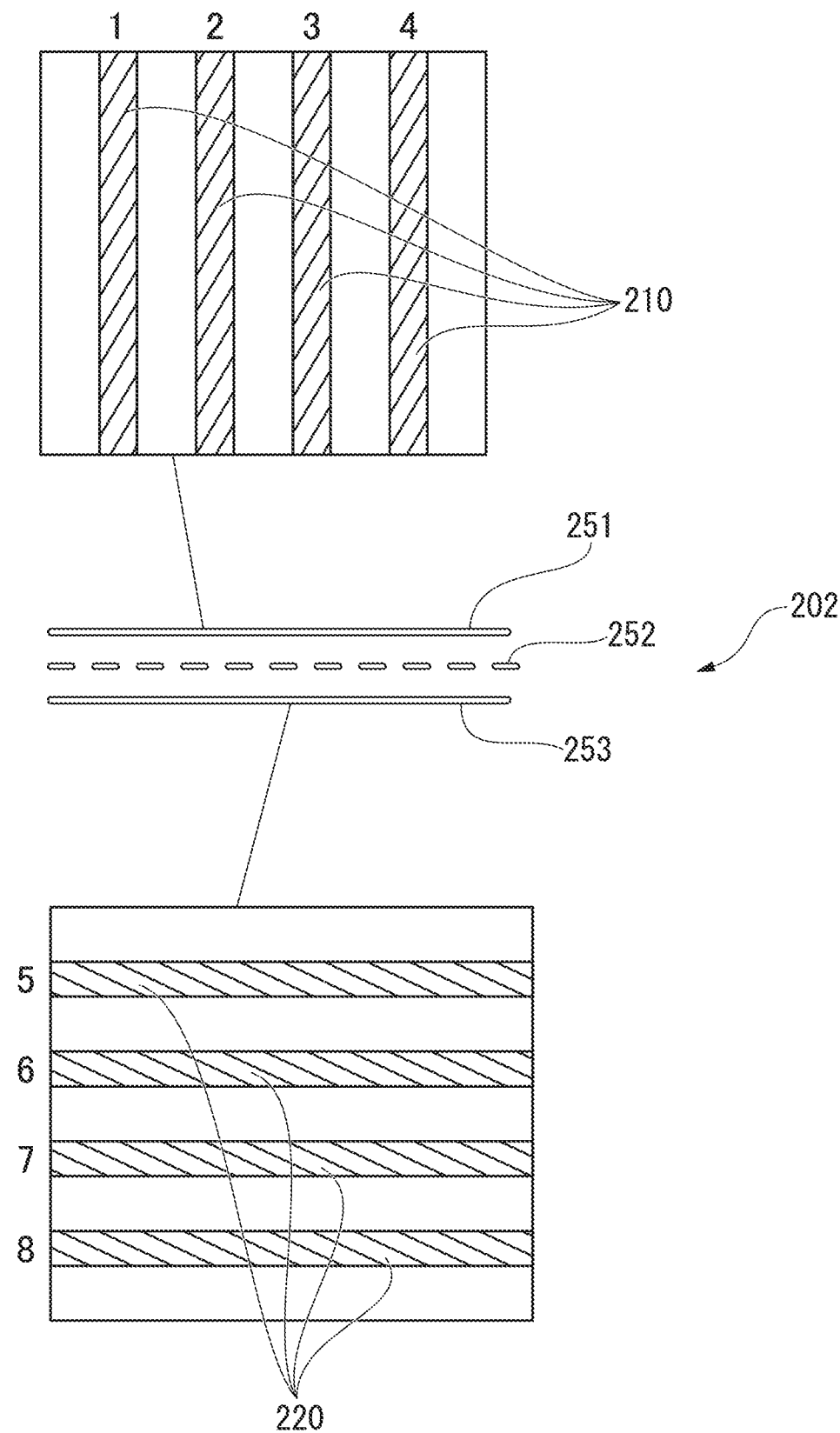
FIG. 46 is a view describing a fourth example of another disposition of the first conductive body and the second conductive body in the embodiment.

FIG. 46 is a view describing a fourth example of another disposition of the first conductive body 210 and the second conductive body 220. In FIG. 46, the fiber sheet 202 is configured as a 3-layer structure in which a sheet 252 is sandwiched between a sheet 251 including the first conductive body 210 and a sheet 253 including the second conductive body 220. In addition, the first conductive body 210 and the second conductive body 220 are disposed in different directions. In addition, all of a main body of the sheet 251, a main body of the sheet 253, and the sheet 252 are insulating sheets having absorbency. As the sheet 252 is sandwiched, the first conductive body 210 and the second conductive body 220 do not come in contact with each other.

In the example in FIG. 46 different from the example in FIG. 45, wires of the first conductive body 210 are not electrically connected to each other, and the wires configure a channel 1 to a channel 4. In addition, wires of the second conductive body 220 are not electrically connected to each other, and the wires configure a channel 5 to a channel 8.

Figure 47:
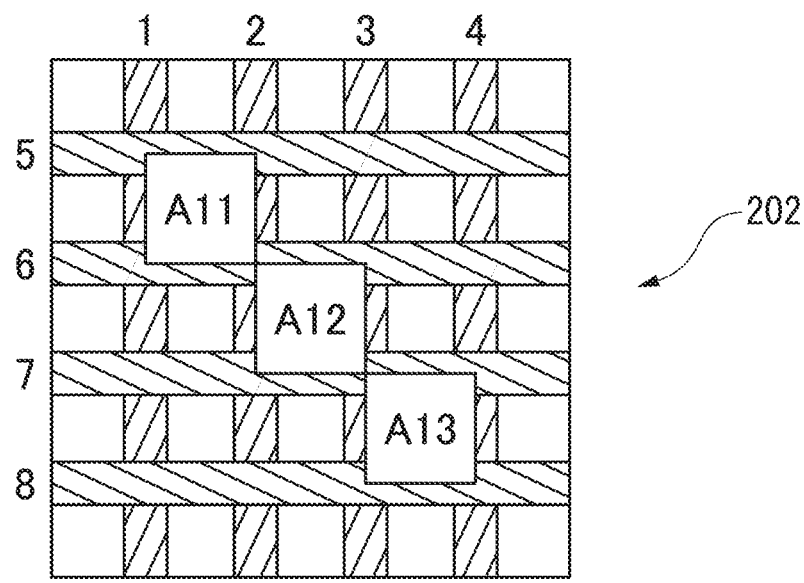
FIG. 47 is a view describing an example of a positional relationship between each of channels of the first conductive body and each of channels of the second conductive body in the embodiment.

FIG. 47 is a view describing an example of a positional relationship between the channels of the first conductive body 210 and the channels of the second conductive body 220. In the example in FIG. 47, the channels of the first conductive body 210 and the channels of the second conductive body 220 are disposed to perpendicular to each other. However, as the sheet 252 is sandwiched, the channels of the first conductive body 210 and the channels of the second conductive body 220 do not come in contact with each other. When a liquid permeates into a portion of the sheet 252, in the channel according to the permeated position, frequency characteristics of the first conductive body 210 and the second conductive body 220 are varied. Accordingly, the detection signal output unit 191 can detect an exuded position in addition to existence or non-existence of the liquid.

For example, the fiber sheet 202 is used as a carpet, and an instrument is installed in each of regions A11, A12 and A13 on the fiber sheet 202. In this case, when frequency characteristics between the channel 2 and the channel 5 are varied, it is possible to detect necessity for protecting the instrument installed in the region A11 from a malfunction due to the attached liquid. When frequency characteristics between the channel 3 and the channel 7 are varied, it is possible to detect necessity for protecting the instrument installed in the region A12 or the instrument installed in the region A13 from a malfunction due to the attached liquid.

In this way, the detection system 1 can be applied to detect various liquids that change the frequency characteristics between the first conductive body 210 and the second conductive body 220 without being limited to detect removal of a needle.

Further, when there is no need to discriminate types of liquid, even when direct current instead of the alternating current signal is applied to the channel, the position at which the liquid permeates into the fiber sheet 202 can be detected.

For example, in a state in which the direct current is applied to the channel 1 and the channel 2, as a voltage of each of the channel 5 and the channel 6 is measured, whether liquid permeates into the region A11 can be determined. In this case, when a conductance of the liquid shows a value sufficiently larger than a conductance of air and a measurement value of a predetermined magnitude or less with respect to a potential difference between the channel 5 and the channel 6 is obtained, it is determined that the liquid permeates into the region A11.

In addition, the other configuration may be employed as long as at least two conductive bodies (conductive yarns) are combined on the bandage-shaped fiber sheet such that they do not come in contact with each other to form a single yarn.

Figure 48:
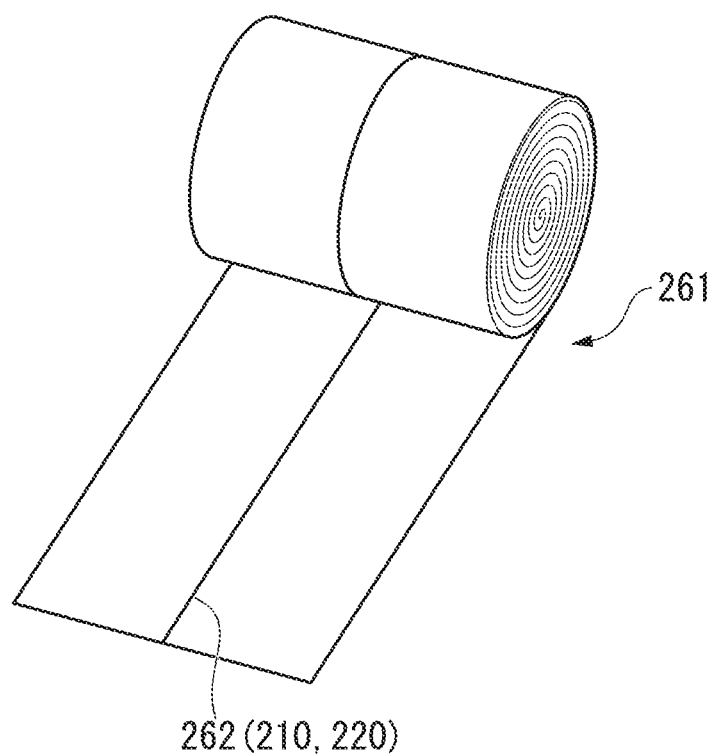
FIG. 48 is a view describing a first example of the disposition of yarns assembled such that two conductive bodies do not come into contact with each other in the embodiment.

FIG. 48 is a view describing a first example of the disposition of yarns combined such that two conductive bodies do not come in contact with each other.

In FIG. 48, a bandage 261 (a fiber sheet) is configured to include a yarn 262 longitudinally woven at a center of the bandage 261. The yarn 262 is configured to include two conductive bodies that are combined such that they do not come in contact with each other. The bandage 261 corresponds to an example of the fiber sheet 200, and the two conductive bodies included in the yarn 262 corresponds to an example of the first conductive body 210 and the second conductive body 220.

Further, disposition of the two conductive bodies included in one yarn is not limited to disposition shown in the example in FIGS. 9 and 10.

Figure 49:
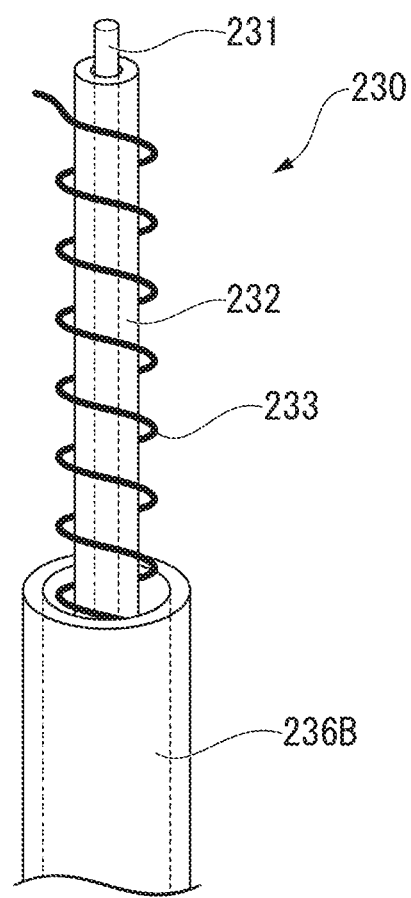
FIG. 49 is a structural view showing a schematic structure of another type of the sensor fiber shown in FIG. 9.

For example, as shown in FIG. 49, the conductive yarn 233 is not coated with an insulating cotton 236 and wound on the conductive yarn 231 coated with the insulating cotton 232, and these may be configured to be coated with an insulating cotton 236B (a third insulating section).

In addition, the sensor fiber 230 shown in FIG. 9 may be further coated with the insulating cotton 236B shown in FIG. 49.

Figure 50:
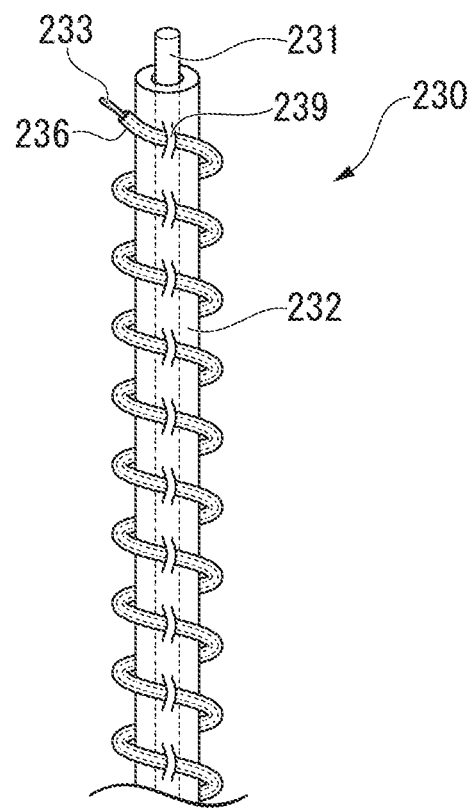
FIG. 50 is a structural view showing a schematic structure of another type of the sensor fiber shown in FIG. 9.

In addition, as shown in FIG. 50, in order to suppress movement of the conductive yarn 233 and the insulating cotton 236 wound on an outer circumference of the insulating cotton 232 in an extending direction of the conductive yarn 231, the insulating cotton 236 and the conductive yarn 232 may be woven with each other. That is, loops 239 are formed on an outer surface of the insulating cotton 232, and the conductive yarn 233 and the insulating cotton 236 may pass through the loops 239.

Figure 51:
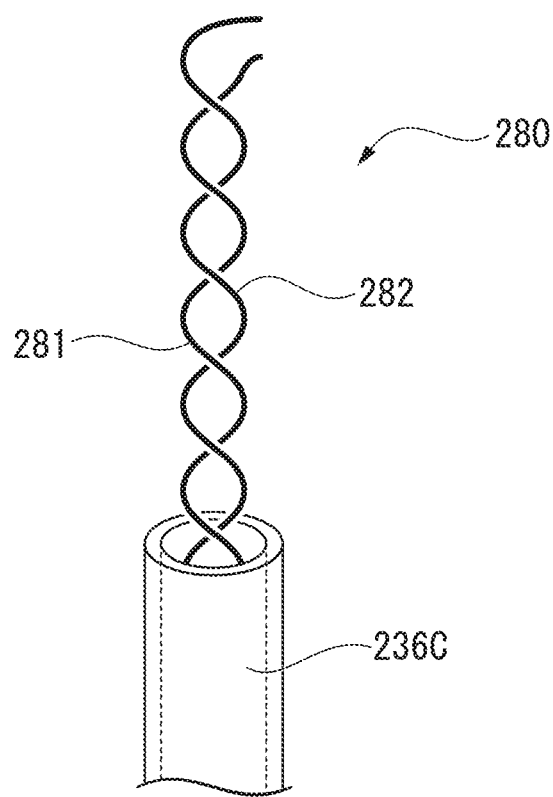
FIG. 51 is a view describing another example of disposition of two conductive bodies included in one yarn in the embodiment.

FIG. 51 is a view describing another example of disposition of two conductive bodies included one yarn. In FIG. 51, a yarn 280 is configured to include two conductive yarns 281 and 282 that are stranded such that they do not come in contact with each other.

For example, the conductive yarns 281 and 282 are coated with a material having an elastic property such as rubber or the like and twisted to form disposition as shown in FIG. 51. Accordingly, the conductive yarns 281 and 282 can be disposed at a relatively narrow interval, and the electric property can be provided in the yarn 280.

Each of the conductive yarn 281 and the conductive yarn 282 may be coated with insulating cotton, and as shown in FIG. 51, the conductive yarn 281 and the conductive yarn 282 that are twisted may be coated with insulating cotton 236C.

Further, even in all types shown in FIGS. 49, 50 and 51, a shield layer formed of a conductive yarn coated with an insulating material (for example, insulating cotton) having absorbency on an outer circumferential side thereof may be provided.

For example, in a state in which the conductive yarn coated with the insulating cotton is further wound or woven on the outer circumferential side of the conductive yarn 233 or the outer circumferential side of the insulating cotton 236B in the aspect shown in FIG. 49, the conductive yarn may be grounded.

As the shield layer is formed, an influence of noise or disturbance can be reduced.

Figure 52:
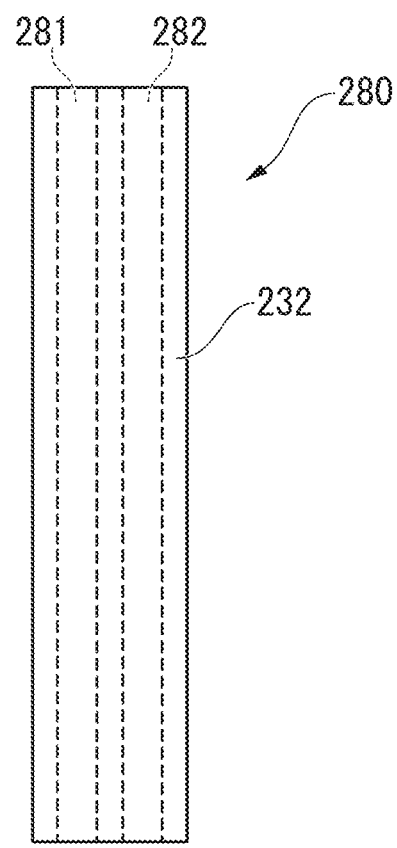
FIG. 52 is a view describing still another example of disposition of the two conductive bodies included in one yarn in the embodiment.

FIG. 52 is a view describing still another example of disposition of two conductive bodies included in one yarn.

Figure 53:
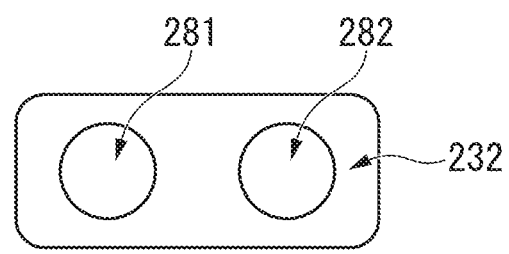
FIG. 53 is a view describing a disposition example of the two conductive bodies in a cross section of the yarn shown in FIG. 52.

FIG. 53 is a view describing a disposition example of two conductive bodies in a cross section of the yarn exemplarily shown in FIG. 52.

In the yarn 280 exemplarily shown in FIGS. 52 and 53, the two conductive yarns 281 and 282 are parallelly disposed, and two conductive yarns are coated with an insulating material having absorbency such as the insulating cotton 232 or the like. In the structure, there is no need to twist the conductive yarns, and in this point, the yarn can be relatively easily generated.

Even in the aspect shown in FIG. 52, in a state in which the conductive yarn coated with the insulating cotton is further wound or woven on the outer circumferential side of the insulating cotton 232, the conductive yarn may be earth-grounded.

As described above, the frequency characteristics acquisition unit 120 acquires frequency characteristics when an alternating current signal is input to at least two conductive bodies formed on the fiber sheet. In addition, the detection signal output unit 191 outputs a detection signal when the frequency characteristics acquisition unit 120 acquires predetermined frequency characteristics.

Accordingly, in the detection device 100, attachment of a specific liquid can be detected distinctly from the other liquid on the basis of a difference in the frequency characteristics.

In addition, in the detection device 100, the fiber sheet in which at least two conductive bodies (the first conductive body 210 and the second conductive body 220) are provided may be used. As the fiber sheet, for example, the fiber sheet in which a plurality of conductive yarns is woven may be used, and a fiber sheet structure can be simplified. Accordingly, manufacturing cost of the fiber sheet can be reduced, and the fiber sheet (a portion to which the liquid is attached) can be disposable.

In addition, the frequency characteristics acquisition unit 120 acquires frequency characteristics when an alternating current signal having a first frequency and an alternating current signal having a second frequency are input to at least two conductive bodies (the first conductive body 210 and the second conductive body 220), respectively. Then, the detection signal output unit 191 outputs a detection signal in the case in which a difference between the frequency characteristics when the alternating current signal having the first frequency is input to the conductive body and the frequency characteristics when the alternating current signal having the second frequency is input to the conductive body is a predetermined difference.

Here, as described above, in the sweat and the blood, ratios of variations in frequency characteristics with respect to the variations in frequency are different. For this reason, the detection signal output unit 191 can detect the blood distinctly from the sweat on the basis of the difference in frequency characteristics of the plurality of frequencies, and there is less misdetection of removal of a needle.

In this way, the detection signal output unit 191 can distinctly detect the specific liquid and the other liquid on the basis of a difference in frequency characteristics of the plurality of frequencies.

In addition, the fiber sheet 200 includes the conductive yarns 231 and 233 (the yarn 262 or the yarn 280) including at least two conductive bodies 210 and 220 that are combined such that they do not come in contact with each other.

Accordingly, the two conductive bodies 210 and 220 can be disposed at a relatively narrow interval, and when the liquid permeates into the fiber sheet 200, detection accuracy of the detection signal output unit 191 can be increased.

Further, processing of the respective parts may be performed by recording a program for realizing a function of the detection signal output unit 191 on a computer-readable recording medium and reading and executing the program recorded on the recording medium using a computer system. Further, the "computer system" disclosed herein includes OS or hardware such as peripheral devices or the like.

In addition, the "computer system" also includes a homepage-providing environment (or a display environment) as long as a WWW system is used.

In addition, the "computer-readable recording medium" is a portable storage medium such as a flexible disk, a magneto-optic disk, a ROM, a CD-ROM, or the like, a storage device such as a hard disk or the like installed in a computer system, or the like. Further, the "computer-readable recording medium" includes a medium of dynamically holding a program during a short time such as a communication line when the program is transmitted via a communication channel such as a network, for example, the Internet or the like, a telephone line, or the like, and a medium of holding a program for a certain time such as a volatile memory in a computer system that is a server or a client in this case. In addition, the program may be configured to realize some of the above-mentioned functions, and may be configured to combine the above-mentioned functions to the program previously recorded in the computer system and realize the program.

Hereinabove, while the embodiment of the present invention has been described in detail with reference to the accompanying drawings, a specific configuration is not limited to the embodiment and may include design changes without departing from the scope of the present invention.

INDUSTRIAL APPLICABILITY

According to the yarn, the detection system, the fiber sheet, the connector, the detection device and the liquid type estimation method, whether a liquid dripping onto the fiber sheet is a predetermined liquid (for example, blood) can be accurately determined, and the possibility that a detection signal is incorrectly output can be reduced.

REFERENCE SIGNS LIST

1 Detection system
60 First connector
69 Recessed groove (groove)
70 Terminal for center conductor
71 Terminal for external conductor
75 Second connector
90 Third connector
95 Fourth connector
100 Detection device
110 Alternating current signal output unit
120 Frequency characteristics acquisition unit
130 Alarm output unit
180 Storage unit
181 Detecting conditions storage unit
190 Control unit
191 Detection signal output unit
200, 271 Fiber sheet
201 Fiber sheet main body
210 First conductive body
220 Second conductive body
230 Sensor fiber (yarn)
231, 233, 281, 282 Conductive yarn
232 Insulating cotton (first insulating section)
236 Insulating cotton (second insulating section)
241, 242, 243, 251, 252, 253 Sheet
261 Bandage
262, 280 Yarn

The invention claimed is:
1. A detection system, comprising:
a fiber sheet; and
a detection device,
wherein the fiber sheet comprises:
    a fiber sheet main body formed of an insulating material; and
    a sensor fiber including at least two conductive bodies that are combined such that they do not come in contact with each other,
wherein the sensor fiber comprises:
    a first conductive yarn of the at least two conductive bodies having conductivity;
    an insulating section covering the first conductive yarn and formed of an insulating material having absorbency; and
    a second conductive yarn of the at least two conductive bodies having conductivity and disposed on an outer circumferential side of the insulating section,
wherein the detection device comprises:
    an alternating current signal output unit configured to input an alternating current signal between the at least two conductive bodies formed on the fiber sheet;
    a frequency characteristics acquisition unit configured to acquire frequency characteristics between the conductive bodies when the alternating current signal output unit inputs an alternating current signal between the conductive bodies; and
    a detection signal output unit configured to output a detection signal when both of the following conditions are met, that is, when the alternating current signal output unit inputs a plurality of alternating current signals having different frequencies between the conductive bodies and the frequency characteristics acquired by the frequency characteristics acquisition unit show a predetermined difference according to a difference in frequency of the alternating current signal from the alternating current signal output unit, and when the alternating current signal output unit inputs the alternating current signals having the same frequency between the conductive bodies and the frequency characteristics obtained by the frequency characteristics acquisition unit at different times show a predetermined variation according to elapse of time, wherein the alternating current signal output unit inputs at least three alternating current signals having different frequencies between a plurality of conductive bodies formed on the fiber sheet, wherein the frequency characteristics acquisition unit acquires a value of impedance measured between the conductive bodies with each of the alternating current signals input by the alternating current signal output unit, and wherein the detection signal output unit determines whether the frequency characteristics which is acquired by the frequency characteristics acquisition unit when the alternating current signal output unit input a plurality of alternating current signal having different frequencies between the conductive bodies shows a predetermined difference according to a difference in frequency of the alternating current signal from the alternating current signal output unit by obtaining a Cole-Cole trajectory that approximates impedance measurement values acquired by the frequency characteristics acquisition unit at a portion of an arc; obtaining a value of a circuit parameter in a predetermined equivalent circuit model simulating an impedance of a liquid having a membrane on the basis of the Cole-Cole trajectory and estimating a type of the liquid on the basis of the obtained value of the circuit parameter.

2. A detection device, comprising:

an alternating current signal output unit configured to input an alternating current signal between a plurality of conductive bodies formed on a fiber sheet;

a frequency characteristics acquisition unit configured to acquire frequency characteristics between the conductive bodies when the alternating current signal output unit inputs an alternating current signal between the conductive bodies, and a detection signal output unit configured to output a detection signal when both of the following conditions are met, that is, when the alternating current signal output unit inputs a plurality of alternating current signals having different frequencies between the conductive bodies and the frequency characteristics acquired by the frequency characteristics acquisition unit show a predetermined difference according to a difference in frequency of the alternating current signal from the alternating current signal output unit, and when the alternating current signal output unit inputs the alternating current signals having the same frequency between the conductive bodies and the frequency characteristics acquired by the frequency characteristics acquisition unit at different times show a predetermined variation according to elapse of time, wherein the alternating current signal output unit inputs at least three alternating current signals having different frequencies between a plurality of conductive bodies formed on the fiber sheet, wherein the frequency characteristics acquisition unit acquires a value of impedance measured between the conductive bodies with each of the alternating current signals input by the alternating current signal output unit, and wherein the detection signal output unit determines whether the frequency characteristics which is acquired by the frequency characteristics acquisition unit when the alternating current signal output unit input a plurality of alternating current signal having different frequencies between the conductive bodies shows a predetermined difference according to a difference in frequency of the alternating current signal from the alternating current signal output unit by obtaining a Cole-Cole trajectory that approximates impedance measurement values acquired by the frequency characteristics acquisition unit at a portion of an arc; obtaining a value of a circuit parameter in a predetermined equivalent circuit model simulating an impedance of a liquid having a membrane on the basis of the Cole-Cole trajectory and estimating a type of the liquid on the basis of the obtained value of the circuit parameter.

3. A liquid or gas type estimation method, comprising:

an alternating current signal inputting step of inputting at least three alternating current signals having different frequencies between a plurality of conductive bodies formed on a fiber sheet;

an impedance measurement value acquisition step of acquiring a value of impedance measured between the conductive bodies with each of the alternating current signals input in the alternating current signal inputting step;

a Cole-Cole trajectory acquisition step of obtaining a Cole-Cole trajectory that approximates impedance measurement values obtained in the impedance measurement value acquisition step at a portion of an arc;

a capacitance acquisition step of obtaining a value of a circuit parameter in a predetermined equivalent circuit model simulating an impedance of a liquid having a membrane on the basis of the Cole-Cole trajectory; and a liquid type estimation step of estimating a type of the liquid on the basis of the obtained value of the circuit parameter, wherein the alternating current signal inputting step is performed by an alternating current signal output unit, wherein the impedance measurement value acquisition step is performed by a frequency characteristics acquisition unit configured to acquire frequency characteristics between the conductive bodies when the alternating current signal output unit inputs an alternating current signal between the conductive bodies, wherein the Cole-Cole trajectory acquisition step, the capacitance acquisition step, and the liquid type estimation step are performed by a detection signal output unit, wherein the detection signal output unit determines whether the frequency characteristics which is acquired by the frequency characteristics acquisition unit when the alternating current signal output unit input a plurality of alternating current signal having different frequencies between the conductive bodies shows a predetermined difference according to a difference in frequency of the alternating current signal from the alternating current signal output unit by performing the Cole-Cole trajectory acquisition step, the capacitance acquisition step, and the liquid type estimation step, wherein the detection signal output unit is configured to output a detection signal when both of the following conditions are met, that is, when the alternating current signal output unit inputs a plurality of alternating current signals having different frequencies between the conductive bodies and the frequency characteristics acquired by the frequency characteristics acquisition unit show a predetermined difference according to a difference in frequency of the alternating current signal from the alternating current signal output unit, and when the alternating current signal output unit inputs the alternating current signals having the same frequency between the conductive bodies and the frequency characteristics obtained by the frequency characteristics acquisition unit at different times show a predetermined variation according to elapse of time.

\* \* \* \* \*